US012582450B2

(12) United States Patent　　　　(10) Patent No.:　US 12,582,450 B2

Perez et al.　　　　　　　　　　　　　　(45) Date of Patent:　　Mar. 24, 2026

(54) BONE FIXATION DEVICES, SYSTEMS, AND METHODS

(71) Applicants: Edward Perez, Ft. Lauderdale, FL (US); Jan Szatkowski, Indianapolis, IN (US); Nephi Zufelt, Pocatello, ID (US); Corey Johnson, Rochester, MN (US)

(72) Inventors: Edward Perez, Ft. Lauderdale, FL (US); Jan Szatkowski, Indianapolis, IN (US); Nephi Zufelt, Pocatello, ID (US); Corey Johnson, Rochester, MN (US)

(73) Assignee: PS Ortho LLC, Ft. Lauderdale, FL (US)

( * ) Notice: Subject to any disclaimer, the term of this patent is extended or adjusted under 35 U.S.C. 154(b) by 418 days.

(21) Appl. No.: 17/889,907

(22) Filed: Aug. 17, 2022

(65) Prior Publication Data

US 2023/0055444 A1　　Feb. 23, 2023

Related U.S. Application Data

(60) Provisional application No. 63/233,996, filed on Aug. 17, 2021.

(51) Int. Cl.
| | |
|---|---|
| *A61B 17/72* | (2006.01) |
| *A61B 17/17* | (2006.01) |
| *A61B 17/74* | (2006.01) |
| *A61B 17/80* | (2006.01) |

(Continued)

(52) U.S. Cl.
CPC ...... *A61B 17/7216* (2013.01); *A61B 17/1725* (2013.01); *A61B 17/1728* (2013.01); *A61B 17/72* (2013.01); *A61B 17/7233* (2013.01);

*A61B 17/744* (2013.01); *A61B 17/8023* (2013.01); *A61B 17/8057* (2013.01); *A61B 17/8061* (2013.01); *A61B 17/808* (2013.01);

(Continued)

(58) Field of Classification Search
CPC ............ A61B 17/7241; A61B 17/1725; A61B 17/744; A61B 17/808; A61B 17/1728; A61B 17/921; A61B 17/1717
See application file for complete search history.

(56) References Cited

U.S. PATENT DOCUMENTS

| | | |
|---|---|---|
| 4,135,507 A | 1/1979 | Harris |
| 4,776,330 A | 10/1988 | Chapman |

(Continued)

FOREIGN PATENT DOCUMENTS

| | | | |
|---|---|---|---|
| CN | 104287818 A | 1/2015 | |
| CN | 109171917 B | * 6/2020 | ............ A61B 17/90 |
| WO | WO2010061410 A1 | 6/2010 | |

OTHER PUBLICATIONS

International Search Report dated Dec. 5, 2022 for corresponding Application No. PCT/US2022/040609.

*Primary Examiner* — David W Bates
(74) *Attorney, Agent, or Firm* — David Meibos; Maywood IP Law

(57) ABSTRACT

A combined inserter for insertion of an intramedullary nail and a bone plate together. The combined inserter includes a body that includes a longitudinal axis, a distal end, and a proximal end. The combined inserter includes an intramedullary nail coupler coupled to the body and configured to couple to an intramedullary nail; and a bone plate coupler coupled to the body and configured to couple to a bone plate.

26 Claims, 45 Drawing Sheets

(51) Int. Cl.
    *A61B 17/00*          (2006.01)
    *A61B 17/68*          (2006.01)

(52) U.S. Cl.
    CPC .............. *A61B 2017/00477* (2013.01); *A61B 2017/00991* (2013.01); *A61B 2017/681* (2013.01)

(56)            References Cited

U.S. PATENT DOCUMENTS

| | | | | |
|---|---|---|---|---|
| 5,433,720 | A * | 7/1995 | Faccioli | A61B 17/80 |
| | | | | 606/98 |
| 5,620,445 | A | 4/1997 | Brosnahan | |
| 5,626,580 | A | 5/1997 | Brosnahan | |
| 5,749,872 | A | 5/1998 | Kyle | |
| 5,827,286 | A | 10/1998 | Incavo | |
| 6,010,506 | A | 1/2000 | Gosney | |
| 6,645,210 | B2 | 11/2003 | Manderson | |
| 7,842,036 | B2 | 11/2010 | Phillips | |
| 7,951,176 | B2 | 5/2011 | Grady, Jr. | |
| 8,628,533 | B2 | 1/2014 | Graham | |
| 8,679,130 | B2 * | 3/2014 | Smith | A61B 17/1753 |
| | | | | 606/89 |
| 8,709,092 | B2 * | 4/2014 | Segina | A61F 2/3609 |
| | | | | 606/70 |
| 8,808,333 | B2 | 8/2014 | Kuster | |
| 9,089,375 | B2 * | 7/2015 | Smith | A61B 17/1728 |
| 9,101,421 | B2 | 8/2015 | Blacklidge | |
| 9,839,435 | B2 | 12/2017 | Meek | |
| 9,968,389 | B2 | 5/2018 | Garino | |
| 9,993,272 | B2 | 6/2018 | Gordon | |
| 10,136,929 | B2 | 11/2018 | Fallin | |
| 10,307,188 | B2 | 6/2019 | Harshman | |
| 10,314,626 | B2 * | 6/2019 | Koay | A61B 17/7241 |
| 10,695,111 | B2 | 6/2020 | Biedermann | |
| 10,743,923 | B2 | 8/2020 | Ananthan | |
| 10,751,096 | B2 * | 8/2020 | Hedgeland | A61B 17/1697 |
| 10,856,920 | B2 | 12/2020 | Tiongson | |
| 10,959,762 | B2 * | 3/2021 | Williams | A61B 17/725 |
| 11,013,540 | B2 | 5/2021 | Petersik | |
| 11,844,554 | B1 * | 12/2023 | Machamer | A61B 17/72 |
| 2001/0012939 | A1 | 8/2001 | Wahl | |
| 2002/0151898 | A1 | 10/2002 | Sohngen | |
| 2003/0004513 | A1 * | 1/2003 | Guzman | A61B 17/1728 |
| | | | | 606/62 |
| 2004/0102778 | A1 | 5/2004 | Huebner | |
| 2006/0235404 | A1 | 10/2006 | Orbay | |
| 2007/0005146 | A1 | 1/2007 | Heyligers | |
| 2007/0173834 | A1 | 7/2007 | Thakkar | |
| 2007/0173839 | A1 | 7/2007 | Running | |
| 2007/0173843 | A1 * | 7/2007 | Matityahu | A61B 17/80 |
| | | | | 606/281 |
| 2007/0219636 | A1 * | 9/2007 | Thakkar | A61B 17/1721 |
| | | | | 623/18.11 |
| 2011/0251614 | A1 * | 10/2011 | Piraino | A61B 17/68 |
| | | | | 606/62 |
| 2011/0313422 | A1 | 12/2011 | Schwager et al. | |
| 2012/0232596 | A1 | 9/2012 | Ribeiro | |
| 2013/0030435 | A1 * | 1/2013 | Perez | A61B 17/7233 |
| | | | | 606/64 |
| 2014/0114312 | A1 | 4/2014 | Krause | |
| 2015/0005831 | A1 | 1/2015 | Sands | |
| 2015/0289910 | A1 | 10/2015 | Mirghasemi et al. | |
| 2015/0305791 | A1 * | 10/2015 | Purohit | A61B 17/8872 |
| | | | | 606/96 |
| 2016/0206356 | A1 * | 7/2016 | Koay | A61B 17/80 |
| 2016/0310183 | A1 | 10/2016 | Shah et al. | |
| 2017/0265915 | A1 * | 9/2017 | Langdale | A61B 17/8057 |
| 2018/0256220 | A1 | 9/2018 | Koay | |
| 2019/0000509 | A1 * | 1/2019 | Cowens | A61B 17/1728 |
| 2019/0053836 | A1 | 2/2019 | Sweeney | |
| 2020/0129297 | A1 * | 4/2020 | Haidukewych | A61B 17/744 |
| 2020/0315674 | A1 | 10/2020 | Sylvestre et al. | |
| 2021/0121211 | A1 | 4/2021 | Labrum, IV | |
| 2021/0267653 | A1 | 9/2021 | Destainville et al. | |
| 2021/0275195 | A1 * | 9/2021 | Wong | A61B 17/17 |
| 2022/0117639 | A1 * | 4/2022 | Gabelberger | A61B 17/8085 |
| 2023/0058351 | A1 * | 2/2023 | Perez | A61B 17/8023 |
| 2023/0225773 | A1 * | 7/2023 | Machamer | A61B 17/746 |
| | | | | 606/62 |
| 2024/0156499 | A1 * | 5/2024 | Zander | A61B 17/8061 |
| 2024/0173041 | A1 * | 5/2024 | Zander | A61B 17/8061 |
| 2024/0277388 | A1 * | 8/2024 | Haidukewych | A61B 17/72 |
| 2025/0090207 | A1 * | 3/2025 | Machamer | A61B 17/1725 |
| 2025/0204963 | A1 * | 6/2025 | Haidukewych | A61B 17/744 |

* cited by examiner

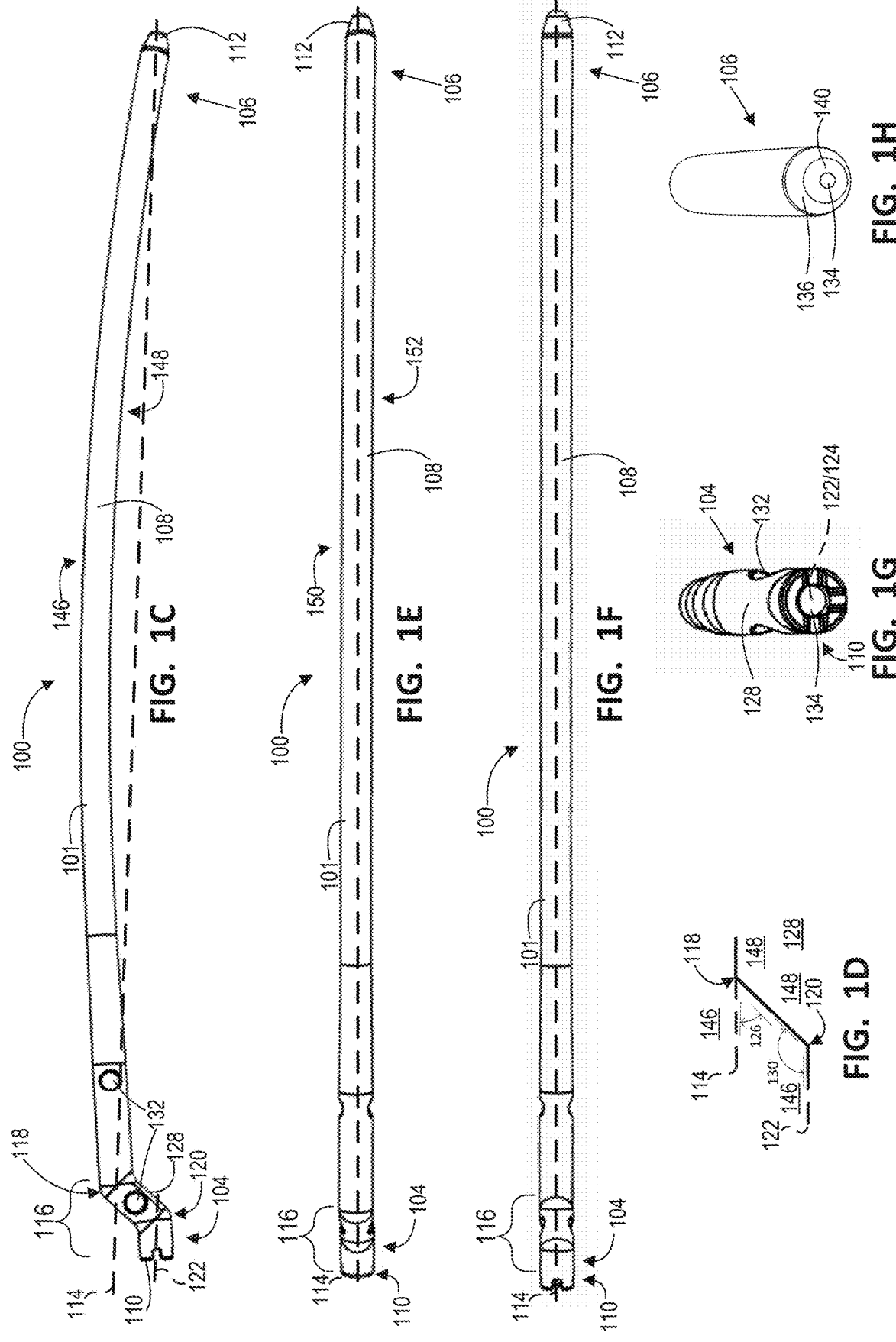

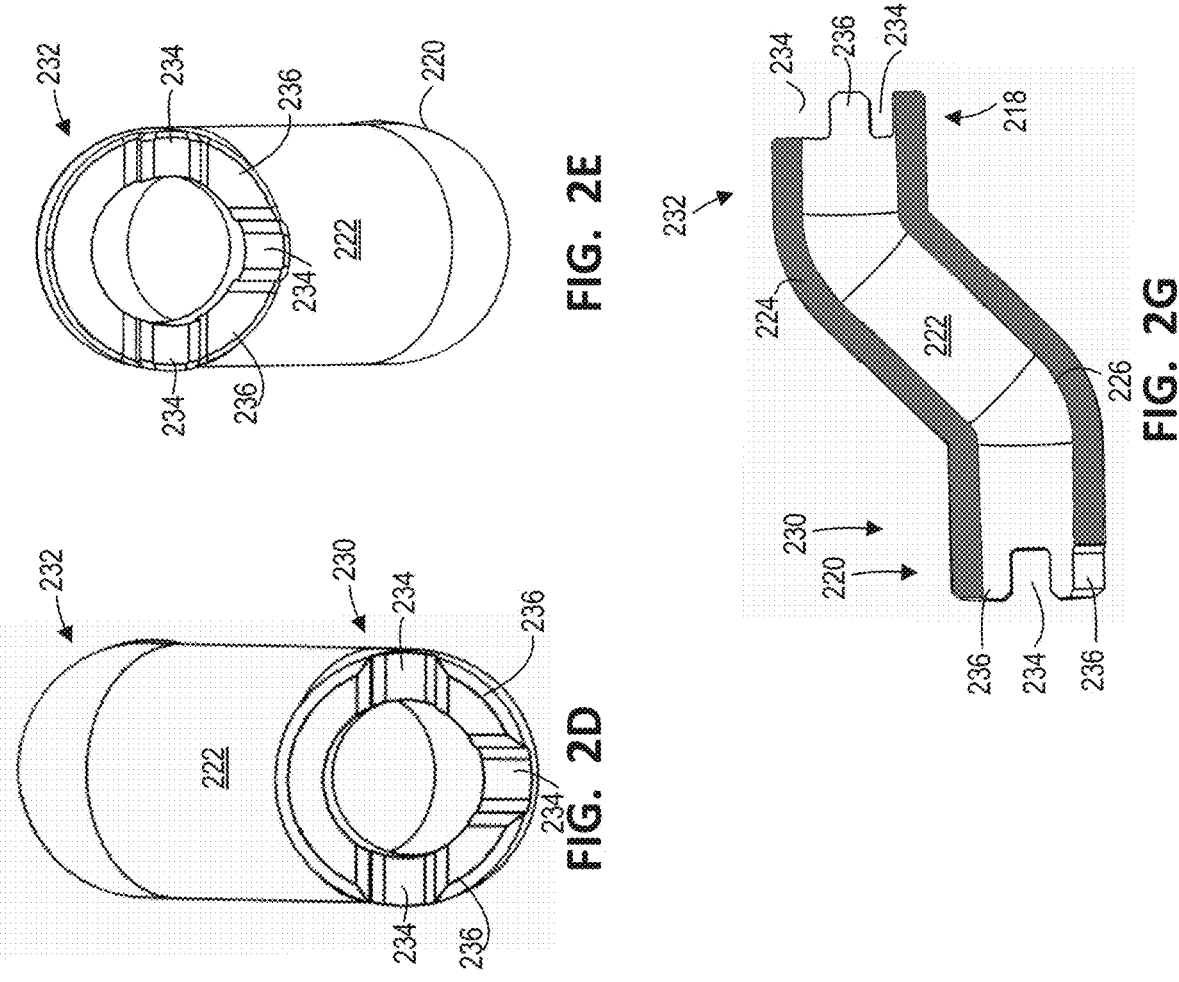
FIG. 2E
FIG. 2D
FIG. 2G
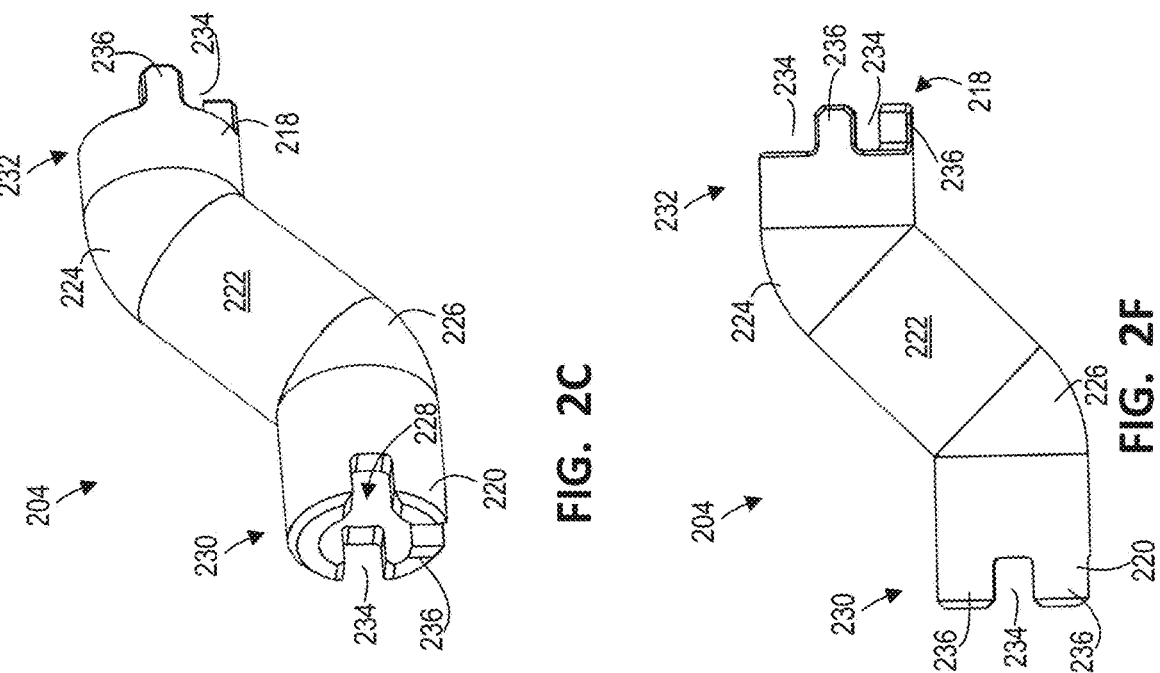
FIG. 2C
FIG. 2F

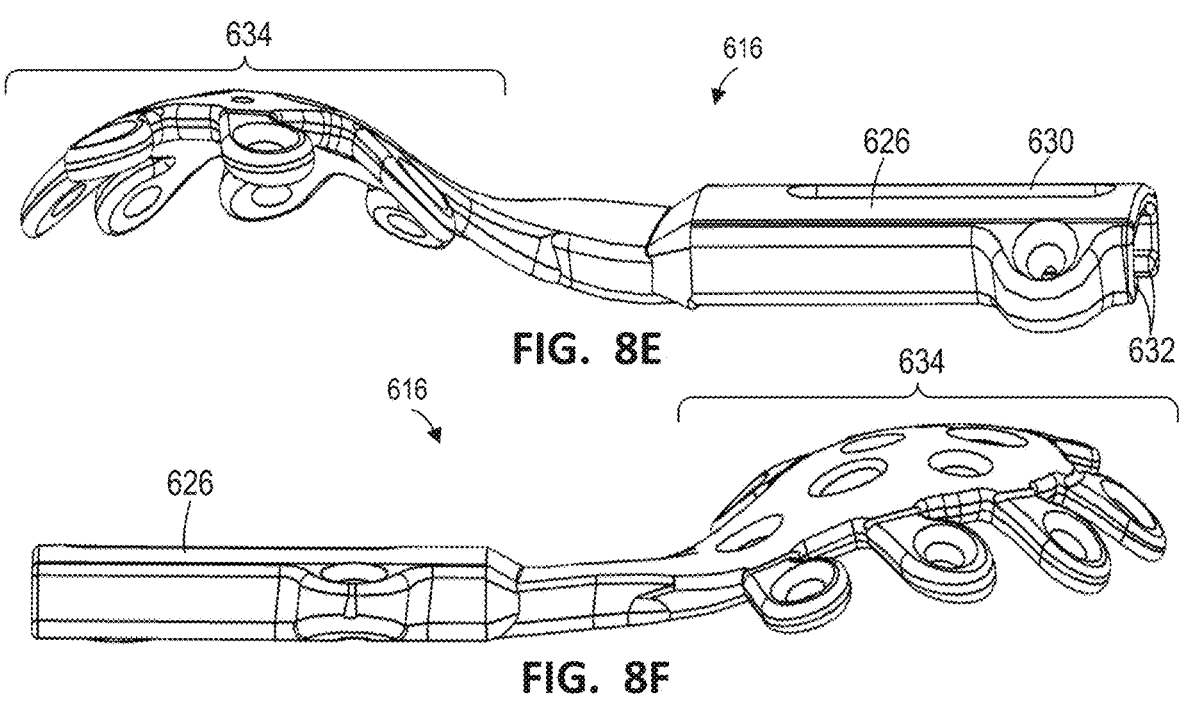
FIG. 8E
FIG. 8F
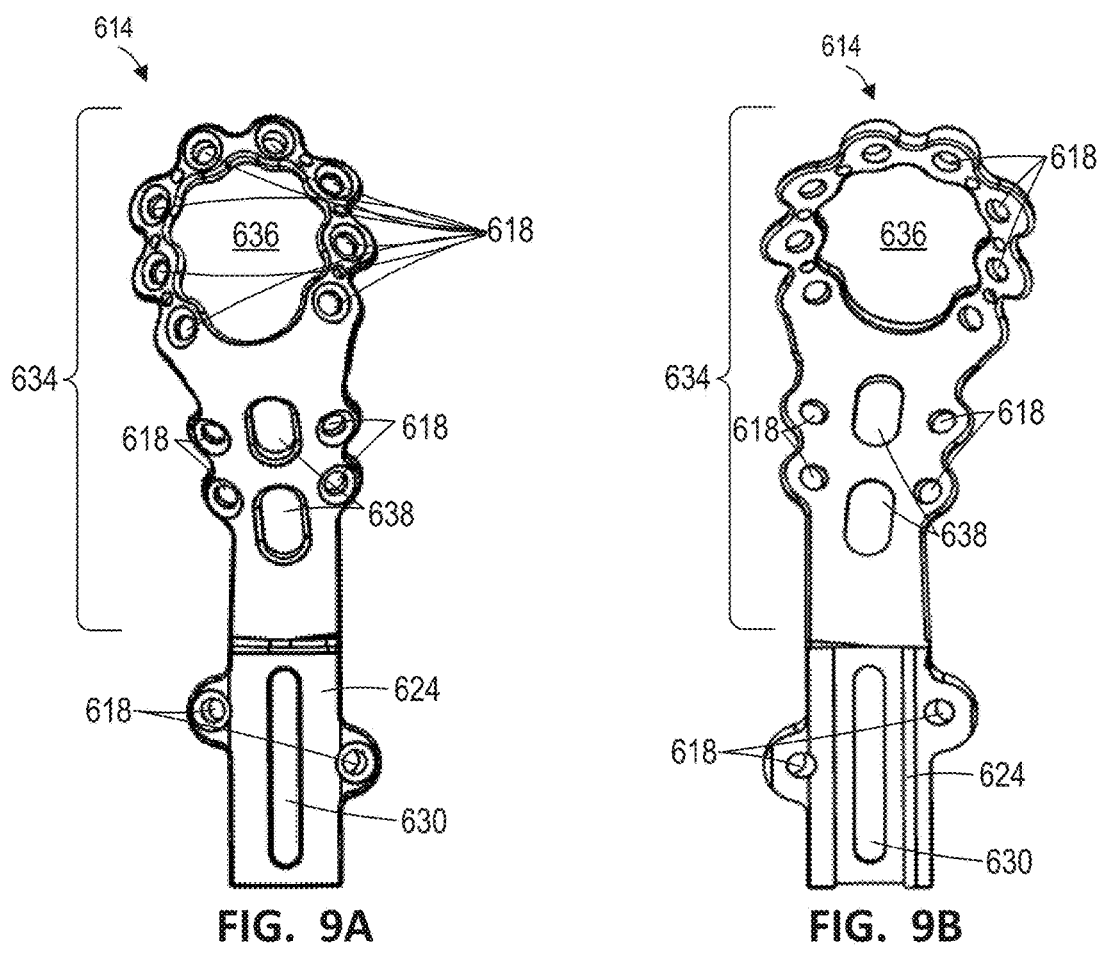
FIG. 9A          FIG. 9B

FIG. 14A          FIG. 14B

BONE FIXATION DEVICES, SYSTEMS, AND METHODS

CROSS-REFERENCE TO RELATED APPLICATIONS

This application claims the benefit of U.S. Provisional Application No. 63/233,996, filed Aug. 17, 2021, which is hereby incorporated by reference in its entirety.

TECHNICAL FIELD

The present disclosure relates to surgical devices, systems, instruments, and methods. More specifically, the present disclosure relates to long bone fixation devices, systems, instruments, and methods of designing and/or using the same.

BACKGROUND

Various surgical procedures in people and animals include a fixation step, procedure, use of a device (also referred to as a fixator), or the like. The fixation feature, or function, may be between two pieces of bone, between two soft tissues, between soft tissue and bone, or within a medullary cavity of a long bone. Unfortunately, many known long bone fixation techniques, steps, procedures, devices, or components are complicated, difficult to deploy, involve multiple parts, are not easy to deploy when a patient has received a prosthesis such as a joint or fixation prostheses, femoral component for a partial or total knee replacement (TKR) procedure, a femoral component for a total hip replacement, experienced a peri-implant fracture, and have other limitations. Additionally, known long bone fixation techniques, steps, procedures, devices, or components can increase one or more types of stiffness of the fixation system or component in such a way that contributes to stress-shielding and/or non-unions of fractures. Also, known instrumentation can include multiple apparatus, require extra and/or larger incisions in a patient, and still not assist a surgeon in fixating one or more implants to a long bone in a manner that provides optimal stability for the fixation. The present disclosure addresses these limitations of the known long bone fixation techniques, steps, procedures, devices, or components.

SUMMARY

The various apparatus, devices, systems, and/or methods of the present disclosure have been developed in response to the present state of the art, and in particular, in response to the problems and needs in the art that have not yet been fully solved by currently available technology. One general aspect of the present disclosure can include a combined inserter that enables insertion of an intramedullary nail and a bone plate together. The combined inserter includes a body that may include a longitudinal axis, a distal end, and a proximal end; an intramedullary nail coupler coupled to the body and configured to couple to an intramedullary nail, and a bone plate coupler coupled to the body and configured to couple to a bone plate.

Implementations may include one or more of the following features. The combined inserter where the bone plate coupler may include: a longitudinal translation feature configured to translate the bone plate coupler along the longitudinal axis between the proximal end and the distal end; a transverse feature configured to translate the bone plate coupler along a transverse axis transverse to the longitudinal axis; and a rotational feature configured to rotate the bone plate about a longitudinal bone plate axis. The longitudinal translation feature may include: a track between the proximal end and the distal end, the track may include one or more offset positions and a nail alignment position configured to align the intramedullary nail and the bone plate with each other for deployment within a patient; and a latch configured to secure the longitudinal translation feature in one of the one or more offset positions and the nail alignment position. The nail alignment position may include an alignment of at least one fastener opening of the bone plate with at least one corresponding fastener opening of the intramedullary nail such that a fastener deployed within the at least one fastener opening of the bone plate engages the at least one corresponding fastener opening of the intramedullary nail. One of the one or more offset positions position the bone plate such that advancement of the combined inserter toward a bone of a patient causes the intramedullary nail to enter an intramedullary canal of the bone before the bone plate percutaneously advances along a side of the bone, the combined inserter may include the intramedullary nail and the bone plate. One of the one or more offset positions position the bone plate such that advancement of the combined inserter toward a bone of a patient causes the bone plate to percutaneously advance along a side of the bone before the intramedullary nail enters an intramedullary canal of the patient, the combined inserter may include the intramedullary nail and the bone plate. The transverse feature may include: a base; a telescoping member configured to fit within the base; a fastener configured to secure the telescoping member within the base; where extending or retracting the telescoping member advances or retracts the bone plate along the transverse axis. The rotational feature connects the bone plate to the transverse feature. The rotational feature may include a clevis joint. One or more of the longitudinal translation feature, the transverse feature, and the rotational feature may include a deployment configuration configured to position an intramedullary nail coupled to the intramedullary nail coupler relative to a bone plate coupled to the bone plate coupler for deployment of fasteners. The body may include a guide section, the guide section may include a set of nail engagement openings and a set of nail avoidance openings, each of the nail engagement openings and the nail avoidance openings aligned with a fastener opening of the bone plate. The guide section includes at least one indicator of one of the set of nail engagement openings and the set of nail avoidance openings. The intramedullary nail coupler may include a coupling configured to releasably connect the intramedullary nail coupler to the body. The body may include a distal handle proximal to the distal end and a proximal handle near the proximal end.

One general aspect of the present disclosure can include a femur fixation system. The femur fixation system includes an intramedullary nail that may include a set of nail fastener openings configured accept a fastener, the intramedullary nail configured to slide into an intramedullary canal of a femur of a patient; a bone plate may include a set of plate fastener openings; a combined inserter may include: a body may include a longitudinal axis, a distal end, and a proximal end; an intramedullary nail coupler coupled to the body and configured to couple to the intramedullary nail; a bone plate coupler coupled to the body and configured to couple to the bone plate; a set of nail engagement openings that align with at least one of the set of nail fastener openings, the set of nail engagement openings disposed in the body. The system includes a set of nail engagement fasteners configured to engage both the bone plate and the intramedullary nail when deployed; and a set of nail avoidance fasteners configured to engage the bone plate and the femur of the patient when deployed.

Implementations may include one or more of the following features. The femur fixation system where at least one member of the set of plate fastener openings may include a nail avoidance opening. The bone plate coupler may include: a transverse feature configured to bias the bone plate towards the femur and move the bone plate away from the femur in response to a force away from the femur; and a rotational feature may include a pivot joint that enables the bone plate to move in at least two directions relative to the bone plate coupler. The transverse feature and the rotational feature each may include a deployment configuration configured to position the intramedullary nail coupled to the intramedullary nail coupler relative to the bone plate coupled to the bone plate coupler for deployment of the nail engagement fasteners and the nail avoidance fasteners.

One general aspect of the present disclosure can include a method for stabilizing a bone fracture in a femur of a patient. The method includes coupling an intramedullary nail to a combined inserter; coupling a bone plate to the combined inserter, the combined inserter may include: a body may include a longitudinal axis, a distal end, and a proximal end; an intramedullary nail coupler coupled to the body and configured to couple to the intramedullary nail; a bone plate coupler coupled to the body and configured to couple to the bone plate; where each of the intramedullary nail coupler and the bone plate coupler may include a deployment configuration. The method includes preparing an intramedullary canal of a femur of the patient, the intramedullary canal extending from a distal end of the femur to a proximal end of the femur; forming an incision in skin of the patient proximal to a distal end of the femur, the incision sized to accept the bone plate; inserting the intramedullary nail together with the bone plate by moving the combined inserter retrograde from the distal end of the femur toward the proximal end of the femur, the intramedullary nail moving within the intramedullary canal and the bone plate moving percutaneously along a lateral surface of the femur; moving the intramedullary nail coupler and the bone plate coupler into the deployment configuration; and deploying one or more fasteners that fixate the bone plate to the lateral surface of the femur.

Implementations may include one or more of the following features. The method where inserting the intramedullary nail together with the bone plate further may include adjusting the bone plate coupler such that the bone plate can be moved in at least two directions relative to the bone plate coupler.

BRIEF DESCRIPTION OF THE DRAWINGS

The advantages, nature, and additional features of exemplary embodiments of the disclosure will become more fully apparent from the following description and appended claims, taken in conjunction with the accompanying drawings. Understanding that these drawings depict only exemplary embodiments and are, therefore, not to be considered limiting of the disclosure's scope, the exemplary embodiments of the disclosure will be described with additional specificity and detail through use of the accompanying drawings in which:

FIGS. 1C, 1D, IE, 1F, 1G, and 1H are a side view, angle diagram, top view, bottom view, distal end view, and proximal end view respectively of or in relation to the intramedullary nail of FIG. 1A, according to one embodiment.

FIG. 2C is a perspective view of the adapter of FIG. 2A, according to one embodiment.

FIGS. 2D, 2E, and 2F are distal end view, proximal end view, and side view respectively of the adapter of FIG. 2C, according to one embodiment.

FIG. 2G is longitudinal cross-section view of the adapter of FIG. 2C, according to one embodiment.

FIGS. 8A, 8B, 8C, 8D, 8E, and 8F are front view, rear view, bottom view, top view, right side view, and left side view respectively of a distal extender, according to one embodiment.

FIGS. 9A, 9B, 9C, 9D, 9E, and 9F are front view, rear view, bottom view, top view, right side view, and left side view respectively of a proximal extender, according to one embodiment.

FIGS. 14A, 14B, and 14C are perspective view, top view, and bottom view respectively of a fastener, according to one embodiment.

DETAILED DESCRIPTION

Figures 1A, 1B:
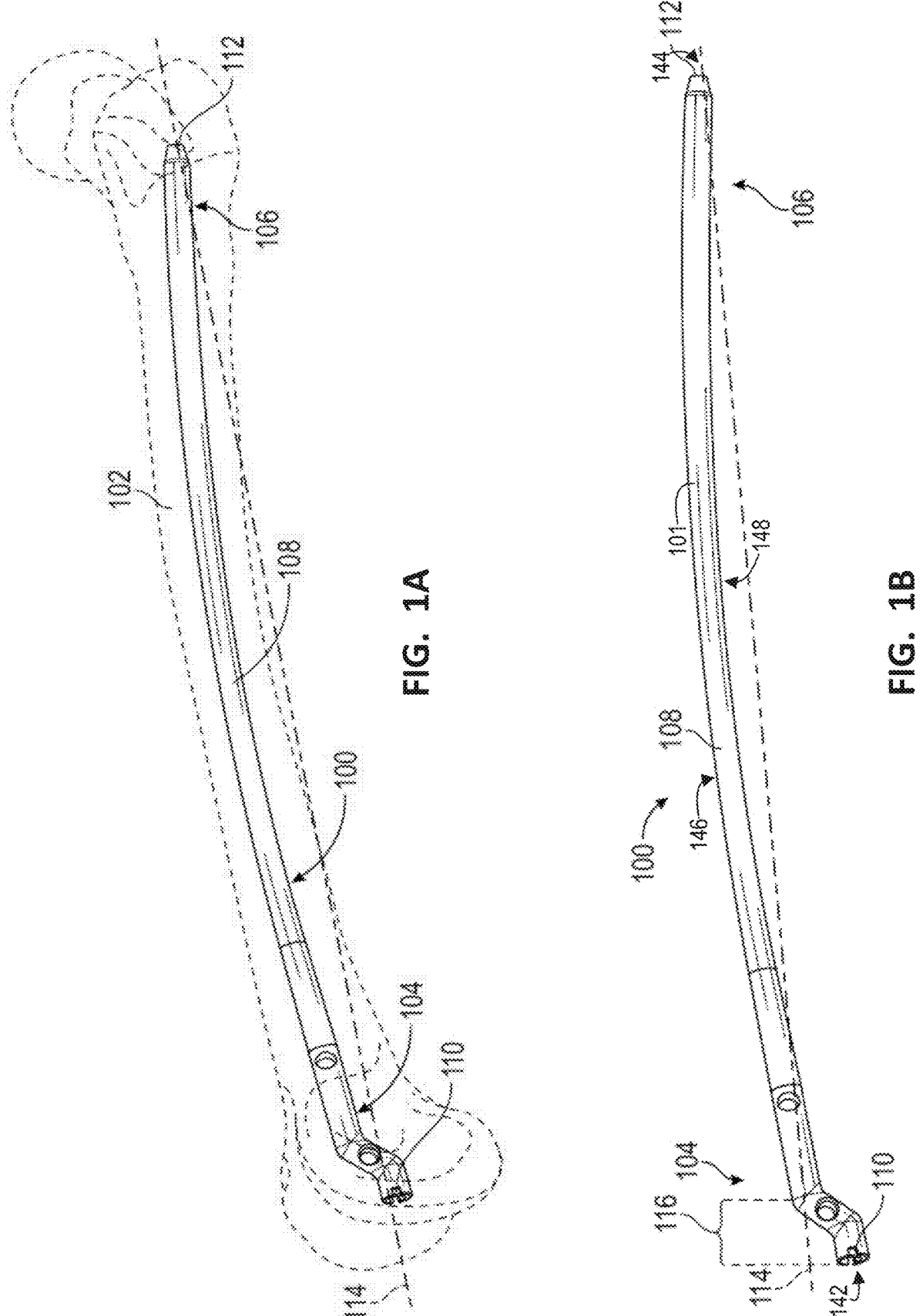
FIG. 1A is a perspective view of an intramedullary nail within a long bone, according to one embodiment.
FIG. 1B is a perspective side view of the intramedullary nail of FIG. 1A, according to one embodiment.

Exemplary embodiments of the disclosure will be best understood by reference to the drawings, wherein like parts are designated by like numerals throughout. It will be readily understood that the components, as generally described and illustrated in the figures herein, could be arranged and designed in a wide variety of different configurations. Thus, the following more detailed description of the embodiments of the apparatus, system, and method is not intended to limit the scope of the invention, as claimed, but is merely representative of exemplary embodiments of the technology.

Standard medical planes of reference and descriptive terminology are employed in this disclosure. While these terms are commonly used to refer to the human body, certain terms are applicable to physical objects in general.

A standard system of three mutually perpendicular reference planes is employed. A sagittal plane divides a body into right and left portions. A coronal plane divides a body into anterior and posterior portions. A transverse plane divides a body into superior and inferior portions. A mid-sagittal, mid-coronal, or mid-transverse plane divides a body into equal portions, which may be bilaterally symmetric. The intersection of the sagittal and coronal planes defines a superior-inferior or cephalad-caudal axis. The intersection of the sagittal and transverse planes defines an anterior-posterior axis. The intersection of the coronal and transverse planes defines a medial-lateral axis. The superior-inferior or cephalad-caudal axis, the anterior-posterior axis, and the medial-lateral axis are mutually perpendicular.

Anterior means toward the front of a body. Posterior means toward the back of a body. Superior or cephalad means toward the head. Inferior or caudal means toward the feet or tail. Medial means toward the midline of a body, particularly toward a plane of bilateral symmetry of the body. Lateral means away from the midline of a body or away from a plane of bilateral symmetry of the body. Axial means toward a central axis of a body. Abaxial means away from a central axis of a body. Ipsilateral means on the same side of the body. Contralateral means on the opposite side of the body from the side which has a particular condition or structure. Proximal means toward the trunk of the body. Proximal may also mean toward a user, viewer, or operator. Distal means away from the trunk. Distal may also mean away from a user, viewer, or operator. Dorsal means toward the top of the foot or other body structure. Plantar means toward the sole of the foot or toward the bottom of the body structure. Antegrade means forward moving from a proximal location/position to a distal location/position or moving in a forward direction. Retrograde means backward moving from a distal location/position to a proximal location/position or moving in a backwards direction. Sagittal refers to a midline of a patient's anatomy, which divides the body into left or right halves. The sagittal plane may be in the center of the body, splitting it into two halves. Prone means a body of a person lying face down. Supine means a body of a person lying face up.

The present disclosure discloses surgical devices, systems, and/or methods for fixation in relation to fractures of a long bone of a patient. Existing fixators and/or fixation devices, methods, or steps for long bone fractures are limited.

In patients who have received a joint prosthesis at a joint at the distal end of a long bone, existing intramedullary fasteners, such as nails, rods, and the like can make retrograde and antegrade deployment from a distal/proximal end of the long bone challenging or not possible using conventional techniques and instrumentation. A simple, easy intramedullary fastener or intramedullary fastener system or intramedullary fastener assembly that facilitates retrograde/antegrade deployment from a distal/proximal end of the long bone is needed.

FIG. 1A illustrates an example of a fixation device according to one embodiment of the present disclosure. In one embodiment, the fixation device may comprise an intramedullary nail assembly. The intramedullary nail assembly 100 is illustrated deployed within a long bone, such as a femur 102. The intramedullary nail assembly 100 may include an intramedullary nail 101. The illustrated intramedullary nail assembly 100 is one example of an intramedullary nail assembly that may be used in accordance with the present disclosure.

"Intramedullary nail" refers to a fastener designed, configured, engineered, and/or adapted to be deployed within an intramedullary cavity or canal of a patient. An intramedullary nail can be rigid or flexible, modular, a single unitary piece, part of a system, and/or part of an assembly. An intramedullary nail may be formed of any biocompatible materials, including but not limited to biocompatible metals such as Titanium, Titanium alloys, stainless steel alloys, cobalt-chromium steel alloys, nickel-titanium alloys, shape memory alloys such as Nitinol, biocompatible ceramics, and biocompatible polymers such as Polyether ether ketone (PEEK) or a polylactide polymer (e.g. PLLA) and/or others.

"Femur", "femurs", "femora", or "thigh bone" refers to a long bone in the body of a patient (e.g., human or animal). The femur is the proximal bone of the hindlimb in tetrapod vertebrates. The head of the femur articulates with the acetabulum in the pelvic bone forming the hip joint, while the distal part of the femur articulates with the tibia (shinbone) and patella (kneecap), forming the knee joint. By most measures the two (left and right) femurs are the strongest bones of the body, and in humans, the largest and thickest. The femur is categorized as a long bone and comprises a diaphysis (shaft or body) and two epiphyses (extremities) that articulate with adjacent bones in the hip and knee. The femur includes an upper part (proximal part), body, and a lower part (distal part). The upper part includes the head, neck, the two trochanters and adjacent structures. The body of the femur (or shaft) is large, thick and almost cylindrical in form. The lower part or lower extremity of the femur (or distal extremity) is the thickest femoral extremity, the upper extremity (upper part) is the shortest femoral extremity. The lower part is somewhat cuboid in form, but its transverse diameter is greater than its antero-posterior (front to back). The lower part includes two oblong eminences known as the condyles. (Search 'femur' on Wikipedia.com May 20, 2022. Modified. Accessed Aug. 1, 2022.)

As used herein, a "lateral condyle" refers to one of the two projections on the lower extremity, distal end, of the femur. The other one is the medial condyle. The lateral condyle is prominent and is broader both in its front-to-back and transverse diameters. (Search "lateral condyle" on Wikipedia.com Apr. 17, 2020. Modified. Accessed Jan. 6, 2020.) As used herein, a "medial condyle" refers to one of the two projections on the lower extremity, distal end, of femur, the other being the lateral condyle. The medial condyle is larger than the lateral (outer) condyle due to more weight bearing caused by the center of mass being medial to the knee. (Search "medial condyle" on Wikipedia.com May 12, 2020. Modified. Accessed Jan. 6, 2020.) "Epicondyle" refers to a rounded eminence on a bone that lies upon a condyle. Examples of epicondyles in humans include, but are not limited to, medial epicondyle of the femur, lateral epicondyle of the femur, medial epicondyle of the humerus, and lateral epicondyle of the humerus. (Search 'epicondyle' on Wikipedia.com Nov. 27, 2018. Modified. Accessed Aug. 1, 2022.)

The intramedullary nail assembly 100 may include a distal end 104, a proximal end 106, and a shaft 108. The distal end 104 may include a coupling 110 and the proximal end 106 may include a point 112. The intramedullary nail assembly 100 includes a longitudinal axis 114.

As used herein, "end" refers to a part or structure of an area or span that lies at the boundary or edge. An end can also refer to a point that marks the extent of something and/or a point where something ceases to exist. An end can also refer to an extreme or last part lengthwise of a structure or surface. (search "end" on Merriam-Webster.com. Merriam-Webster, 2021. Web. 4 Aug. 2021. Modified.) "Longitudinal axis" refers to an axis of a structure, device, object, apparatus, or part thereof that extends from one end of a longest dimension to an opposite end. Typically, a longitudinal axis passes through a center of the structure, device, object, apparatus, or part thereof along the longitudinal axis. The center point used for the longitudinal axis may be a geometric center point and/or a mass center point.

FIG. 1B is a perspective side view of the intramedullary nail assembly 100 of FIG. 1A, according to one embodiment. The intramedullary nail assembly 100 serves to provide weight bearing load, axial loading, bending load, torsional load, and structural support for the long bone (e.g., femur 102) of a patient. The intramedullary nail assembly 100 may be made from a variety of biocompatible materials used in intramedullary nails. The intramedullary nail assembly 100 may be hollow along its length. A passage through the intramedullary nail assembly 100 may permit deployment of the intramedullary nail assembly 100 along a guide wire. The intramedullary nail assembly 100 may have a longitudinal cross section that is circular, ovoid, polygonal, or the like. As used herein, "passage" refers to a duct, a vessel, an opening, a void, or other channel in a body of a an apparatus, instrument, structure, member, device, component, system, or assembly. In certain embodiments, a passage is narrow and longer than the passage is wide. (Search "passage" on wordhippo.com. WordHippo, 2021. Web. Accessed 15 Nov. 2021. Modified.)

The cross-sectional diameter and length of the intramedullary nail assembly 100 can vary depending on the age, gender, nature and position of long bone fracture(s) (e.g., diaphyseal, metaphyseal, periarticular, etc.), size of the patient, and the like. In certain embodiments, an intramedullary nail assembly 100 having about a 10 mm cross section can be used. The shaft 108 is a rigid structure that connects the distal end 104 and proximal end 106. The distal end 104 and proximal end 106 may each also be rigid. In certain embodiments, the shaft 108, distal end 104, and/or proximal end 106 may include some level of resilience. The amount of resilience in the shaft 108, distal end 104, and/or proximal end 106 may vary or may be consistent and may be engineered to facilitate deployment of the intramedullary nail assembly 100 within the medullary canal of the long bone.

The shaft 108 connects the distal end 104 and the proximal end 106. The length of the shaft 108 may determine the length of the intramedullary nail assembly 100. In certain embodiments, the shaft 108 include a curve or bow such that the intramedullary nail assembly 100 follows a natural curve in an intramedullary canal of a patient's long bone.

The shaft 108, distal end 104, and proximal end 106 may be manufactured from a single piece of material. In another embodiment, the shaft 108, distal end 104, the proximal end 106 may each or a combination of them be made from a single piece of material that is then connected, joined, or coupled to form the intramedullary nail assembly 100.

The proximal end 106 may include a point 112. The point 112 may comprise a tapered wall that has an increasing smaller diameter until the point 112 comes to a single point or defines a blunt end surface for the point 112. "Point" refers to a mechanical device, apparatus, member, component, system, assembly, or structure having a larger diameter on one end than the diameter on the opposite end. In certain embodiments, a point has a proximal end connected or coupled to a base, shaft, and/or body and a distal end that is free. A point may have a variety of cross-sectional shapes including round, circular, square, oval, rectangular, and the like. In certain embodiments, a point may progressively taper from a larger diameter on one end to a small sharp end on an opposite end. Alternatively, a free end of a point may have a flat or angled end instead of a sharp tip.

The point 112 serves to facilitate deployment of the intramedullary nail assembly 100 within the medullary cavity/canal. The point 112 can help guide the proximal end 106 through the medullary cavity/canal and can help move bone marrow aside as the intramedullary nail assembly 100 is deployed. In certain embodiments, the proximal end 106 may also include one or more openings (not shown) for accepting a fastener (e.g., a bone screw) used to lock the intramedullary nail assembly 100 in place, or fix the intramedullary nail assembly 100, in place within the long bone. The one or more openings may include internal threads that engage threads of a fastener or may permit the fastener to pass through the intramedullary nail assembly 100 and engage bone on an opposite side of the one or more openings.

"Thread" or "threads" refers to a helical structure used to convert between rotational and linear movement or force. A thread is a ridge wrapped around a cylinder or cone in the form of a helix, with the ridge wrapped around the cylinder being called a straight thread and the ridge wrapped around the cone called a tapered thread. Straight threads or tapered threads are examples of external threads, also referred to as male threads. Threads that a correspond to male threads are referred to as female threads and are formed within the inside wall of a matching hole, passage, or opening of a nut or substrate or other structure. A thread used with a fastener may be referred to as a screw thread and can be an important feature of a simple machine and also as a threaded fastener. The mechanical advantage of a threaded fastener depends on its lead, which is the linear distance the threaded fastener travels in one revolution. (Search 'screw thread' on Wikipedia.com Jul. 17, 2022. Modified. Accessed Aug. 1, 2022.)

The distal end 104 includes an offset section 116. The offset section 116 serves to interconnect a distal end of the distal end 104 (e.g., the coupling 110) to the remainder of the intramedullary nail assembly 100 (e.g., the shaft 108 of the intramedullary nail 101). The offset section 116 may have a variety of configurations, some examples of which are disclosed herein.

The offset section 116 redirects the distal end 104 posteriorly within a distal end of the long bone. For example, in a femur, the offset section 116 redirects the distal end 104 from a conventional entry point (i.e. one that may be used in patients without a distal joint prosthesis) that would be between the lateral condyle, medial condyle, and patellar surface to another entry point more posterior between the lateral condyle and medial condyle, such as for example, within the intercondylar fossa (e.g., the posterior intercondyloid fossa, also referred to as the femoral notch).

As used herein, "notch" refers to a depression in a bone which often, provides stabilization to an adjacent articulating bone. Examples of a notch, include but are not limited to, trochlear notch on the ulna; radial notch of the ulna; suprasternal notch; mandibular notch, and femoral notch on distal end of a femur. (Hartline, Rosanna, "7.6: Bone Markings", shared under a CC-BY-NC-SA license. Modified. Accessed Jul. 26, 2022 on this website https://bio.libretexts.org/). The offset section 116 combines two axes (longitudinal axis 114 and offset axis 122) such that these are offset relative to each other. The two axes are not aligned with each other.

Advantageously, the offset section 116 permits a surgeon to perform a retrograde deployment from a distal end of long bone at an entry point that is more posterior than may be used conventionally. Deploying an intramedullary nail assembly 100 at an entry point that is more posterior can be advantageous where a patient has received a total knee replacement (TKR) or partial knee replacement that includes a femoral component implant that blocks access to the medullary canal by way of an entry point more anterior between the lateral condyle and medial condyles (e.g., at the middle of the intercondylar sulcus). Advantageously, the section 116 can be designed to accommodate a variety of prosthesis that may be deployed with a patient. For example, the section 116 can be configured to account for prosthesis such as a joint or fixation prostheses, femoral component for a partial or total knee replacement (TKR) procedure, a femoral component for a total hip replacement, and/or to address a peri-implant fracture of a patient's bone. In certain embodiments, the prosthesis has been installed prior to a procedure to deploy the intramedullary nail assembly 100. For example, the offset section 116 may extend from the distal end 104 of the intramedullary nail 101. The section 116 may be configured to avoid interference with a prein-stalled femoral component of a knee joint implant.

Referring to FIGS. 1C and 1D, in one embodiment, the offset section 116 includes a first bend 118 and a second bend 120. The first bend 118 and second bend 120 may be described by how the bends are angled in relation to the longitudinal axis 114 of the intramedullary nail assembly 100. For example, in one embodiment, the first bend 118 is angled posteriorly from the longitudinal axis 114 when the intramedullary nail assembly 100 is deployed within along bone of a patient. The first bend 118 may define a first angle 126 between the longitudinal axis 114 and a body 128 of the offset section 116. The first angle 126 may be a variety of angles and may range from between about 3 degrees and about 90 degrees. In certain embodiments, the first angle 126 may be about 45 degrees.

In addition, the second bend 120 is angled anteriorly from, or in relation to, the longitudinal axis 114 when the intramedullary nail assembly 100 is deployed within a long bone of a patient. The second bend 120 may define a second angle 130 between the body 128 and an offset axis 122 (i.e., a longitudinal axis of the offset section 116). The second angle 130 may be a variety of angles and may range from between about 25 degrees and about 155 degrees. In certain embodiments, the second angle 130 may be about 135 degrees.

In one embodiment, the first angle 126 and second angle 130 may be supplementary angles such that joining the first bend 118 and second bend 120 together with the body 128 between them results in the coupling 110 extending in a direction or along an offset axis 122 that is parallel to the longitudinal axis 114. Said another way, the second bend 120 may be angled anteriorly from, or in relation to, the longitudinal axis 114 such that a coupling 110 connected to the second bend 120 extends, or is oriented, in a direction that is parallel to the longitudinal axis 114. An offset axis 122 that passes through a cross sectional center 124 of the coupling 110 and into the second bend 120 is substantially parallel to the longitudinal axis 114.

FIG. 1D illustrates an example first angle 126 and an example second angle 130 for one embodiment in relation to longitudinal axis 114. In one embodiment, the example first angle 126 of the first bend 118 is less than about 90 degrees and the second angle 130 of the second bend 120 is greater than about 90 degrees. In the illustrated embodiment, the first angle 126 and second angle 130 are supplementary angles. Of course, first angle 126 and second angle 130 may not be supplementary angles in other embodiments.

The length of the body 128 may vary depending on the type of long bone and/or type of fracture being treated. Similarly, the angle of the first bend 118 and/or second bend 120 can vary depending on the type of long bone and/or type of fracture being treated.

Alternatively, or in addition, the offset section 116 may include a single bend, such as first bend 118. In such an embodiment, the coupling 110 and an end of the distal end 104 extends posteriorly from a distal joint of the long bone.

The distal end 104 and/or the section 116 of the intramedullary nail assembly 100 may include one or more openings 132 configured to accept one or more fasteners (e.g., a bone screws) used to lock the intramedullary nail assembly 100 in place, or fix the intramedullary nail assembly 100, in place within the long bone. The one or more openings 132 may include internal threads that engage threads of fasteners or may permit the fasteners to pass through the intramedullary nail assembly 100 and engage bone on an opposite side of the one or more openings 132. One of the one or more openings 132 may be within the body 128 of the offset section 116 and one of the one or more openings 132 may be at another position along the distal end 104. The fastener openings 132 may be configured to accept fasteners driven into the long bone at a variety of angles. In certain embodi-ments, the one or more openings 132 may be positioned between the first bend 118 and the second bend 120. The openings 132 may accept a cross-fixation fastener config-ured to cooperate with the intramedullary nail 101 to provide torsional stiffness to the intramedullary nail assembly 100.

FIGS. 1E, and 1F, are a top view and bottom view respectively of the intramedullary nail of FIG. 1A, according to one embodiment. FIGS. 1G and 1H are a distal end view and a proximal end view respectively of the intramedullary nail of FIG. 1A, according to one embodiment. FIG. 1G illustrates the coupling 110 and a hollow passage 134 that may extend from the distal end 104 to the proximal end 106.

The coupling 110 of the distal end 104 serves to connect the intramedullary nail assembly 100 with a driver (See FIG. 3A) for deployment of the intramedullary nail assembly 100. The coupling 110 may use a variety of features and/or interfaces for making a coupling/connection between the coupling 110 and the driver. In the illustrated embodiment, the coupling 110 includes an arrangement of grooves 234 (See FIG. 2C) that accept ridges or "tongues" that may extend from a corresponding driver of an inserter. The grooves 234 engage the tongues to permit the driver to force, or move, the intramedullary nail assembly 100 longitudi-nally when deploying the intramedullary nail assembly 100. The grooves 234 permit some torque forces to be applied to the coupling 110 to facilitate deployment of the intramed-ullary nail assembly 100. In certain embodiments, the grooves 234 may engage with the tongues in a friction fit such that the intramedullary nail assembly 100 can be retracted as needed during a deployment procedure. In certain embodiments, the coupling 110 may engage with a driver such that retraction of the driver also retracts the coupling 110 and structures connected to the coupling 110.

FIG. 1H illustrates the point 112 having a tapered wall 136 that has an increasing smaller diameter until the point 112 comes to a single point within the hollow passage 134 on a blunt end surface 140.

Referring now to FIGS. 1B-1H, the intramedullary nail assembly 100 can include an inferior side 142, a superior side 144, an anterior side 146, and a posterior side 148 (See FIG. 1A).

As used herein, "side" refers to a structure or part of a structure including, but not limited to: one of a longer bounding surfaces or lines of an object especially contrasted with the ends, a line or surface forming a border or face of an object, either surface of a thin object, a bounding line or structure of a geometric figure or shape, and the like. (search "side" on Merriam-Webster.com. Merriam-Webster, 2021. Web. 3 Aug. 2021. Modified.) A side can also refer to a geometric edge of a polygon (two-dimensional shape) and/or a face or surface of a polyhedron (three-dimensional shape). (Search "side" on Wikipedia.com Jul. 21, 2021. CC-BY-SA 3.0 Modified. Accessed Aug. 3, 2021.) Side can also refer to a location on a structure. For example, a side can be a location on a structure at, or near, a furthest position away from a central axis of the structure.

As used herein, the term "side" can include one or more modifiers that define and/or orient and/or distinguish the side of an object from others based on based on where and/or how the object is deployed within or in relation to a second object. For example, in the context of an implant for a patient, sides of the implant may be labeled based on where the sides are relative to the patient when the implant is deployed. As one example, an "anterior side" of an implant refers to a side that is anterior to other sides of the implant in relation to a patient when the implant is deployed in the patient.

Referring still to FIGS. 1B-1H, the intramedullary nail assembly 100 can also include a medial side 150 and a lateral side 152 (See FIG. 1E). The medial side 150 may face a medial side of the patient and the lateral side 152 may face a lateral side of the patent when the intramedullary nail assembly 100 is deployed.

In one embodiment, the offset section 116 is proximal to the distal end 104 of the intramedullary nail assembly 100. As in other embodiments, the offset section 116 can include a first bend 118 and a second bend 120. Referring now to FIGS. 1C, 1D, and IE, the first bend 118 may extend from the anterior side 146 of the intramedullary nail 101 towards the posterior side 148 of the intramedullary nail 101. In addition, the second bend 120 may extend from the posterior side 148 of the intramedullary nail 101 to the anterior side 146 of the intramedullary nail 101. In this manner, the intramedullary nail assembly 100 may include two bends 118, 120.

In another embodiment, the first bend 118 may extend from the posterior side 148 of the intramedullary nail 101 towards the anterior side 146 of the intramedullary nail 101. In addition, the second bend 120 may extend from the anterior side 146 of the intramedullary nail 101 to the posterior side 148 of the intramedullary nail 101. In this manner too, the intramedullary nail assembly 100 may include two bends 118, 120.

In one embodiment, the first bend 118 is proximal to the distal end 104 and angled posteriorly in relation to the longitudinal axis 114. The second bend 120 can be positioned between the distal end 104 and the first bend 118. The second bend 120 is angled anteriorly in relation to the longitudinal axis 114. The body 128 extends between the first bend 118 and the second bend 120.

In one embodiment, the second bend 120 defines an offset axis 122. Advantageously in the illustrated embodiment, the second bend 120 can be configured such that the offset axis 122 extends from a distal end 104 of the intramedullary nail 101 substantially parallel to the longitudinal axis 114. In this manner, the a lateral force along the offset axis 122 is transferred to the longitudinal axis 114 by way of the body 128 of the section 116.

Those of skill in the art will appreciate that the first bend 118 and/or second bend 120 may be angled medially and/or laterally relative to the longitudinal axis 114 of the intramedullary nail 101.

Referring to FIGS. 1B, 1C, and 1D, the section 116 may have a particular shape when viewed from the medial side 150 and/or lateral side 152 of the intramedullary nail 101. In the illustrated embodiment, the first bend 118, body 128, and/or second bend 120 of the section 116 may form an "S" shape when viewed from the medial side 150 and/or lateral side 152 of the intramedullary nail 101. "S shape" refers to any mechanical device, apparatus, body, base, protrusion, member, component, system, assembly, or structure having a shape that resembles or mimics or conforms to or matches one or more attributes of a letter "S". In certain embodiments, ends of a structure that has an S shape may bend back and over a center of the S shape. In other embodiments, ends of a structure that has an S shape may extend from a center of the S shape and may include one or more bends and/or one or more curves, but the ends may not necessarily bend back and over a center of the S shape. Said another way, a structure may have an S shape and the bend sections of the S shape, (e.g., in a letter S) may not double back on themselves.

Figure 1I:
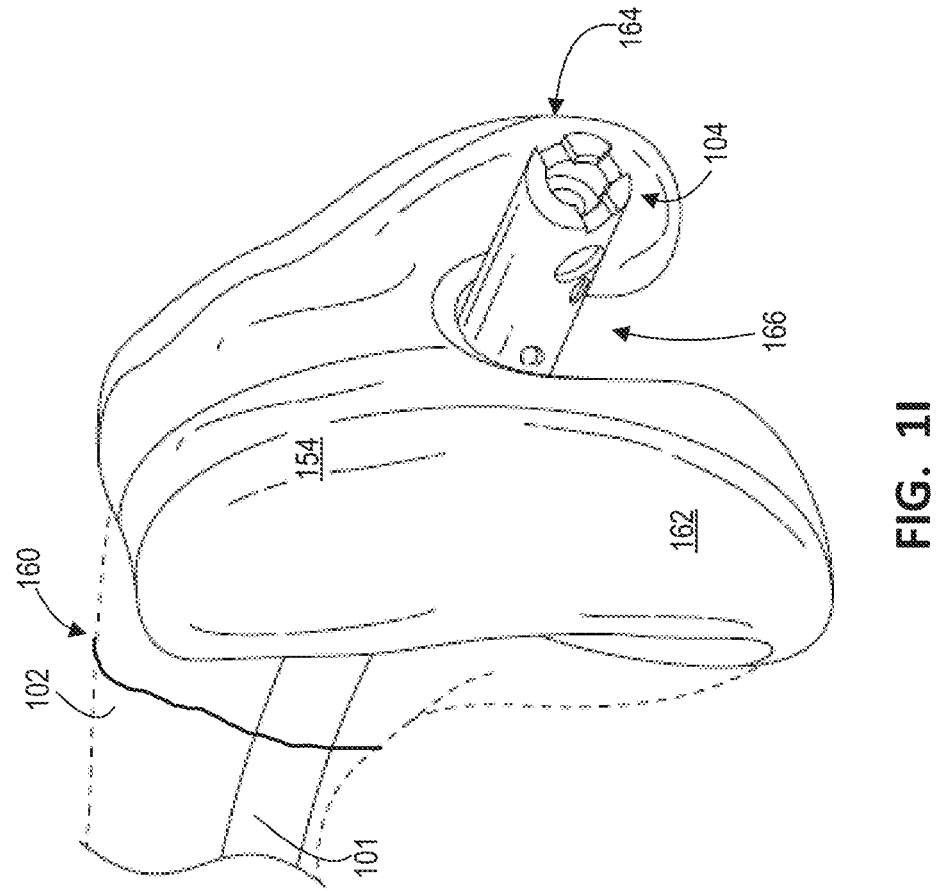
FIG. 1I is a perspective view of a distal end of a femur with an installed femoral component and the intramedullary nail of FIG. 1A.

FIG. 1I illustrates a perspective view of a distal end of a femur 102 with an installed femoral component 154 and the intramedullary nail 101 of FIG. 1A. The femoral component 154 can be part of a prosthesis system for a total or partial knee joint replacement.

The femur 102 includes a bone fracture 160. The femoral component 154 includes a medial condyle portion 162 that covers a portion of the medial condyle and a lateral condyle portion 164 that covers a portion of the lateral condyle of the femur 102.

"Bone fracture" refers to a medical condition in which there is a partial or complete break in the continuity of a bone. The bone may be broken into one or more pieces. (Search "bone fracture" on Wikipedia.com Apr. 21, 2022. CC-BY-SA 3.0 Modified. Accessed Jun. 10, 2022.) Bone fractures can be of one or more types. The name and/or type of fracture can be based on the specific bone involved, the condition of the bone due to the fracture, the type of bone, among other factors. Bone fractures may be closed/simple fractures or open/compound fractures. Bone fractures may be described as non-displaced or displaced. Bone fractures have a specific pattern such as a linear fracture, a transverse fracture, an oblique fracture, a spiral fracture, a compression/wedge fracture, an impacted fracture, and an avulsion fracture. Bone fractures may be incomplete fractures, complete fractures, and comminuted fractures. Bone fractures of bones in the foot may be referred to as a lisfranc fracture (one or more metatarsals displaced from the tarsus), jones fracture (fracture of the proximal end of the 5th metatarsal), pseudo-jones fracture (fracture of the proximal end of the 5th metatarsal that includes an articular surface of the base of the 5th metatarsal), march fracture (fracture of the distal third of a metatarsal), cuneiform fracture (fracture of one of the cuneiform bones), calcaneal fracture (fracture of the calcaneus). (Search "bone fracture" on Wikipedia.com Apr. 21, 2022. CC-BY-SA 3.0 Modified. Accessed Jun. 10, 2022.)

The intramedullary nail assembly 100 is in the process of being deployed within the intramedullary canal of the patient. The section 116 includes a first end proximal to the first bend 118 and a second end (e.g., distal end 104) proximal to the second bend 120. The section 116 has a diameter sized to fit within the femoral notch 166. In one embodiment, the section 116 may have a diameter of about 11.2 mm. In one embodiment, the femoral notch 166 serves as the entry point for the intramedullary nail assembly 100 (e.g., the intramedullary nail 101). As the intramedullary nail assembly 100 advances retrograde into the intramedullary canal, the shaft 108 moves along a shaft of the femur 102 and the offset section 116 moves into a curved area near the distal end of the intramedullary canal. In one embodiment, the distal end 104 can extend into the femoral notch 166 when the intramedullary nail assembly 100 is deployed.

Advantageously, the section 116 of the intramedullary nail assembly 100 positions the distal end 104 within the femoral notch and avoids interference between the intramedullary nail assembly 100 and the femoral component 154.

Suppose the bone fracture 160 is such that the distal end of the femur 102 is in extension. Thus, for a desired reduction, the femur 102 should be in flexion about the bone fracture 160. Advantageously, the present disclosure contacts the femur within the intramedullary canal and moves the distal end of the femur 102 into flexion rather than extension to facilitate reduction. The offset section 116 can contact an anterior wall (anterior cortex of femur 102) of the intramedullary canal and thereby press the distal end of the femur anteriorly. This anterior contact and/or pressure can assist in the reduction of the femur 102.

In certain embodiments, an anterior surface of the offset section 116 can contact the femoral notch 166 and thereby apply pressure to facilitate a reduction for the femur 102. "Interference" refers to an action by an object, person, animal, plant, or structure that impedes, blocks, interrupts, stops, and/or prevents the operation, movement, function, and/or deployment of another object, person, animal, plant, or structure.

As used herein, "flexion" refers to the act of bending a joint, especially a bone joint, or two bone segments. The counteraction of extension. (Search "flexion" on wordhippo.com. WordHippo, 2021. Web. Accessed 8 Dec. 2021. Modified.) Flexion may include the act of moving parts of a joint from an unflexed or extended state to a nonextended or flexed state and may be expressed in terms of degrees of the flexion and/or extension. The range of degrees available to express the state of extension and/or flexion may depend on the range of motion for a particular joint. As used herein, "extension" refers to the act of unbending a joint, especially a bone joint, or two bone segments. The counteraction of flexion. (Search "flexion" on wordhippo.com. WordHippo, 2021. Web. Accessed 8 Dec. 2021. Modified.) Extension may include the act of moving parts of a joint from a flexed state to an extended state and may be expressed in terms of degrees of the extension and/or flexion. The range of degrees available to express the state of extension and/or flexion may depend on the range of motion for a particular joint.

FIGS. 1A-1I illustrate an embodiment that incorporates the offset section 116 into a single implant (e.g., intramedullary nail assembly 100) that can be deployed in the intramedullary canal of a patient. In particular, the offset section 116 enables retrograde deployment from the distal end of the long bone where the long bone includes an arthroplasty implant at a distal end of the long bone. Of course other alternative embodiments of an offset section 116 are within the scope of the present disclosure. In certain embodiments, the intramedullary nail assembly 100 may include a single intramedullary nail shaped, designed, or configured to include an offset section 116 formed as part of the intramedullary nail. Alternatively, or in addition, the intramedullary nail assembly 100 includes an adapter and/or an inserter that includes the offset section 116. FIGS. 2A-2G illustrate one alternative embodiment. The offset section 116 can be offset in terms of an anterior/posterior direction/axis. Alternatively, or in addition, the offset section 116 can be offset in terms of a medial/lateral direction/axis.

Figures 2A, 2B:
FIG. 2A is a perspective view of an intramedullary nail connected to an adapter within a long bone, according to one embodiment.
FIG. 2B is a perspective side view of the intramedullary nail and adapter of FIG. 2A, according to one embodiment.

FIG. 2A is a perspective view of an intramedullary nail system 200 that includes an intramedullary nail 202 connected to an adapter 204 within a long bone, such as a femur 102, according to one embodiment. The adapter 204 may serve one or more similar features, functions, and/or aspects as an offset section 116 in the intramedullary nail assembly 100. In one embodiment, the offset section 116 includes the adapter 204 and the adapter 204 is configured to connect to the distal end 208 of the intramedullary nail 202.

FIG. 2B is a perspective view of the intramedullary nail 202 and adapter 204 of FIG. 2A, according to one embodiment. The intramedullary nail 202 may include a proximal end 206, a distal end 208, and a shaft 210 between them. The shaft 210 may include a longitudinal axis 212. The intramedullary nail 202 may be a straight rigid intramedullary nail and/or may include a bow that follows a natural curve of the long bone of a patient. The intramedullary nail 202 may be similar to the intramedullary nail 101 of the intramedullary nail assembly 100 described above, except that the distal end 208 does not include an offset section 116. The intramedullary nail 202 may include one or more openings 214 similar in placement, function, and operation to the one or more openings 132 described above in relation to the intramedullary nail assembly 100.

The distal end 208 may include a first coupling 216 for coupling the intramedullary nail 202 to the adapter 204. The first coupling 216 is configured and/or arranged to engage with the adapter 204. The first coupling 216 enables longitudinal forces and/or torsional forces placed on the adapter 204 to transfer to the distal end 208 for deployment of the intramedullary nail 202.

The adapter 204 includes a second coupling 218, a third coupling 220, and a body 222. The second coupling 218 is configured to engage the first coupling 216. The third coupling 220 is configured to engage a fourth coupling of an inserter (See FIG. 3A). The body 222 may include a first bend 224 at one end and a second bend 226 at an opposite end. The first bend 224 sits between the second coupling 218 and the body 222 and directs the body 222 posteriorly in relation to the second coupling 218 and the longitudinal axis 212 of the intramedullary nail 202. The second bend 226 sits between the body 222 and the third coupling 220 and directs the body 222 posteriorly in relation to the third coupling 220 and the longitudinal axis 212 of the intramedullary nail 202. In certain embodiments, the second bend 226 directs the third coupling 220 such that the third coupling 220 extends from the body 222 parallel to the longitudinal axis 212. In one embodiment, the first bend 224 is angled posteriorly from the longitudinal axis 212 and the second bend 226 is angled anteriorly from the longitudinal axis 212 such that the third coupling 220 extends parallel to the longitudinal axis 212.

Referring to FIG. 1B and FIG. 2B, in certain embodiments, the intramedullary nail assembly 100 and/or intramedullary nail 202 may include a nail cap that connects to the coupling 110 and/or third coupling 220 once the intramedullary nail assembly 100 and/or intramedullary nail 202 is deployed. The nail cap may facilitate closing the entry point used to deploy the intramedullary nail assembly 100 and/or intramedullary nail 202. In certain embodiments, the adapter 204 may serve as a nail cap for the intramedullary nail 202.

Those of skill in the art will recognize that the intramedullary nail adapter 204 and adapter 204 can be adapted to engage a first coupling 216 at a proximal end 206 and/or the distal end 208. Alternatively, or in addition, the intramedullary nail assembly 100 can be manufactured with the section 116 on either or both the proximal end 106 and/or the distal end 104. In this manner the benefits of an offset section 116 can be gained on either end of the intramedullary nail assembly 100 or intramedullary nail 202 or on both ends.

FIG. 2C is a perspective view of the adapter 204 of FIG. 2A, according to one embodiment. FIG. 2C shows the second coupling 218, third coupling 220, and body 222 in more detail. In certain embodiments, the second coupling 218, third coupling 220, and body 222 have a circular longitudinal cross section. Other shaped longitudinal cross sections can also be used.

As described above in relation to the offset section 116, the adapter 204 may include a hollow passage 228 that extends from the second coupling 218 to the third coupling 220 that may be used for deployment of the adapter 204 over a guide wire. Generally, the hollow passage 228 has a common diameter throughout the adapter 204 and may have a diameter that matches the diameter of a corresponding passage within the intramedullary nail 202. The length of second coupling 218, third coupling 220, and body 222 may vary depending on the amount of offset needed to clear a deployed arthroplasty implant, age, gender, size, and anatomical structure of a patient.

In one embodiment, the intramedullary nail system 200 may include a distal coupling (e.g., third coupling 220) connected to the second bend 226. The third coupling 220 may be configured to engage and/or connect and/or couple to an inserter (See FIGS. 3B, 3C). In one embodiment, the first bend 224 is connected to the shaft 210. In the illustrated embodiment, the second coupling 218 may connect the first bend 224 and the shaft 210, the second coupling 218 may be referred to as a proximal coupling. The first bend 224, body 222, and second bend 226 can be preoperatively coupled to the shaft 210 near the first bend 224. In one embodiment, the second coupling 218 can couple the first bend 224 to the shaft 210 by way of a friction fit, latch, clip, interference fit, magnetic fit (magnet and magnetic material at opposite ends), or the like.

FIGS. 2D, 2E, 2F, and 2G are a distal end view, a proximal end view, a side view, and a side cross-section view respectively of the adapter of FIG. 2C, according to one embodiment. The adapter 204 has a distal end 230 and a proximal end 232. The first coupling 216 of the intramedullary nail 202 and the second coupling 218 and third coupling 220 of the adapter 204 serve to connect the intramedullary nail 202 with a driver (See FIG. 3A) for deployment/retraction of the intramedullary nail 202.

The first coupling 216 may use a variety of features and/or interfaces for making a coupling/connection between the multiple couplings and the driver. In the illustrated embodiment, the couplings 216, 218, 220 may each include an arrangement of one or more grooves 234 that accept one or more "tongues" or tabs 236 that may extend from another coupling 216, 218, 220 or driver of an inserter. The one or more grooves 234 may engage the one or more "tongues" or tabs 236 to permit the driver to force or move the intramedullary nail 202 longitudinally when deploying the intramedullary nail 202. The one or more grooves 234 may permit some torque forces to be applied to the couplings 216, 218, 220 to facilitate deployment of the intramedullary nail 202. In certain embodiments, the one or more grooves 234 may engage with the one or more "tongues" or tabs 236 in a friction fit such that the intramedullary nail 202 can be retracted as needed during a deployment procedure. In certain embodiments, the couplings 216, 218, 220 may engage each other and a driver such that retraction of the driver also retracts the couplings 216, 218, 220 and structures connected to the couplings 216, 218, 220. As used herein, "tab" refers to structure that extends or projects from another larger structure. A tab can be short and wide or long and thin. Typically, a tab is rigid and can include a degree of flexibility. Examples of a tab include a small flap or loop by which something may be grasped or pulled, a long thin projection that extends in one direction, a projection from a card or sheet, or the like. In certain embodiments, a tab can be an appendage or extension to another structure. (search "tab" on Merriam-Webster.com. Merriam-Webster, 2021. Web. 27 Jul. 2021. Modified.)

Those of skill in the art will recognize that the features, functions, and advantages of the offset section 116 can be integrated into an intramedullary nail such as intramedullary nail assembly 100, can be integrated into an adapter 204 such as the adapter 204 used with the example intramedullary nail 202 described above, can be integrated into an inserter used to insert an intramedullary nail into an intramedullary canal of a patient, or can be implemented in whole, or in part, in both the intramedullary nail and/or an adapter or an inserter. For example, in one embodiment, an adapter, or driver of an inserter, may include a second bend angled anteriorly from a longitudinal axis the intramedullary nail and a distal end of an intramedullary nail may include a first bend angled posteriorly from a longitudinal axis the intramedullary nail, with a suitable coupling between the first bend and the second bend. Each of these embodiments and other variations thereof are considered within the scope of the present disclosure.

Those of skill in the art will also recognize that the features, functions, and advantages of the offset section 116 are not limited to one or more bends in an anterior and/or posterior direction and can be used for prostheses, adapters, and/or instruments to provide one or more offset sections 116 that bend in other directions, including, but not limited to, medial/lateral, anterior/posterior, superior/inferior, cephalad/caudal, and the like. The offset section 116 enables use of prostheses in procedures to avoid existing tissue or structures that a surgeon desires to not disturb.

In certain embodiments, various names and/or labels may be used for the section 116 and/or an adapter 204 used with embodiments of the present disclosure. For example, the section 116 may also be referred to as an offset section, a detour section, a routing section, a rerouting section, an "S shaped" section, or the like. Alternatively, or in addition, the section 116 may be referred to as an accessibility section or accommodation section because the section enables an operator to access the medullary cavity when an arthroplasty implant is deployed or because the section accommodates deployment of an intramedullary nail even when an arthroplasty implant is deployed. Alternatively, or in addition, the adapter 204 (or inserter driver) may also be referred to as an offset adapter, a detour adapter, a routing adapter, a rerouting adapter, an "S shaped" adapter, or the like. Alternatively, or in addition, the adapter 204 may be referred to as an accessibility adapter or accommodation adapter because the adapter enables an operator to access the medullary cavity when an arthroplasty implant is deployed or because the adapter accommodates deployment of an intramedullary nail even when an arthroplasty implant is deployed.

The intramedullary nail assembly 100, offset section 116, intramedullary nail 202, and/or adapter 204 may be made from a variety of materials. In one embodiment, the materials used have sufficient flexibility to enable the intramedullary nail assembly 100 or intramedullary nail system 200 to be deployed into the intramedullary canal either retrograde or antegrade. For example, in one embodiment, intramedullary nail assembly 100, offset section 116, intramedullary nail 202, and/or adapter 204 may be made from a shape memory alloys such as Nitinol. Accordingly, such components may bend during deployment and then return to an original shape after deployment.

Figures 3A, 3B:
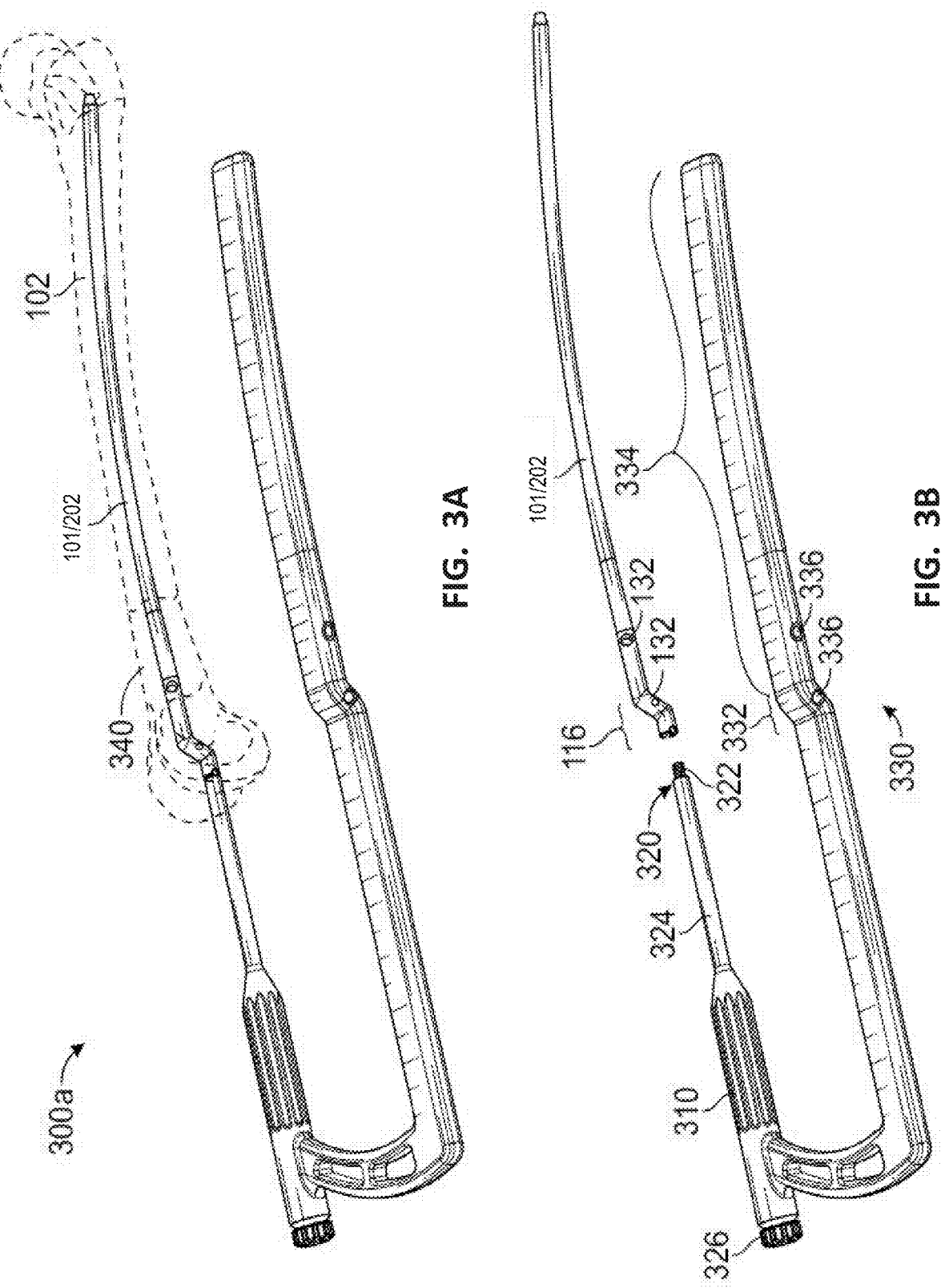
FIG. 3A is a perspective view of an inserter connected to one of the intramedullary nail of FIG. 1A or the intramedullary nail and adapter of FIG. 2A deployed within a long bone, according to one embodiment.
FIG. 3B is a perspective view of an inserter and one of the intramedullary nail of FIG. 1A and/or the intramedullary nail system of FIG. 2A, according to one embodiment.

FIG. 3A is a perspective view of an inserter 300a connected to one of the intramedullary nail assembly 100 of FIG. 1A or the intramedullary nail 202 and adapter 204 of FIG. 2A deployed within a long bone, such as a femur 102, according to one embodiment. The inserter 300a is a tool or instrument that enables and/or facilitates deployment and/or retraction of the intramedullary nail assembly 100, intramedullary nail system 200 (e.g., intramedullary nail 202 and adapter 204), and/or an intramedullary nail 202. As used herein, an "inserter" refers to an apparatus, instrument, structure, device, component, system, or assembly that is structured, organized, configured, designed, arranged, or engineered to insert or deploy one or more components, parts, or devices. In certain embodiments, an inserter can be used to insert implants and/or prosthesis into tissue, organs, or parts of a patient. In certain embodiments, an inserter can also be used to extract, retract, reposition, or remove an implant and/or prosthesis.

FIG. 3B is a perspective view of an inserter 300a and one of the intramedullary nail of FIG. 1A and/or the intramedullary nail system of FIG. 2A, according to one embodiment. The inserter 300a is disconnected from the intramedullary nail of FIG. 1A and/or the intramedullary nail system of FIG. 2A. The inserter 300a may include a handle 310, a driver 320, and an intramedullary nail guide 330.

The handle 310 is used by an operator to manipulate the intramedullary nail assembly 100 or intramedullary nail system 200 during deployment or retraction. The driver 320 can include external threads that engage with internal threads of a coupling 110/third coupling 220 to secure the driver 320 to the coupling 110/third coupling 220. Alternatively, the driver 320 can include a different engagement feature such as a friction fit, tabs, grooves, etc. for connecting to the coupling 110/third coupling 220 for the deployment or for a retraction.

In one embodiment, the driver 320 includes a threaded distal end 322, a shaft 324, and a thumb-screw 326. The threaded distal end 322, shaft 324, and thumb-screw 326 can be used to connect the driver 320 to the coupling 110/third coupling 220. The thumb-screw 326 is connected to the shaft 324 such that rotation of the thumb-screw 326 about the longitudinal axis of the shaft 324 turns the threaded distal end 322 to engage or disengage with the coupling 110/third coupling 220. The thumb-screw 326 can be rotated by an operator.

In the illustrated embodiment, the driver 320 includes a straight shaft 324 and straight driver 320. However, as described above, different features of the section 116 and/or adapter 204 may be coupled, connected, or integrated into the driver 320 of the inserter 300a. For example, the distal end 322 may include an adapter 204 with two bends 224, 226 as described above that engage a first coupling 216 of an intramedullary nail 202. In another example, the distal end 322 may include a bend such as second bend 226 and an adapter 204 or an intramedullary nail 202 may include a first bend 224. Such variations on the position and location of the bends 118/120/224/226 between the driver 320, an adapter 204, and an intramedullary nail 202/100 are within the scope of this present disclosure.

The intramedullary nail guide 330 provides a visual indicator for a surgeon or other user regarding where features of an intramedullary nail assembly 100 or intramedullary nail system 200 are physically during deployment or retraction. In one embodiment, the intramedullary nail guide 330 includes a section 332 and a shaft 334. The section 332 and shaft 334 may extend from the inserter 300a parallel to, and aligned with, the section 116 and shaft 108/210 of the intramedullary nail assembly 100, intramedullary nail system 200, or intramedullary nail 202 when an intramedullary nail is coupled to the inserter 300a,b. Similarly, the section 332 and shaft 334 may include openings 336 (such as fastener openings) positioned in alignment with openings 132 of the intramedullary nail assembly 100 or intramedullary nail system 200. In this manner, a surgeon can visually see the progression and position of the intramedullary nail assembly 100 or intramedullary nail system 200 and/or adapter 204 within the patient during a deployment or retraction.

Referring now to FIG. 3A, the intramedullary nail assembly 100 or intramedullary nail system 200 facilitates retrograde deployment of an intramedullary nail for patients who already have an arthroplasty implant. Suppose a patient has suffered a fracture 340 near the distal metaphysis of the femur 102. Patients who have received an implant in an arthroplasty procedure may have a greater risk of periprosthetic fractures (e.g., fracture 340).

Suppose further that a surgeon has decided to use the intramedullary nail assembly 100 or intramedullary nail system 200 for fixation of the femur 102. The surgeon may reduce the parts of the femur 102 around the fracture 340 using either an open reduction or a closed reduction. Next, a surgeon may create an entry point posterior to the medial and lateral condyles of the femur 102, within the intercondylar fossa. Advantageously, the entry point is posterior to an arthroplasty implant of the patient. Next, a surgeon may ream an opening to connect the entry point through the soft tissue to the intramedullary cavity. In one embodiment, the reamed opening may connect to the intramedullary cavity at about the same angle as the first bend 118 in relation to the longitudinal axis 114.

Following reaming, a surgeon may use the inserter 300a to deploy the intramedullary nail assembly 100 or intramedullary nail system 200 by passing the nail through the entry point and reamed opening and into the intramedullary cavity. The proximal end 106 of the intramedullary nail may fit tight as it passes through the reamed opening and into the intramedullary cavity. However, once the nail slides more distally into the intramedullary cavity the section 116 reaches the reamed opening and intramedullary cavity at which point pressure and stress on the nail being deployed is relieved and the nail fits snuggly within the femur 102 with the section 116 positioned as illustrated in FIG. 3A.

In certain instances, the fracture 340 displacement and/or angulation may be so great that femur fragments can be moved a great degree relative to each other. In such instances, the pressure on the intramedullary nail during deployment is minimal since the fragments can be positioned during intramedullary nail deployment and reduced to proper alignment, position, and angulation after the deployment.

Figure 3C:
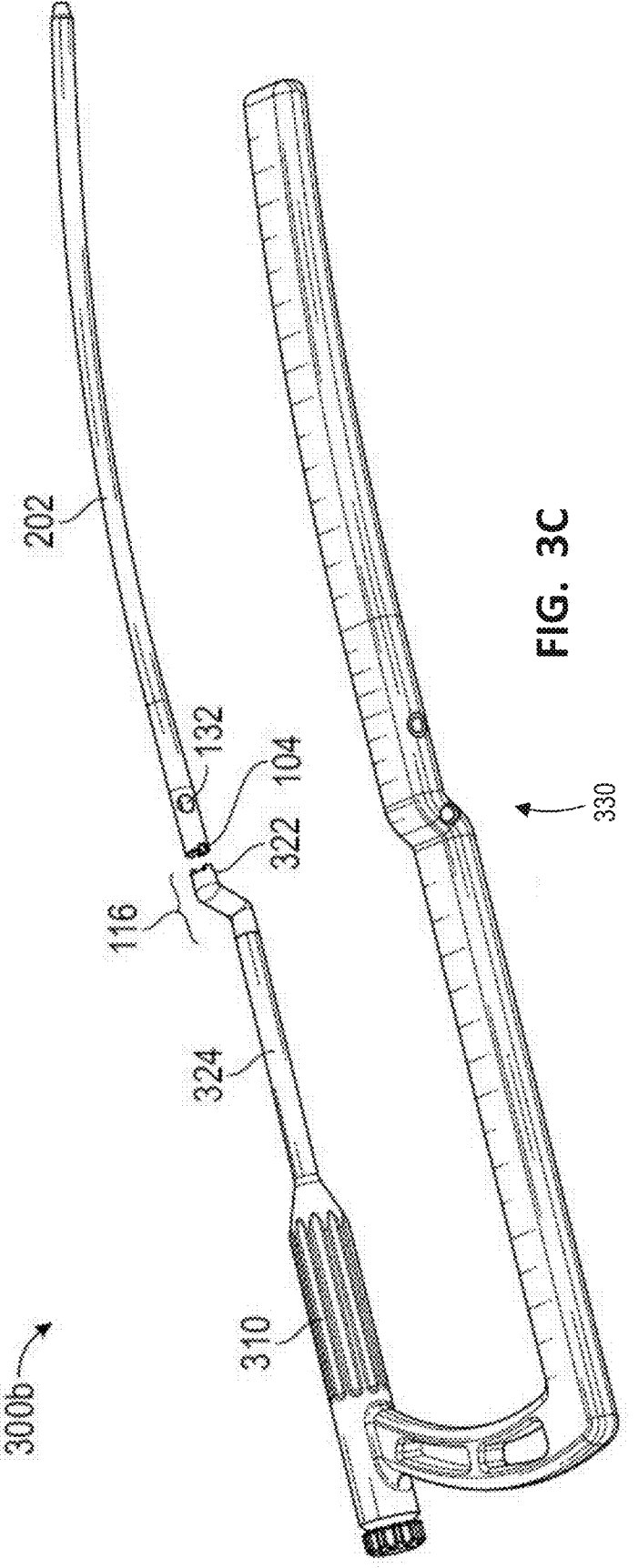
FIG. 3C is a perspective view of an inserter 300b and the intramedullary nail system of FIG. 2A, according to one embodiment.

FIG. 3C is a perspective view of an inserter 300b and the intramedullary nail system of FIG. 2A, according to one embodiment. The inserter 300b is disconnected from the intramedullary nail of FIG. 1A and/or the intramedullary nail system of FIG. 2A. The inserter 300b may include a handle 310, a driver 320, and an intramedullary nail guide 330 similar to those discussed in relation to inserter 300a.

The inserter 300b differs from inserter 300a in that the distal end 322 of inserter 300b, in the illustrated embodiment, includes an offset section 116. In one embodiment, the distal end 104 of the intramedullary nail 202 includes a coupling configured to engage the intramedullary nail 202 and the distal end 104/208. In the illustrated embodiment, the intramedullary nail 202 is straight and does not include an offset section 116. Instead, in the illustrated embodiment, the first bend 224, body 222, and/or second bend 226 may be integrated into the inserter 300b. Specifically, the first bend 224, body 222, and/or second bend 226 are integrated into a distal end of the inserter 300b.

The intramedullary nail assembly 100 or intramedullary nail system 200 may be used as primary fixation or secondary/supplemental fixation together with other fixation devices/techniques for fixation regardless of a position of a fracture (i.e., mid, distal, proximal sections of a long bone). Similarly, the intramedullary nail assembly 100 or intramedullary nail system 200 can be used in relation to any type of fracture on any type of long bone, such as a femur, humerus, and/or tibia and from either end (antegrade or retrograde). In addition, the intramedullary nail assembly 100 or intramedullary nail system 200 may be used for deployment of an antegrade intramedullary nail or a retrograde intramedullary nail.

In certain embodiments, the intramedullary nail assembly 100 and/or intramedullary nail system 200 can be deployed on a long bone that includes a prosthesis such as a knee prosthesis, a hip prosthesis, and/or one or more fixation prosthesis. Alternatively, or in addition, the intramedullary nail assembly 100 and/or intramedullary nail system 200 can be deployed on a long bone that has no prosthesis (i.e., a native long bone, no joint or fixation prostheses).

Figure 3D:
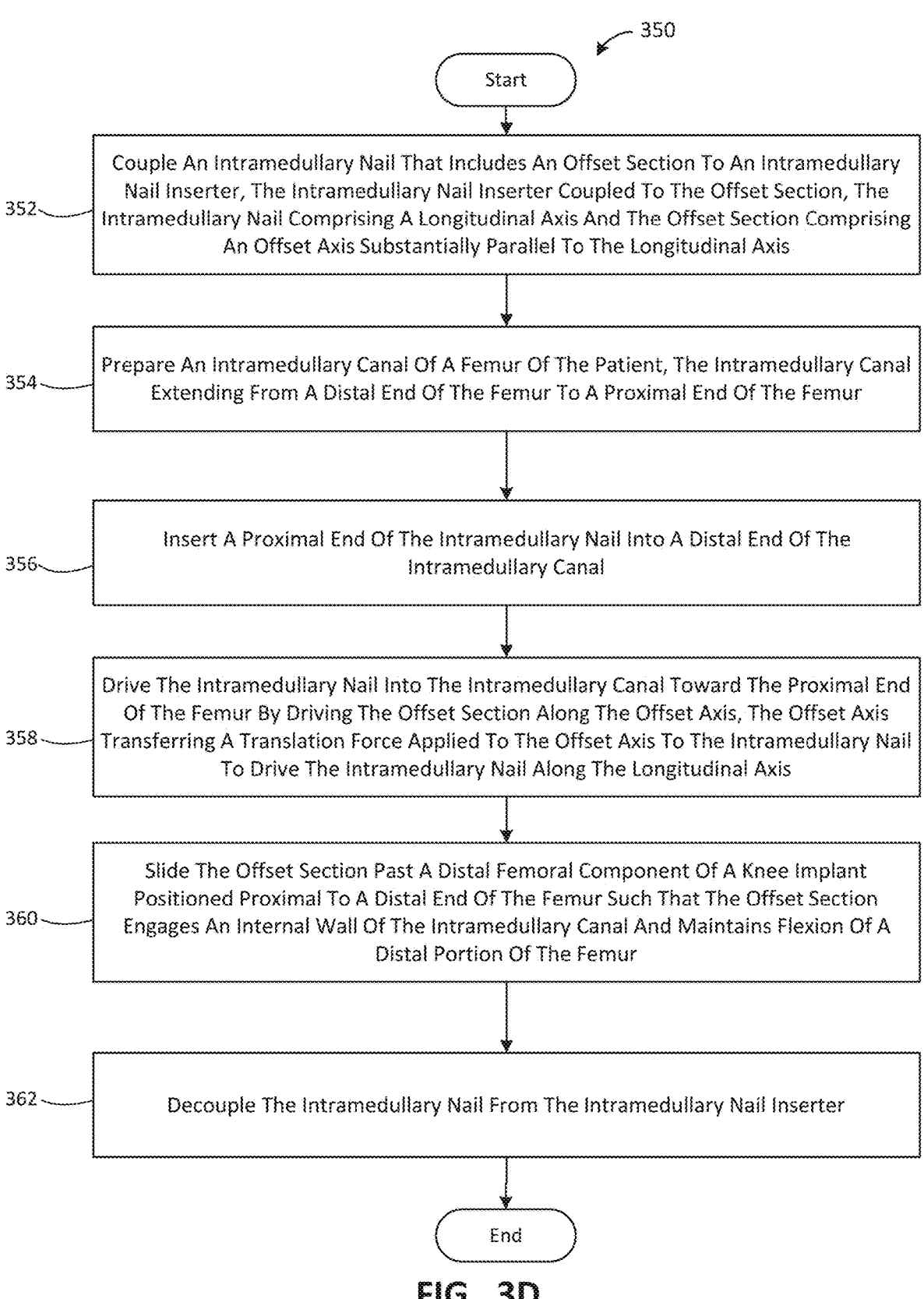
FIG. 3D illustrates one example of a method for deploying an intramedullary nail that includes an offset section.

FIG. 3D illustrates one example of a method 350 for deploying an intramedullary nail that includes an offset section. In certain embodiments, the method 350 begins with a user coupling 352 an intramedullary nail that includes an offset section to an intramedullary nail inserter. The intramedullary nail inserter is coupled to the offset section. The intramedullary nail includes a longitudinal axis and the offset section includes an offset axis substantially parallel to the longitudinal axis.

Next, a surgeon may prepare 354 an intramedullary canal of a femur of the patient. The intramedullary canal extends from a distal end of the femur to a proximal end of the femur. Next, a surgeon may insert 356 a proximal end of the intramedullary nail into a distal end of the intramedullary canal. Then, the surgeon drives 358 the intramedullary nail into the intramedullary canal toward the proximal end of the femur by driving the offset section along the offset axis, the offset axis transferring a translation force applied to the offset axis to the intramedullary nail to drive the intramedullary nail along the longitudinal axis. A translation force applied at the proximal end of the inserter 300 enables translation of the shaft along the longitudinal axis.

Those of skill in the art will appreciate that the intramedullary canal can have a natural bend at the distal end. Conventional, intramedullary nails may include a single bend, or be pliable, to accommodate this natural bend of the intramedullary canal. However, embodiments of the present disclosure include at least two bends such that the offset axis and longitudinal axis are substantially parallel. In this manner, as a surgeon drives 358 the inserter towards the proximal end of the femur, the driving force is transferred through the offset section to the shaft and along the intramedullary canal rather than transverse to a longitudinal axis of the intramedullary canal and/or longitudinal axis of the intramedullary nail 101/202. The insertion direction, the driving direction is in-line with the intramedullary canal and the intramedullary nail moves readily in the intramedullary canal in the direction of the driving force.

Next, a surgeon may slide 360 the offset section past a distal femoral component of a knee implant positioned proximal to a distal end of the femur. The offset section may engage an internal wall of the intramedullary canal and maintain flexion of a distal portion of the femur, particularly distal of a bone fracture 160. Finally, the surgeon may decouple 362 the intramedullary nail from the inserter and the method 350 ends.

In certain embodiments, during or after one or more steps of the method a surgeon may deploy fasteners that engage openings 132 within the intramedullary nail. The openings 132 may be referred to as fastener openings 132. In one embodiment, the inserter 300 includes a fastener guide, such as for example intramedullary nail guide 330 (also referred to as a fastener guide herein). The intramedullary nail guide 330 may include openings 336 aligned with opening 132 in the intramedullary nail. In certain embodiments, a user may modify the method 350 to include the step of a surgeon using the fastener guide 330 to guide insertion of a plurality of fasteners through the fastener openings 132.

The present disclosure discloses surgical devices, systems, and/or methods for fixation in relation to fractures of a long bone of a patient. Existing fixators and/or fixation devices, methods, or steps for long bone fractures are limited.

Conventional bone plates lack features for fixation that account for arteries in close proximity to the long bone (e.g., a neurovascular bundle or femoral artery near the medial side of the femur). A simple bone plate that facilitates fixation that accounts for arteries and/or a neurovascular bundle in close proximity to the long bone is needed. In one embodiment, an improved medial bone plate is needed. The present disclosure provides an improved bone plate that can be used on any side of a bone. Bone plates can be named based on what part of they are intended to be deployed on or to. Thus, a medial bone plate is a bone plate for a medial side of a bone. In addition, the present disclosure includes an improved medial bone plate.

Figure 4A:
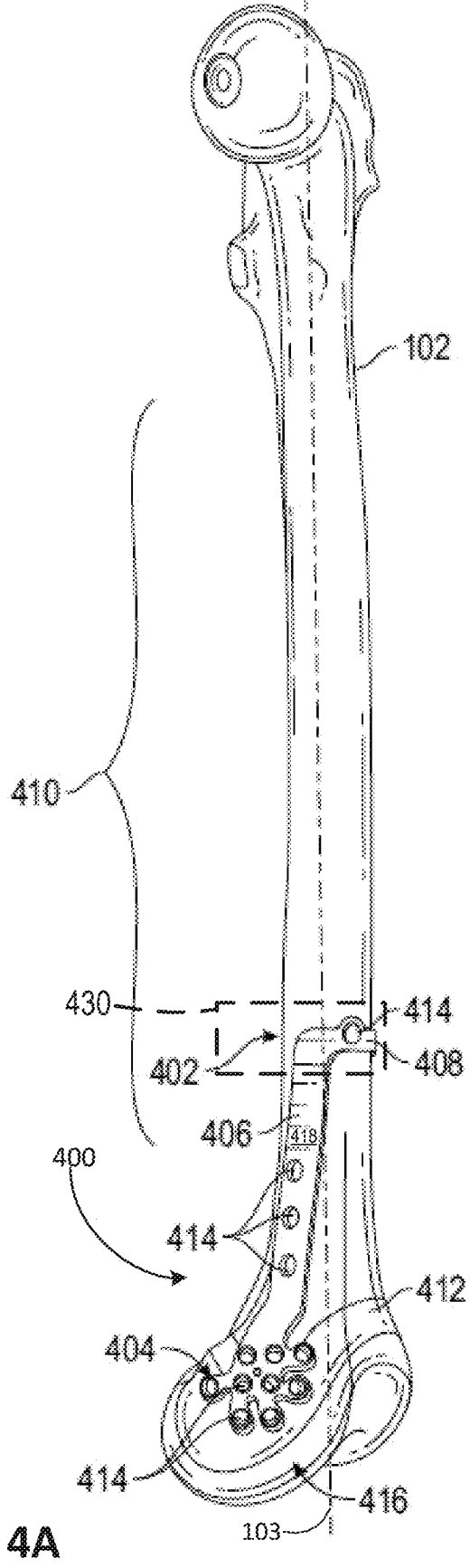
FIG. 4A is a perspective view of a bone plate deployed on a long bone, according to one embodiment.
Figures 4B, 4C:
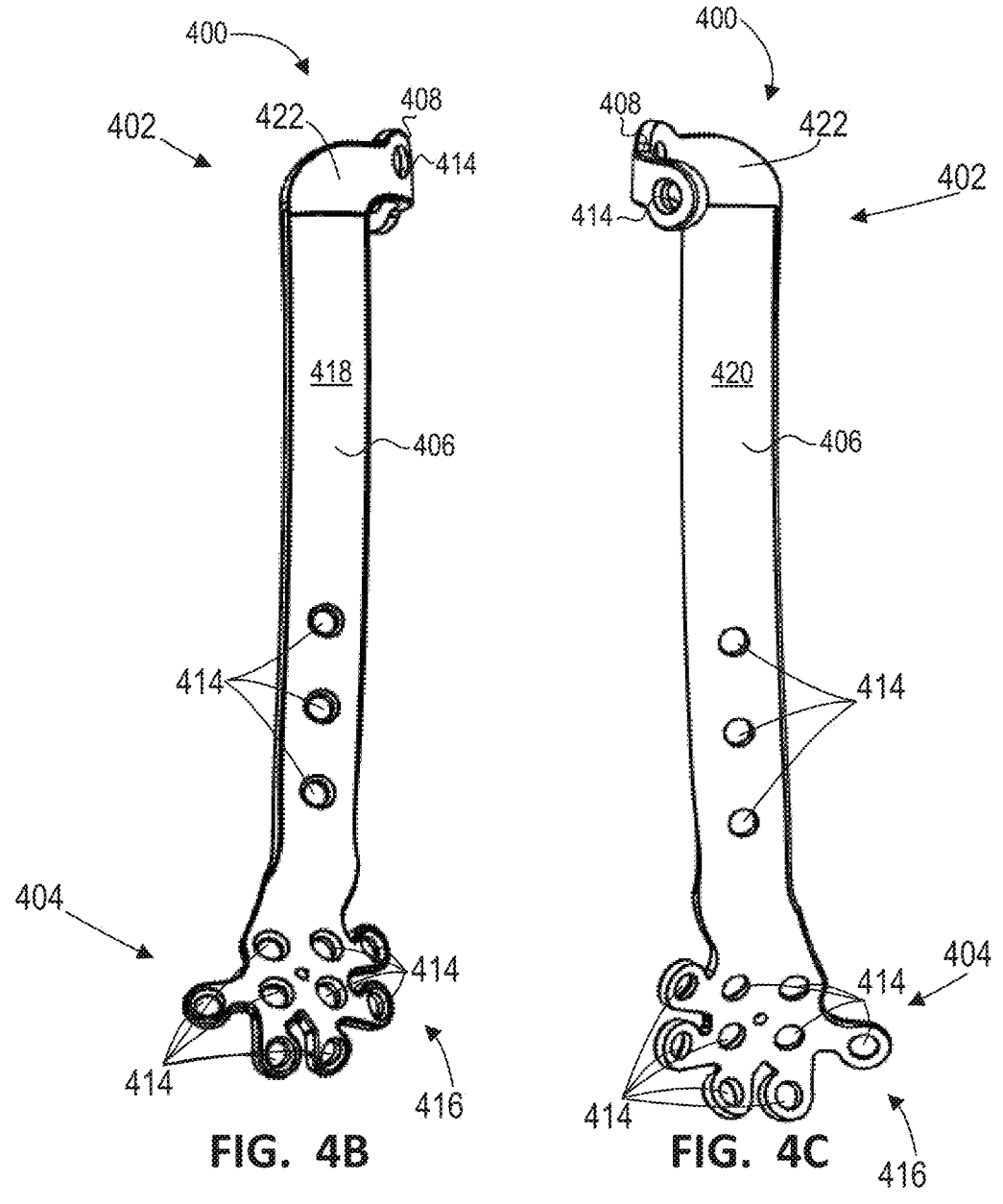
FIGS. 4B, 4C, 4D, and 4E are front view, rear view, left side view, and right side view respectively of the bone plate of FIG. 4A, according to one embodiment.

FIG. 4A is a perspective view of a bone plate 400 deployed on a long bone, such as a femur 102, according to one embodiment. The femur includes a long axis 103. The bone plate 400 includes a proximal end 402, a distal end 404, and a body 406. The proximal end 402 includes one or more arms 408. In certain embodiments, an arm 408 may be referred to as a tab, finger, or the like. In the illustrated embodiment, one arm 408 extends from the body 406 in an anterior direction relative to the femur 102. In another embodiment, the one or more arms 408 may extend from the body 406 in a posterior direction relative to the femur 102. In one embodiment, the arm 408 is proximal (or near) an end of the bone plate 400. For example, the arm 408 is proximal to the proximal end 402.

Figures 4D, 4E:
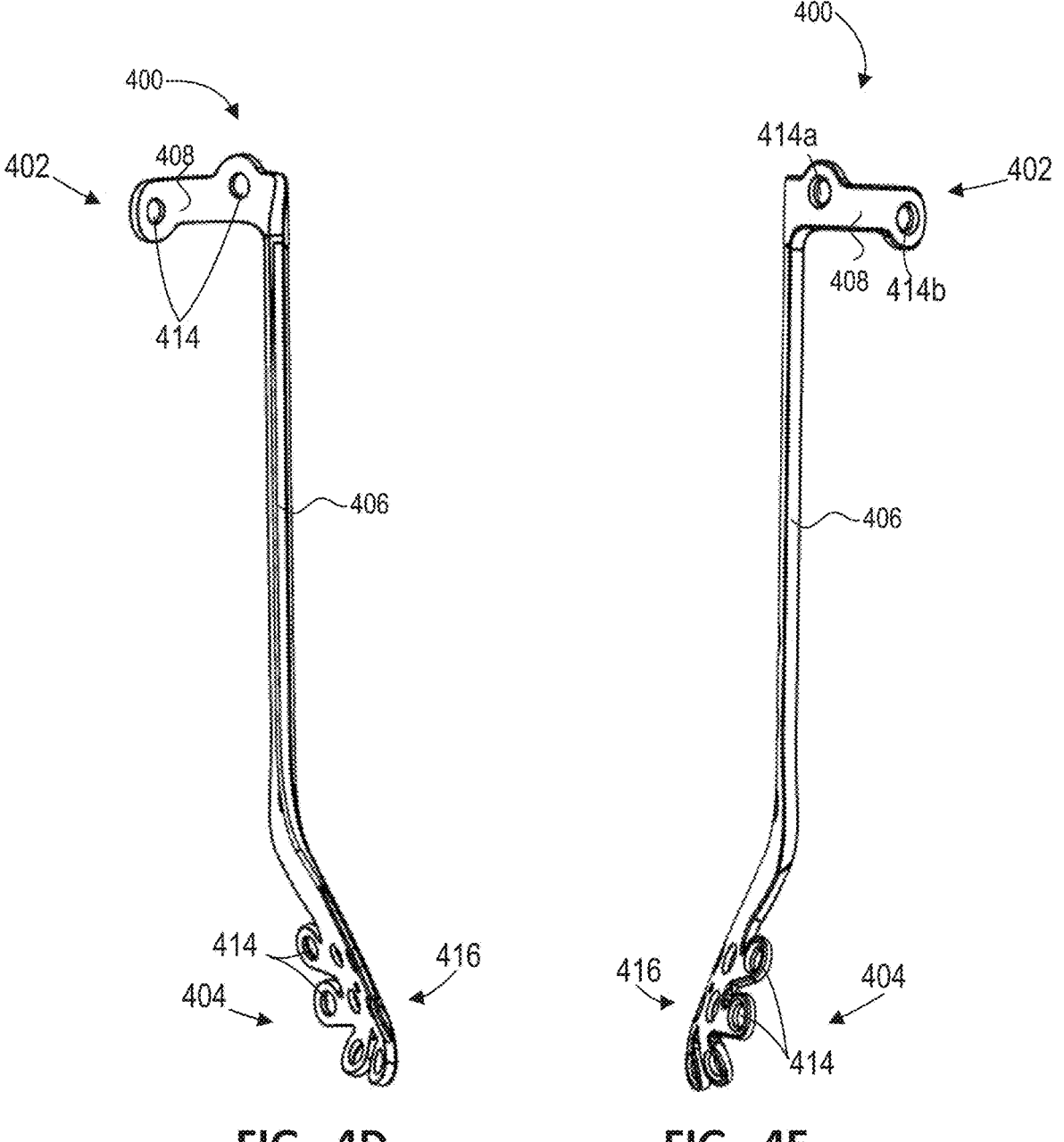

The proximal end 402 may include a first arm 408. The arm 408 may extend over an anterior portion of the femur 102 when the bone plate 400 is in use. Alternatively, or in addition, the arm 408 may extend over a posterior portion of the femur 102. In certain embodiments, the arm 408 extends from the body 406 in a direction perpendicular to the long axis 103 of the femur 102. Since the bone plate 400 is intended to be used on a medial side of a long bone, the arm 408 may extend over and/or to a plurality of sides of the femur 102. For example, in one embodiment, the arm 408 extends to an anterior side of the femur 102. In another example, the arm 408 extends to a lateral side of the femur 102. In another example, the arm 408 extends to posterior side of the femur 102. Of course, the arm 408 may also extend over and/or to multiple sides of the femur 102. In one example embodiment, the arm 408 may extend over both an anterior side and a lateral side of the femur 102. In such an embodiment, the arm 408 may include an anterior fastener opening 414*a* and a lateral fastener opening 414*b* (see FIG. 4E). When in use, the anterior fastener opening 414*a* may be above an anterior side of the femur 102 and the lateral fastener opening 414*b* may be above a lateral side of the femur 102. In one embodiment, the anterior fastener opening 414*a* and lateral fastener opening 414*b* are offset in relation to each other so that an anterior fastener (e.g. a bone screw or other fastener) deployed in the anterior fastener opening 414*a* does not interfere with a lateral fastener (e.g. a bone screw or other fastener) deployed in the lateral fastener opening 414*b*.

In one embodiment, the arm 408 extends from an end of the bone plate 400. In another embodiment, the arm 408 extends from a body of the bone plate 400. The body 406 may extend along a medial side of a femur 102 when the bone plate 400 is in use.

The arm 408 may include at least one fastener opening 414. The distal end 404 may include a distal fixation feature 416 that includes one or more fastener openings 414. The distal fixation feature 416 is configured to engage a medial epicondyle of the femur 102.

The bone plate 400 may be manufactured to have a variety of different widths and/or thicknesses in order to provide a bone plate 400 with a desired level of rigidity/stiffness and/or flexibility or both. Accordingly, the components of the bone plate 400 may be sized to provide a desired length, width, height, or thickness and the material used for one or more components may be selected to provide a desired level of rigidity and/or flexibility, or both.

In one embodiment, the bone plate 400 is configured, designed, and/or engineered to account for the close proximity of a large femoral artery of a patient that runs along the medial side of the femur 102. In particular, the femoral artery sits close to the shaft 410 of the femur 102 and is not as close to the femur 102 near the distal end 412 of the femur 102. The bone plate 400 is configured for percutaneous deployment through an entry point/incision on the inside of the thigh (i.e., medial side at the distal end).

The arm 408 at, or near, the proximal end 402 provides for fixation of bone plate 400 to the femur 102. The arm 408 can include one or more fastener openings 414 positioned at a variety of positions along the arm 408. The one or more fastener openings 414 are each configured to receive a fastener of a variety of types and configurations. Fasteners placed in the fastener openings 414 may engage the cortex of the long bone at a variety of angles, such as between 20 degree and 90 degrees in relation to a longitudinal axis of the long bone. Similarly, the positioning of the fastener openings 414 on the arm 408 can provide for a variety of different angles for the deployment of fasteners into the bone in relation to the bone plate 400. In one embodiment, the fasteners may be deployed at an angle between about 20 degrees relative to a longitudinal axis of the long bone to 90 degrees to 180 degrees (perpendicular to the body 406 of the bone plate 400).

In certain embodiments, the presented solution includes the use of a protected drill sleeve/drill guide protector for deployment of fasteners into the fastener openings 414 of the arm 408 from the lateral side of the long bone. As one example, a surgeon may use a protected drill sleeve/drill guide protector similar to those used for fixation of an anterior cruciate ligament (ACL) guide. Use of the protected drill sleeve/drill guide protector when deploying from the lateral side of the long bone can protect soft tissue of the patient at the entry point and mitigate medial over penetration when the fasteners are deployed.

The distal end 404 may include a fixation feature 416 that includes one or more fastener openings 414. In embodiments where the fixation feature 416 is near the distal end 404 the fixation feature 416 may be referred to as a distal fixation feature 416. The fixation feature 416 may be shaped and contoured to contact and follow a contour of a condyle of the long bone, such as a medial condyle. In certain embodiments, this means that fixation feature 416 may include bends, curves, or other contours to follow a contour of the condyle and/or the bone. The body 406 may be configured to contact a medial surface of a long bone, such as femur 102. Accordingly, the body 406 may include a curve or bow shape to follow a contour of the medial surface of the femur 102.

In one embodiment, the fastener openings 414 (in the body 406, the arm 408, and/or fixation feature 416) and/or fixation feature 416 may be configured to interact with fasteners such as screws, pins, bones screws, or the like. In other embodiments, the bone plate 400 may include other fixation features and the corresponding components for those fixation features in place of the fastener openings 414 and/or fixation feature 416. For example, the fastener openings 414 and/or fixation feature 416 may instead comprise anchors, nuts, threaded openings, buttons, stops, of the like for implementing one or more of a variety of fixation technologies. For example, fixation of the bone plate 400 to the long bone may be done using cables, wires, sutures, suture buttons, flexible fasteners or the like.

In one embodiment, the fastener openings 414 may include internal threads configured to engage a bone screw driven from a lateral side of the long bone and into the fastener opening on the medial side of the long bone and in the body 406 or fixation feature 416. In such an embodiment, the fastener openings 414 provides a nut-like device for fixation. Also in such an embodiment, the arm 408 may include one or more fastener openings 414 that include internal threads configured to engage a bone screw or other fastener driven from a posterior side or anterior side of the long bone and into the fastener opening on the anterior side or posterior side of the long bone. In certain embodiments, fasteners can be deployed from a lateral side of the long bone and secured to the fixation feature 416 on the medial side.

Alternatively, or in addition, the body 406 and/or fixation feature 416 may not include openings such as fastener openings 414. Instead, the body 406 and/or fixation feature 416 may be made from a material that permits a fastener driven from a lateral side of the long bone to penetrate the body 406 and/or fixation feature 416 and thereby tap its own opening into the bone plate 400.

The body 406 may be of any length between the fixation feature 416 and the proximal end 402. In certain embodiments, the bone plate 400 may be manufactured in a variety of sizes with different lengths for the body 406 and/or other components to accommodate different types and locations of fractures of the long bone, sizes of long bone, and/or anatomical characteristics of the patient. In one embodiment, the bone plate 400 used is selected such that the arm 408 is superior to a fracture in the long bone. In certain embodiments, the arm 408 can straddle a fracture.

The body 406 may also include one or more fastener openings 414. Together, the arm 408, body 406, and fixation feature 416 with the respective one or more fastener openings 414 provide a surgeon with a number of options for fixing the bone plate 400 to the femur 102 on the medial side without a need to attempt fixation using a fastener on the medial side alongside the shaft 410 in close proximity to the large femoral artery of a patient. Different embodiments of the bone plate 400 can include different configurations and/or arrangements of the one or more fastener openings 414 positioned along the length of the body 406 and/or within the fixation feature(s) 416. In certain embodiments, certain parts of the body 406 and/or fixation feature(s) 416 may include no fastener openings 414 or any other openings and may instead provide a solid structure which may serve to provide desired strength, durability, and/or rigidity.

In certain embodiments, the bone plate 400 is connectable to other implants such as an intramedullary nail, lateral bone plate, other medial bone plate, arthroplasty implant, or the like. The bone plate 400 may connect to these other implants using fasteners or may connect by way of connectors that may be formed in one or the other or both of the bone plate 400 and the other implant.

FIGS. 4B, 4C, 4D, and 4E are front view, rear view, left side view, and right side view respectively of the medial bone plate of FIG. 4A, according to one embodiment. The bone plate 400 may include a superior surface 418 and a bone-facing surface 420. The superior surface 418 faces away from the long bone (e.g., femur 102). The bone plate 400 may be generally planar. In one embodiment, the bone-facing surface 420 is configured to contact and follow the contour of a medial surface of the long bone (e.g., femur 102). In one embodiment, the bone-facing surface 420 may face a single side of the long bone (e.g., femur 102) when in use.

As used herein, "bone-facing surface" refers to a surface of an object, instrument, or apparatus, such as an implant that is oriented toward or faces one or more bones of a patient. In one aspect, the bone-facing surface may abut, touch, or contact a surface of a bone. In another aspect, the bone-facing surface or parts of the bone-facing surface may be close to, but not abut, touch, or contact a surface of the bone.

FIGS. 4A, 4B, 4C, 4D, and 4E illustrate one example embodiment of a bone plate 400. In this example, the arm 408 extends from the body 406 in an anterior direction in relation to the long bone (See FIG. 4A). Alternatively, or in addition, the arm 408 may also extend from the body 406 in a posterior direction in relation to the long bone (See FIG. 4A).

In one embodiment, the arm 408 may connect to the body 406 by way of an elbow 422. The elbow 422 may be shaped to facilitate percutaneous deployment of the bone plate 400. The arm 408 may be positioned at the furthermost part of the proximal end 402 or at any position between the proximal end 402 and the fixation feature 416. Furthermore, the bone plate 400 may include one or more arms 408 positioned along its length and the arms 408 may each extend in the anterior direction relative to the long bone, may each extend in the posterior direction relative to the long bone, and/or some arms 408 may extend in the anterior direction relative to the long bone while other arms 408 extend in the posterior direction relative to the long bone.

In one embodiment, the medial bone plate may be a modular bone plate that includes one or more connectors on a proximal end 402 and/or a distal end 404. With a modular bone plate, the arm 408 may be connectable to the modular bone plate such that the arm 408 extends anteriorly relative to the long bone or posteriorly relative to the long bone. In certain embodiments, the body 406 may include a number of connection points for an arm 408 to be connected such that a surgeon can fixate the arm 408 at a variety of locations on the anterior surface and/or posterior surface of the long bone. In addition, the fixation feature 416 may be connectable to the modular bone plate at or near the distal end 404.

In certain embodiments (not shown), the distal end 404 may include one or more fixation features 416 and the proximal end 402 may not include one or more arms 408. In such embodiments, the body 406 may include a bend, twist, or curve along its length. The bend, twist, or curve may be designed, configured, or engineered such that the one or more fixation features 416 can contact a medial surface of the long bone and the proximal end 402 is positioned above an anterior surface or a posterior surface of the long bone. In such an embodiment, the proximal end 402 may include one or more fastener openings 414 and/or one or more fastener features.

Figure 5A:
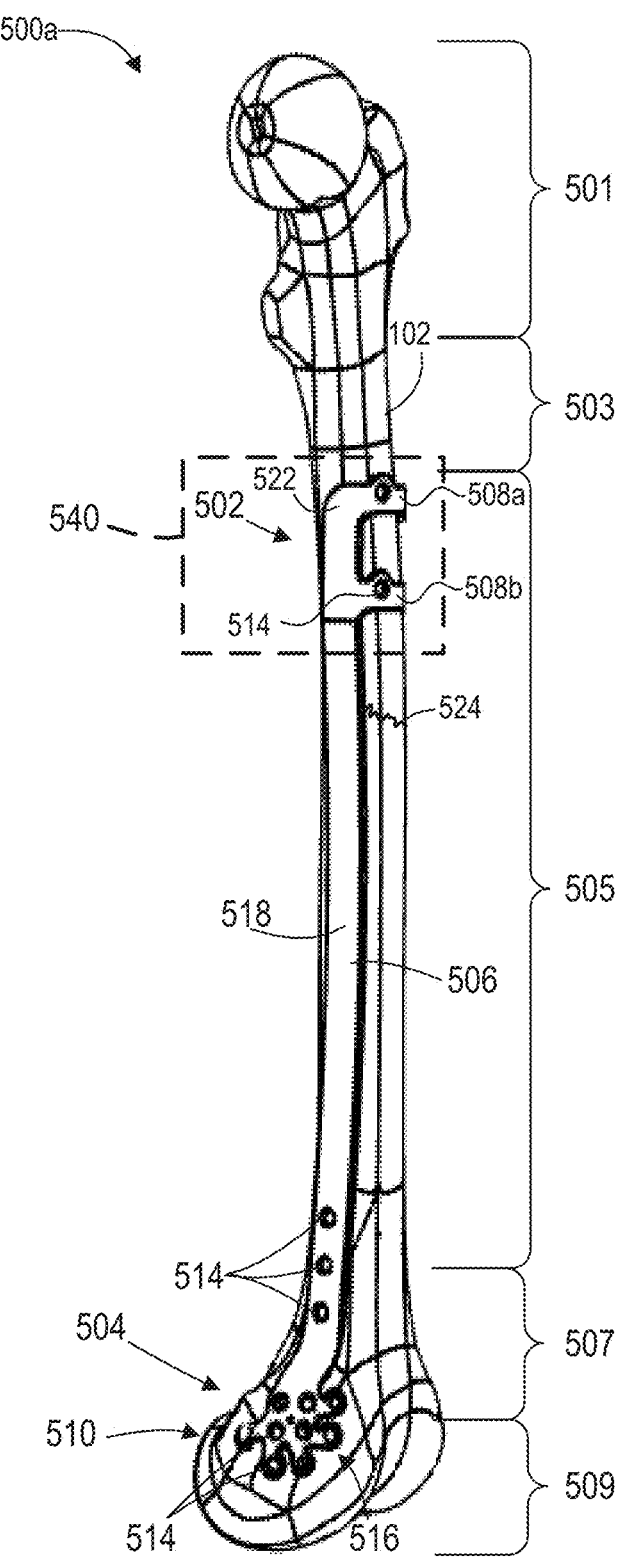
FIG. 5A is a perspective view of a medial bone plate deployed on a long bone, according to one embodiment.

FIG. 5A is a perspective view of a medial bone plate 500*a* deployed on a long bone, according to one embodiment. The medial bone plate 500*a* may have structures, features, and functions, operations, and configuration similar to that of the bone plate 400 described in relation to FIG. 4A-4E. Accordingly, the medial bone plate 500*a* may include a proximal end 502, distal end 504, body 506, one or more arms 508, one or more fastener openings 514, a distal fixation feature 516, a superior surface 518, a bone-facing surface 520 (not shown), and one or more elbows 522. In the illustrated embodiment, the medial bone plate 500*a* has a longer body 506 such that the arms 508 are positioned above a fracture 524.

The femur 102 includes a proximal epiphysis 501, a proximal metaphysis 503, diaphysis 505, a distal metaphysis 507, and a distal epiphysis 509. In one embodiment, the proximal end 502 is near the proximal epiphysis 501 of the femur 102. The distal end 504 is near a medial epicondyle 510 of the femur 102. The medial bone plate 500*a* includes a first arm 508*a* near a proximal end 502 of the medial bone plate 500*a*. The medial bone plate 500*a* also includes a second arm 508*b* between a distal fixation feature 516 and the first arm 508*a*. The second arm 508*b* may extend from the body 506 over an anterior side of the femur 102. Alternatively, or in addition, the second arm 508*b* may extend from the body 506 over a posterior side of the femur 102.

"Epiphyses" refers to the rounded end of a long bone, at long bone's joint with adjacent bone(s). Between the epiphysis and diaphysis (the long midsection of the long bone) lies the metaphysis, including the epiphyseal plate (growth plate). At the joint, the epiphysis is covered with articular cartilage; below that covering is a zone similar to the epiphyseal plate, known as subchondral bone. (Search 'epiphysis' on Wikipedia.com 17 Jun. 2022. Modified. Accessed Aug. 1, 2022.) "Metaphysis" refers to the neck portion of a long bone between the epiphysis and the diaphysis. The metaphysis contains the growth plate, the part of the bone that grows during childhood, and as the metaphysis grows the metaphysis ossifies near the diaphysis and the epiphyses. (Search 'metaphysis' on Wikipedia.com 17 Jun. 2022. Modified. Accessed Aug. 1, 2022.) "Diaphysis" refers to the main or midsection (shaft) of a long bone. The diaphysis is made up of cortical bone and usually contains bone marrow and adipose tissue (fat). The diaphysis is a middle tubular part composed of compact bone which surrounds a central marrow cavity which contains red or yellow marrow. In diaphysis, primary ossification occurs. (Search 'diaphysis' on Wikipedia.com 17 Jun. 2022. Modified. Accessed Aug. 1, 2022.)

Figures 5B, 5C, 5D:
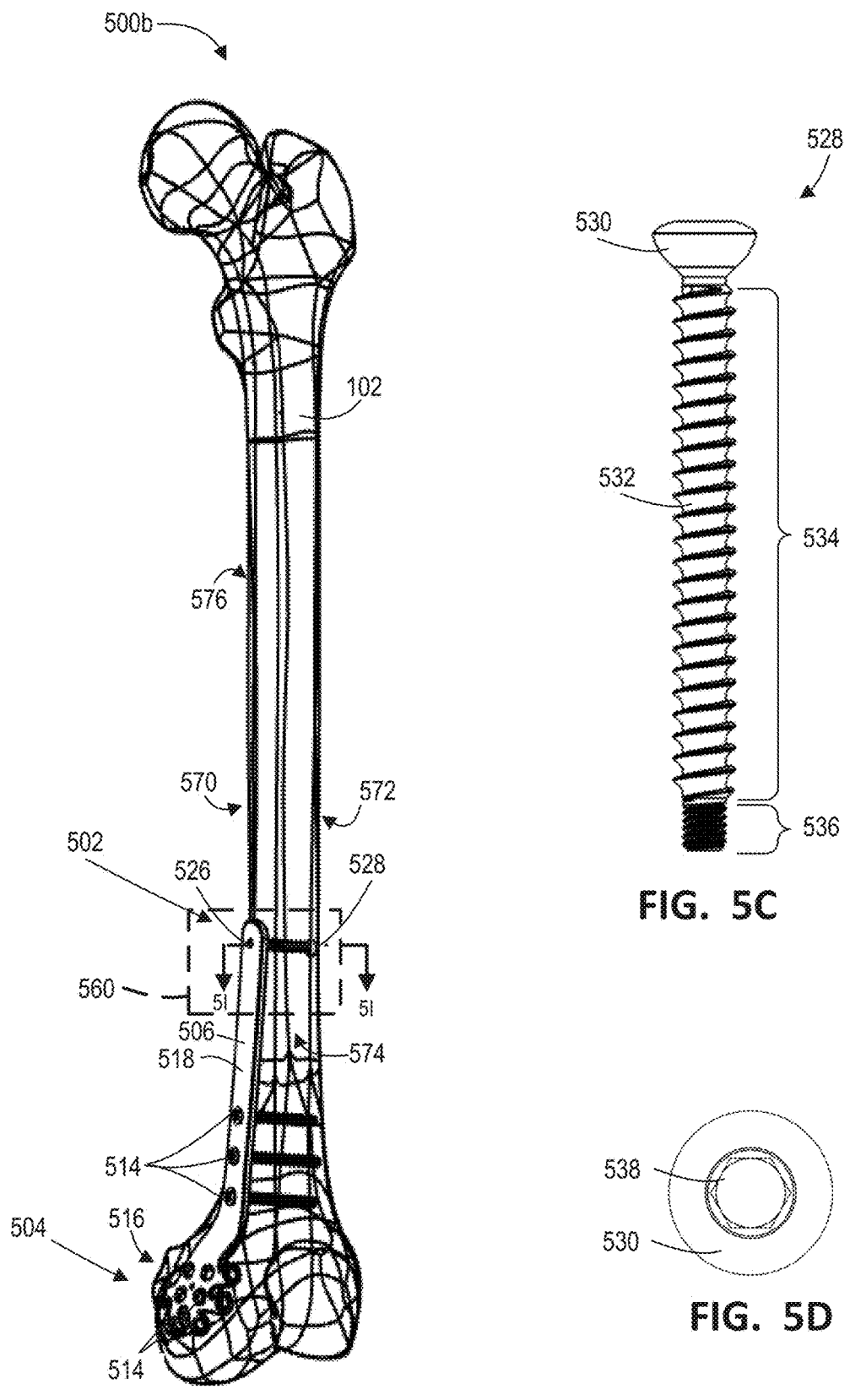
FIG. 5B is a perspective view of a medial bone plate deployed on a long bone, according to one embodiment.
FIG. 5C is a perspective view of a fastener for use with the medial bone plate of FIG. 5B, according to one embodiment.
FIG. 5D is a top view of a head of the fastener of FIG. 5C, according to one embodiment.

Referring now to FIGS. 4A, 5A, and 5B, the present disclosure includes different embodiments of a bone plate that includes a low-profile fixation assembly 430, 540, 560. A low-profile fixation assembly 430, 540, 560 is a type of fastener, fixation system, fixation assembly, assembly, and/or fixator specifically designed, engineered, and/or configured to have no profile, or a very low profile, or a minimal height profile. In connection with a low-profile fixation assembly 430, 540, 560 height refers to a distance that the fixation assembly (and/or its members) extends above and/or below a reference point, reference surface, reference line, and/or reference axis. In the illustrated embodiments, the reference surface may be surface (e.g., superior surface 418) of a fastener such as a bone plate 500a,b.

A low-profile fixation assembly 430, 540, 560 can be advantageous because the low-profile fixation assembly 430, 540, 560 can be used in areas where fixation is desired but other anatomic structures are in close proximity to one side or portion or aspect of an implant when the implant is deployed to a desired position, location, or orientation. For example, a medial side of a femur 102 can include a variety of important soft tissues such as a neurovascular bundle, a femoral artery, and the like which are positioned in close proximity to the surface of the medial side of the femur 102. In procedures where an implant is to be deployed between the medial cortex of the femur 102 and these important soft tissues a low-profile fixation assembly 430, 540, 560 can be used because the low-profile fixation assembly 430, 540, 560 does not impinge (or may minimally impinge) on the important soft tissues, does not require a surgical approach from the medial side of the medial side of the long bone, and still provides sufficient stability, securement, and fixation of the implant to the femur 102.

Advantageously, a low-profile fixation assembly 430, 540, 560 can have a variety of configurations, features, components, structures, members, and/or implementations. In certain embodiments, the low-profile fixation assembly 430, 540, 560 may be characterized by how a fastener or fastener assembly or apparatus approaches the low-profile fixation assembly 430, 540, 560 to activate or engage the low-profile fixation assembly 430, 540, 560 for deployment and fixation. For example, in one embodiment an end or portion of an implant can be slid percutaneously between important soft tissues (or other anatomical structures) and a surface or side of a long bone such that the implant is positioned on one side of the long bone (e.g., femur 102) but fixation of the low-profile fixation assembly 430, 540, 560 is accomplished by approaching the implant from any side other than the side the implant is deployed on. The present disclosure includes a few examples for illustration. More details of the low-profile fixation assembly 430, 540, 560 are described below in the illustrative examples.

In FIG. 4A, one example of the low-profile fixation assembly 430 includes an arm 408 that extends towards the long bone and an elbow 422 and does not extend away from the long bone any distance above the superior surface 418. Similarly, in FIG. 5A, the low-profile fixation assembly 540 includes first arm 508a and a second arm 508b that extend towards the long bone and one or more elbows 522 and does not extend away from the long bone any distance above the superior surface 518. Also in FIG. 5B, the low-profile fixation assembly 560 includes a fastener 528 that engages the medial bone plate 500b from a lateral side of the long bone and thus does not extend away from the long bone any distance above the superior surface 518.

FIG. 5B is a perspective view of a medial bone plate 500b deployed on a long bone, according to one embodiment. The long bone depicted as a transparent depiction of a femur 102 and is shown from a perspective that shows the medial side 570 and the anterior side 574 of the femur 102. The lateral side 572 is opposite the medial side 570 and is shown in FIG. 5B by way of the transparent view of the long bone. The posterior side 576 is opposite the anterior side 574 and is shown in FIGS. 5B and 5L by way of the transparent view of the long bone.

The medial bone plate 500b may have many structures, features, and functions, operations, and/or configuration similar to that of the medial bone plate 500a described in relation to FIG. 5A, like parts are identified with the same reference numerals. Accordingly, the medial bone plate 500a may include a proximal end 502, distal end 504, body 506, one or more fastener openings 514, and a distal fixation feature 516.

The medial bone plate 500b includes a body 506 and a low-profile fixation assembly 560. The body 506 includes a proximal end 502, distal end 504, a superior surface 518 and a bone-facing surface 520. The superior surface 518 faces away from a long bone (away from the medial side 570) when the medial bone plate 500b is in use. The bone-facing surface 520 faces the medial side 570 of the long bone when the medial bone plate 500b is in use.

In certain embodiments, the medial bone plate 500b can be deployed percutaneously through an incision near the distal end of the femur 102. The medial bone plate 500b can be slide along the surface of the medial side 570 of the femur 102. Advantageously, the medial bone plate 500b can be slide between important soft tissues positioned along the medial side 570 and the surface of the medial side 570 of the femur 102.

With the medial bone plate 500b positioned on or near the surface of the medial side 570 and between skin surface and important soft tissues below the skin surface, the low-profile fixation assembly 560 enables fixation of the proximal end 502 of the medial bone plate 500b by engaging and/or approaching the proximal end 502 from any other side of the femur 102 besides the medial side 570. Thus, embodiments of the low-profile fixation assembly 560 can complete fixation by aspects/features that approach from the lateral side 572, anterior side 574, and/or posterior side 576.

In certain embodiments, a low-profile fixation assembly can include a single piece or a plurality of components that cooperate to provide the fixation. In one example, the low-profile fixation assembly may include one or more arms or tabs that extend from an implant body (See FIG. 4A) that include fastener openings and a set of fasteners configured to engage with the fastener openings and engage with a long bone to fixate at least a portion of an implant to the long bone. In one example, the low-profile fixation assembly 560 may include a fastener deployed from a lateral side 572 that engages the bone first and then engages with the implant (or a fastener opening of the implant).

A fastener deployed from a non-medial side of a bone that engages with bone first and then engages with an implant or corresponding aspect of a fastener assembly is referred to herein as a bone-approach fastener. The corresponding aspect of a fastener assembly engaged by the bone-approach fastener is referred to herein as a bone-approach fixation feature. One example of a bone-approach fixation feature is an opening within internal threads the correspond to external threads of a bone-approach fastener. In contrast, a fastener deployed such that fastener engages with an implant (e.g., a bone plate) or corresponding aspect of a fastener assembly first and then engages with bone is referred to herein as a plate-approach fastener. The corresponding aspect of a fastener assembly engaged by the plate-approach fastener is referred to herein as a plate-approach fixation feature. One example of a bone-approach fixation feature is an opening within a bone plate sized to accept the plate-approach fastener. Another example of a bone-approach fixation feature may be external threads on the plate-approach fastener that engage bone when the plate-approach fastener is deployed.

In another example, the low-profile fixation assembly 560 may include an opening in the implant, a pair of buttons and a tether that extends between the buttons. In yet another example, the low-profile fixation assembly 560 may include a coupler of the implant that engages with a tether connected to an anchor anchored in one of the lateral side 572, anterior side 574, and/or posterior side 576 of the femur 102.

In the illustrated embodiment, the medial bone plate 500*b* differs from the medial bone plate 500*a* because the low-profile fixation assembly 560 includes a lateral approach fastener opening 526.

In one embodiment, a lateral approach fastener opening 526 is a fastener opening configured to accept a lateral approach fastener 528. A lateral approach fastener 528 is a fastener designed to engage with an implant or a corresponding feature of a fixator from a lateral side of a bone. The lateral approach fastener opening 526 and lateral approach fastener 528 may be part of the low-profile fixation assembly 560.

A lateral approach fastener opening 526 can be implemented in a variety of ways. In the illustrated embodiment, the lateral approach fastener opening 526 is a set of internal threads (not shown) of an opening that are configured to engage external threads 536 of lateral approach fastener 528 that passes through the long bone. The lateral approach fastener opening 526 may extend from the bone-facing surface 520 towards the superior surface 518. In one embodiment, the lateral approach fastener opening 526 may extend all the way through from the bone-facing surface 520 and through the superior surface 518. In another embodiment, the lateral approach fastener opening 526 may extend partially from the bone-facing surface 520 toward the superior surface 518 but not pass through the superior surface 518.

Advantageously, the lateral approach fastener 528 is deployed from a lateral side of the long bone so as to avoid a neurovascular bundle and/or femoral artery near the medial side of the long bone. Those of skill in the art will recognize a variety of different designs for anon-medial side approach fastening system such as the example lateral approach fastener opening 526 and lateral approach fastener 528 presented here, each of which is considered within the scope of the present disclosure.

In another embodiment, the low-profile fixation assembly 560 may not initially include a lateral approach fastener opening 526 formed in the body 506. Instead, the lateral approach fastener 528 may include an end configured to pierce the body 506 and thereby form a lateral approach fastener opening 526 as the lateral approach fastener 528 is deployed (e.g., self-tapping).

In certain embodiments, a lateral approach fastening system is one example of non-medial side approach fastening system. In one embodiment, an opposite side approach fastening system is one that can include two components one on one side of a body part or section of tissue and one on an opposite of the body part or section of tissue. An opposite side approach fastening system can be used in relation to a medial-lateral axis, an anterior-posterior axis, a superior-inferior axis, a cephalad-caudal axis, and the like.

FIG. 5C is a perspective view of a lateral approach fastener 528 for use with the medial bone plate of FIG. 5B, according to one embodiment. The lateral approach fastener 528 can include a head 530 and a shank 532. In one embodiment, the head 530 may be angled to engage with bone when deployed. The shank 532 can include two sets of threads, coarse threads 534 and fine threads 536. The coarse threads 534 may have a greater pitch to facilitate purchase of the threads in bone of the long bone. The fine threads 536 may include smaller pitch that matches the pitch of internal threads of a lateral approach fastener opening 526 to provide enhanced engagement and fixation with a medial bone plate 500*b*.

FIG. 5D is a top view of a head 530 of the lateral approach fastener 528 of FIG. 5C, according to one embodiment. The head 530 can include a drive recess 538. The drive recess 538, or other torque-receiving is configured to receive a drive member of a fastening tool (not shown) used to install the lateral approach fastener 528. The drive recess 538 can be configured to have any one of a variety of shapes including slotted, Torx, Torx plus, Philips, Quadrex, Pozidriv, square recess, tri-wing, spanner, or the like. The drive recess 538 can be centered on a longitudinal axis of the lateral approach fastener 528 which aligns with a longitudinal axis of a lateral approach fastener opening 526 when the lateral approach fastener 528 is inserted into the opening. Of course, those of skill in the art recognize that the shape and configuration of the drive member and the drive recess 538 can be reversed and thus comprise an embodiment within the scope of the present disclosure.

Figures 5E, 5F, 5G, 5H, 5I, 5J:
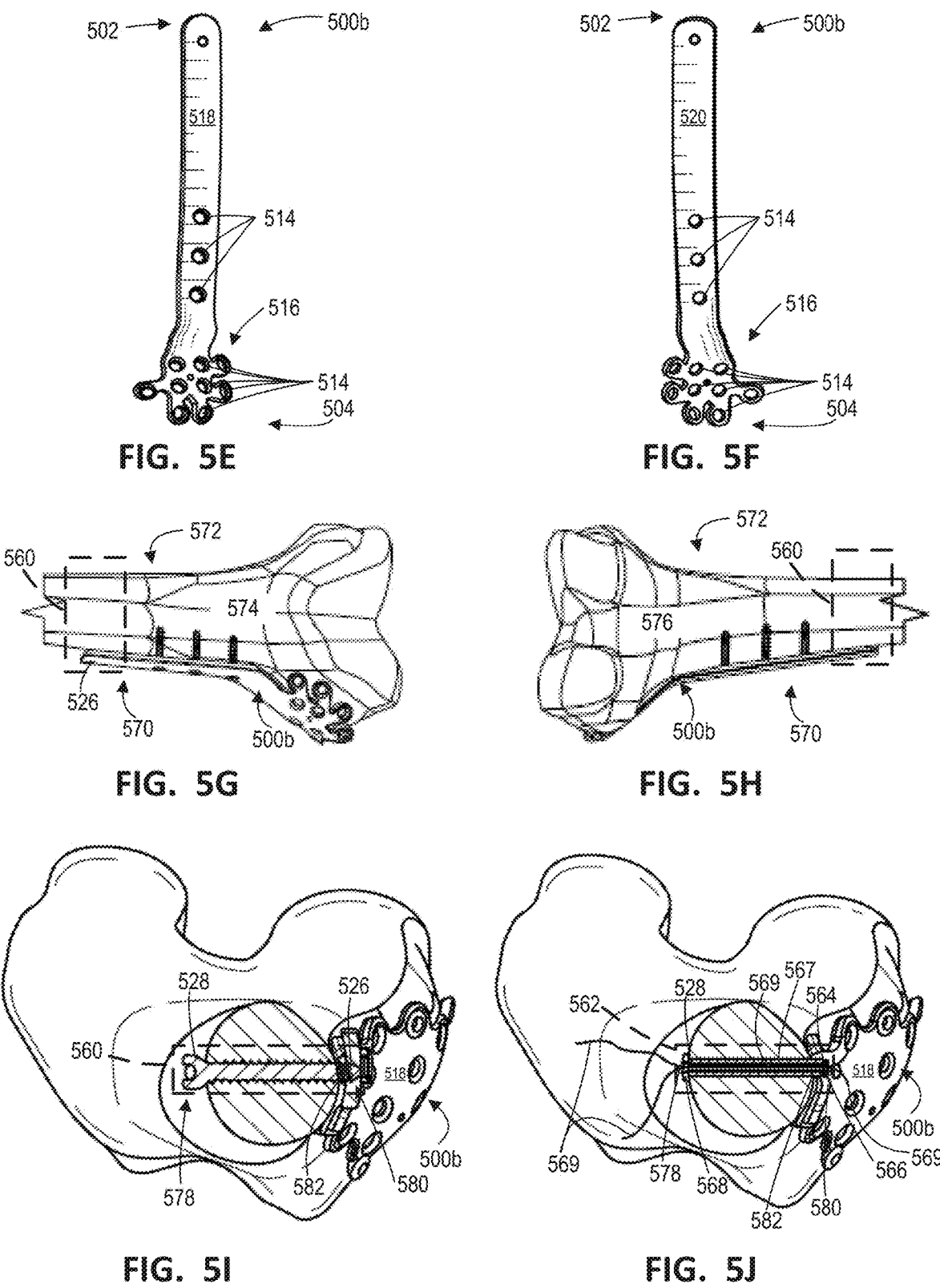
FIG. 5E is a front view of a bone plate of FIG. 5B, according to one embodiment.
FIG. 5F is a rear view of a bone plate of FIG. 5B, according to one embodiment.
FIG. 5G is a side view of a bone plate of FIG. 5B showing a side that faces anteriorly when the bone plate is deployed, according to one embodiment.
FIG. 5H is a side view of a bone plate of FIG. 5B showing a side that faces posteriorly when the bone plate is deployed, according to one embodiment.
FIG. 5I is a cross-section view of a bone plate deployed on a long bone taken along line 5I-5I of FIG. 5B, according to one embodiment.
FIG. 5J is a cross-section view of a bone plate deployed on a long bone taken along line 5I-5I of FIG. 5B a showing an alternative fastener assembly, according to one embodiment.

FIG. 5E is a front view of a bone plate of FIG. 5B, according to one embodiment. The bone plate may be a medial bone plate 500*b* having a superior surface 518 that faces away from the long bone when the bone plate 500*b* is in use. The superior surface 518 may have a variety of configurations. In the illustrated embodiment, the superior surface 518 extends along the body 506 which can be elongate and configured to extend along a medial side of the long bone. The superior surface 518 may extend to, and/or include, the distal fixation feature 516 that includes fastener openings 514 for deploying fasteners to secure the medial bone plate 500*b* to the long bone.

FIG. 5F is a rear view of a bone plate of FIG. 5B, according to one embodiment. The bone plate may be a medial bone plate 500*b* having a bone-facing surface 520 that faces a first side of the long bone when the bone plate is in use. The bone-facing surface 520 may have a variety of configurations. In the illustrated embodiment, the bone-facing surface 520 extends along the body 506 which can be elongate and configured to extend along a medial side/medial cortex of the long bone. The bone-facing surface 520 and/or superior surface 518 may include one or more bends such that the contour of the medial bone plate 500*b* substantially matches a contour of the medial side of the long bone. The bone-facing surface 520 may also include a concave section that is contoured to substantially match the contour of a medial epicondyle of the long bone. In one embodiment, the bone-facing surface 520 faces a medial side of the long bone when the medial bone plate 500*b* is in use. The medial side may be referred to herein as a first side of the long bone.

FIG. 5G is a side view of a bone plate of FIG. 5B showing a side of the medial bone plate 500*b* that faces anteriorly when the bone plate 500*b* is deployed, according to one embodiment. FIG. 5G illustrates a profile for the low-profile fixation assembly 560. In the illustrated embodiment, the low-profile fixation assembly 560 may include a lateral approach fastener opening 526 and a lateral approach fastener 528 (Not shown in FIG. 5G, See FIG. 5B). Advantageously, the low-profile fixation assembly 560 extends no distance above the superior surface 518 and extends for the length of the lateral approach fastener 528 from the bone-facing surface 520 when the lateral approach fastener 528 is deployed. Consequently, the low-profile fixation assembly 560 has a profile that is no longer than a length of the lateral approach fastener 528, for lateral approach fastener 528 that are sized to enter the lateral approach fastener opening 526 but not extend above the superior surface 518. In certain embodiments, the lateral approach fastener opening 526 may extend from the bone-facing surface 520 but not extend past and connect to the superior surface 518. In such an embodiment, the low-profile fixation assembly 560 may have an even smaller profile.

FIG. 5H is a side view of a bone plate of FIG. 5B showing a side that faces posteriorly when the bone plate is deployed, according to one embodiment. FIG. 5G illustrates the same profile for the low-profile fixation assembly 560 as shown in FIG. 5G, but from the opposite side. In the illustrated embodiment, the low-profile fixation assembly 560 may include a lateral approach fastener opening 526 (not visible in FIG. 5H) and a lateral approach fastener 528 (Not shown in FIG. 5G, See FIG. 5B). The low-profile fixation assembly 560 is one example of a low-profile fixation assembly that extends no distance past an implant in one direction and extends a limited distance past the implant in an opposite direction.

FIG. 5I is a cross-section view of a bone plate deployed on a long bone taken along line 5I-5I of FIG. 5B, according to one embodiment. FIG. 5I illustrates one example of a low-profile fixation assembly 560 that includes a fastener opening (e.g., lateral approach fastener opening 526) that extends from the bone-facing surface 520 into the body 506 of the bone plate 500b.

In one embodiment, the fastener opening extends to, and includes, the superior surface 518. In another embodiment, the fastener opening extends into the body 506 and stops short of the superior surface 518. In one embodiment, the fastener opening is near the proximal end 502. In one embodiment, the fastener opening includes internal threads.

The low-profile fixation assembly 560 also includes a fastener (e.g., lateral approach fastener 528). The fastener includes a proximal end 578, a distal end 580, and external threads 582 near the distal end 580. The external threads 582 are configured to engage with internal threads of the fastener opening (e.g., lateral approach fastener opening 526) of the medial bone plate 500b. The fastener may have a greater length than a diameter of the long bone near the fastener opening (e.g., lateral approach fastener opening 526). The distal end 580 of the fastener enters the fastener opening from the bone-facing surface 520 and advances towards the superior surface 518 by way of the external threads 582 engaging with the internal threads of the fastener opening. Said another way, the fastener approaches the bone-facing surface 520 and moves within the fastener opening towards the superior surface 518.

FIG. 5J is a cross-section view of a bone plate deployed on a long bone taken along line 5I-5I of FIG. 5B a showing an alternative fastener assembly, according to one embodiment. FIG. 5J illustrates similar structures, features, and functions, operations, and configuration to that of FIG. 5I. The difference is that FIG. 5J illustrates an alternative design 562 for the low-profile fixation assembly 560.

The low-profile fixation assembly 562 may include an anchor opening 564, an anchor 566, a head 568, and tether 569. The anchor opening 564 may extend from the bone-facing surface 520 through to the superior surface 518 and through the superior surface 518. The anchor 566 may sit near the superior surface 518. The head 568 is configured to sit near another side of the long bone when the medial bone plate 500b is installed. In one embodiment, the head 568 may sit on or near a side opposite the side the bone-facing surface 520 faces. In another embodiment, the head 568 may sit on or near a side different from the side the bone-facing surface 520 faces. In one embodiment, the head 568 is a button that includes holes configured to receive an end of the tether 569.

The anchor opening 564 is configured to accept and/or secure an anchor 566. In one embodiment, the anchor 566 is a button that includes holes configured to receive an end of the tether 569. In one embodiment, the anchor 566 may be integrated into the anchor opening 564. For example, the anchor 566 may be a hook or other extension member that extends into the anchor opening 564.

The tether 569 may be a flexible material that can connect the head 568 and the anchor 566. In one embodiment, the tether 569 is a suture having one or more ends tied or connected to the head 568 and one or more ends tied or connected to the anchor 566. The tether 569 may reside within a bone tunnel 567.

"Head" refers to a device, apparatus, member, component, system, assembly, module, subsystem, circuit, or structure, organized, configured, designed, arranged, or engineered to have a prominent role in a particular feature, function, operation, process, method, and/or procedure for a device, apparatus, member, component, system, assembly, module, subsystem, circuit, or structure the includes, is coupled to, or interfaces with the head. In certain embodiments, the head may sit at the top or in another prominent position when interfacing with and/or coupled to a device, apparatus, member, component, system, assembly, module, subsystem, circuit, or structure. The term "tether" is used herein to mean any strand or flexible member, natural or synthetic, able to join or connect or couple two structures or components. In one embodiment, a tether can join tissue of a patient and/or to be anchored in a bone tunnel or to hard tissue and useful in a surgical procedure. A tether may join two structures either directly by connecting directly to one structure or directly to the other or indirectly by connecting indirectly (by way of one or more intermediary structures) to one structure, to the other structure, or to both structures. In certain embodiments, "tether" refers to a flexible line or flexible member of natural material, natural biological material, biomaterial, biomimetic materials, manmade material, or a combination of these either in a single tether, a composite tether, or a plurality of tissue tethers that extend in parallel and/or may be woven or bonded together. In certain embodiments, a tether may be long and thin. In certain embodiments, a tether may be planar and/or may be elastic or inelastic (rigid). Examples of a tether include, but are not limited to, a thread, a string, a polymer thread or line, a tendon graft, a ligament graft, a hamstring graft, soft tissue, a tendon, a ligament, a suture, suture tape, a woven tether, a fibrous material, a cord, and/or any of these in combination with each other, and the like. As used herein, an "anchor" refers to an apparatus, instrument, structure, member, part, device, component, system, or assembly structured, organized, configured, designed, arranged, or engineered to secure, retain, stop, and/or hold, an object to or at a fixed point, position, or location. Often, an anchor is coupled and/or connected to a flexible member such as a tether, chain, rope, wire, thread, suture, suture tape, or other like object. Alternatively, or in addition, an anchor may also be coupled, connected, and/or joined to a rigid object or structure. In certain embodiments, an anchor can be a fixation device. Said another way, a fixation device can function as an anchor.

Figure 5K:
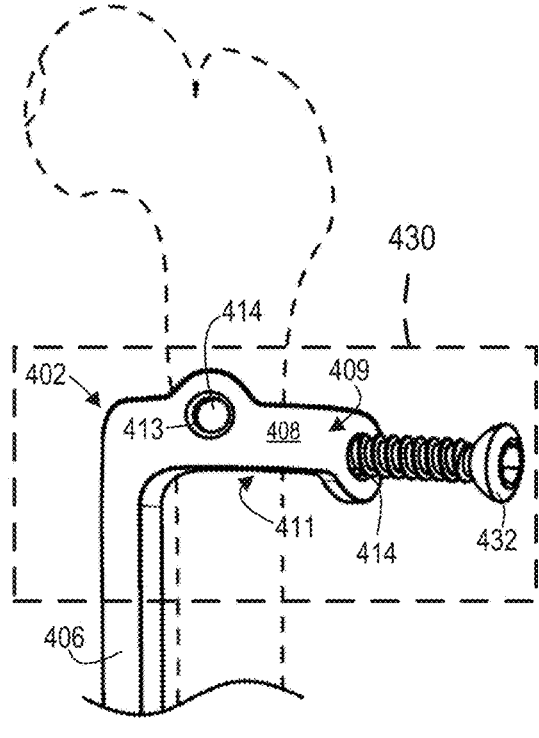
FIG. 5K is a close-up view of a bone plate deployed on a long bone, according to one embodiment.
Figure 5L:
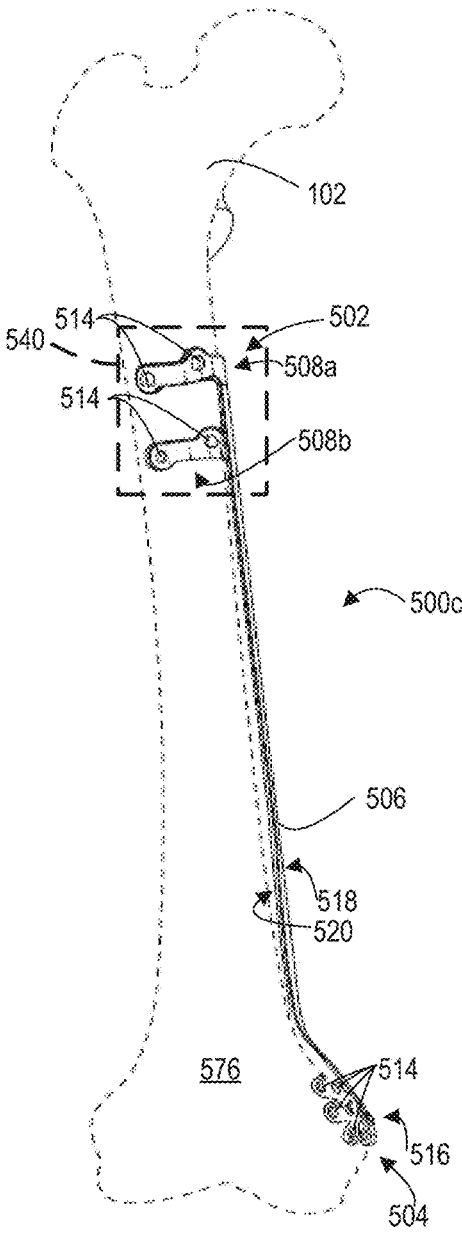
FIG. 5L is a perspective posterior view of a medial bone plate deployed on a long bone, according to one embodiment.

FIG. 5K is a close-up view of a bone plate deployed on a long bone, according to one embodiment. FIG. 5K illustrates one example of a low-profile fixation assembly 430. The low-profile fixation assembly 430 includes an arm 408, at least one fastener 432, and at least one fastener opening 414. The arm 408 may include a superior surface 409 that faces away from the long bone and an inferior surface 411 that faces a side of the long bone when the bone plate 400 is in use.

In one embodiment, the arm 408 extends from the body 406 in either an anterior direction (towards an anterior side of a bone when the bone plate 400 is in use) or in a posterior direction (towards a posterior side of a bone when the bone plate 400 is in use). The fastener 432 is configured to engage with the arm 408 to fixate the proximal end 402 to the long bone. In one embodiment, the fastener 432 may create its own opening in the arm 408 (self-tapping).

In one embodiment, the fastener opening 414 extends through the arm 408 from the superior surface 409 to the inferior surface 411. The fastener opening 414 may include internal threads 413. In one embodiment, the fastener 432 includes external threads 415 that engage a side (different from a side faced by the bone-facing surface 420 of the body 406) of the long bone (the fastener opening 414 may not include internal threads). The external threads 415 may also engage the internal threads 413 of the fastener opening 414 in embodiments that include internal threads 413.

In one embodiment, the fastener 432 engages the fastener opening 414 by passing first through the fastener opening 414 and then into a side of the long bone. In other words, the fastener 432 may be deployed from a side of the long bone faced by the superior surface 409.

In another embodiment, the fastener 432 engages the fastener opening 414 by passing first through a side other than a side faced by the bone-facing surface 420 of the body 406, then through a side faced by the superior surface 409 and then into the fastener opening 414. For example, the fastener 432 may pass through a side opposite the side faced by the superior surface 409, then into the side faced by the superior surface 409, and then into the fastener opening 414. In one example, the fastener 432 may pass through a posterior side of the long bone, then into an anterior side of the long bone, and then into the fastener opening 414. Those of skill in the art will appreciate that the arm 408 may extend from the 406 out over one or more sides of the long bone.

FIG. 5L is a perspective posterior view of a medial bone plate 500c deployed on a long bone, according to one embodiment. The medial bone plate 500c includes a low-profile fixation assembly 540. The embodiment of FIG. 5L may be similar to the embodiment of FIG. 5A in that the medial bone plate 500c includes two arms (e.g., first arm 508a, second arm 508b). As in FIG. 5K, the second arm 508b, like the first arm 508a, may include a superior surface 409 that faces away from long bone and an inferior surface 411 that faces a side different from the side faced by the bone-facing surface 420/520 of the body 406/506. The second arm 508b and/or the first arm 508a may each extend in one of an anterior direction and a posterior direction or both in the same direction. In the illustrated embodiment, the first arm 508a extends in a posterior direction (out over, or around, or above, the posterior side 576 of the bone) and the second arm 508b extends in an anterior direction (out over, or around, or above, the posterior side 576 of the bone) when the medial bone plate 500c is in use. One or more fasteners may engage with the first arm 508a and/or the second arm 508b to fixate the medial bone plate 500c to the long bone.

In the illustrated embodiment, the first arm 508a may extend around to a posterior side of the long bone. Accordingly, the first arm 508a may be referred to as posterior arm and may include posterior fastener opening. A posterior fastener may engage the posterior fastener opening 514.

Similarly, the second arm 508b may extend around to an anterior side of the long bone. Accordingly, the second arm 508b may be referred to as an anterior arm and may include an anterior fastener opening 514. An anterior fastener may engage the anterior fastener opening 514.

Figure 5M:
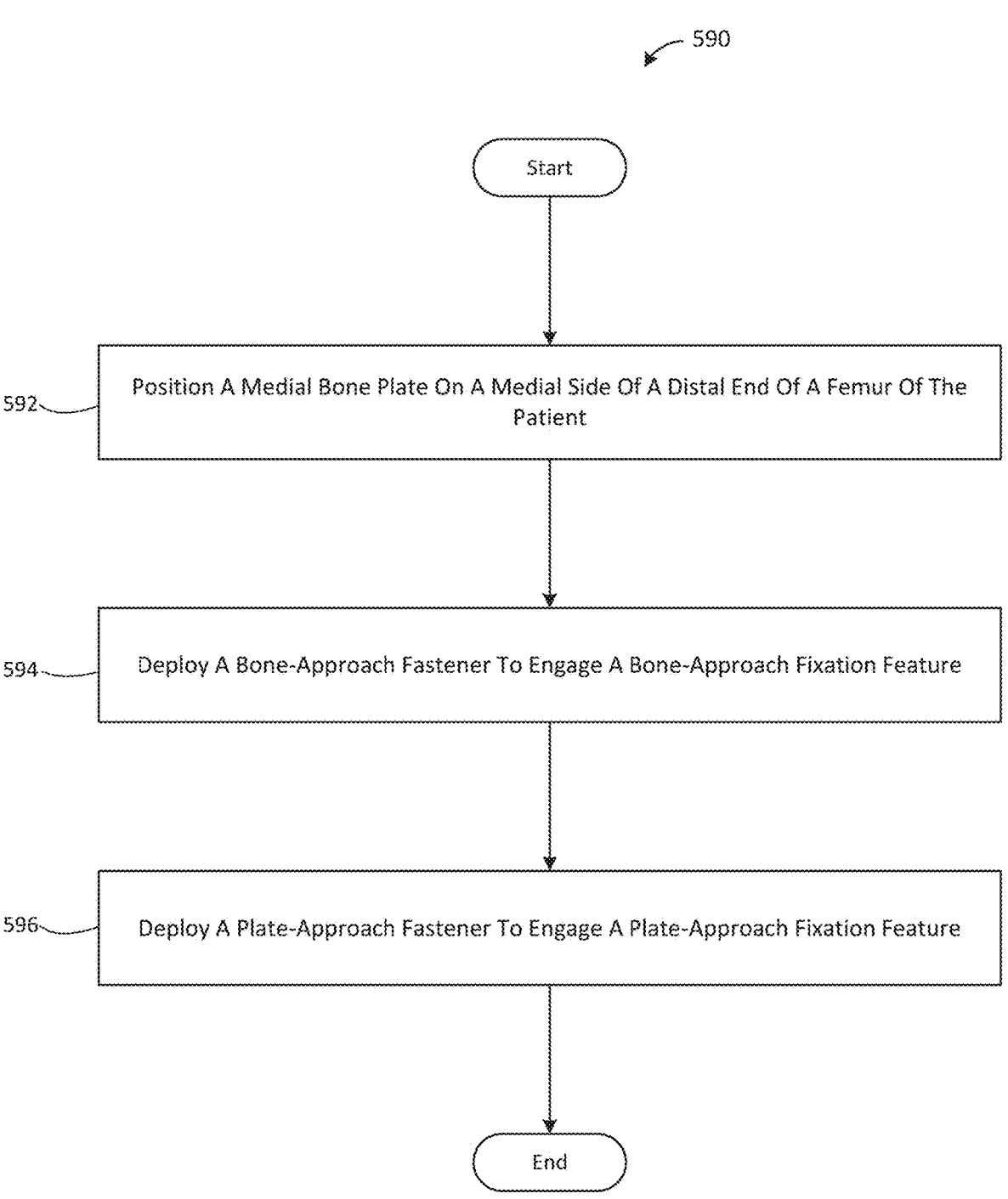
FIG. 5M illustrates one example of a method for deploying a medial bone plate according to one embodiment.

FIG. 5M illustrates one example of a method 590 for deploying a medial bone plate on a distal end of a femur of a patient according to one embodiment. Referring now to FIGS. 5B and 5M, in certain embodiments, the method 590 begins with a user positioning 592 a medial bone plate 500b on a medial side 570 of a distal end of a femur 102 of the patient. In certain embodiments, the user positions the medial bone plate 500b by sliding the medial bone plate 500b retrograde and percutaneously from a medial incision near the distal end of the femur 102 toward the proximal end of the femur 102. Thus in certain embodiments, the method 590 may include opening skin of the patient proximal to a distal end of the femur 102 and percutaneously sliding the medial bone plate 500b along the medial side 570 of the femur 102 with parts of the femur 102 in reduction. Of course, a surgeon may position the medial bone plate 500b using other techniques and steps.

In one embodiment, the medial bone plate 500b may be slid along the medial cortex surface of the femur 102. Once the distal end 504 of the medial bone plate 500b rests above, or against, the medial epicondyle of the femur 102.

In one embodiment, the medial bone plate 500b may include a body 506 that includes a proximal end 502, a distal end 504, a superior surface 518 that faces away from the femur 102, and a bone-facing surface 520 that faces the medial side 570 of the femur 102 once the medial bone plate 500b is positioned. In this embodiment, the medial bone plate 500b may include a bone-approach fixation feature and a plate-approach fixation feature near the distal end 504 that includes one or more fastener openings 514. The distal fixation feature 516 is one example of a plate-approach fixation feature. The low-profile fixation assembly 560 is one example of a bone-approach fixation feature. As explained above, a bone-approach fixation feature is a fixation feature in which one or more parts of the fixation system/assembly are deployed, on, in, around, or through bone before the part(s) engage and perform the fixation. Likewise, a plate-approach fixation feature is a fixation feature in which one or more parts of the fixation system/ assembly are deployed, on, in, around, or through a bone plate before the part(s) engage bone and perform the fixation.

In the illustrated embodiment of the method 590, next, a surgeon may deploy 594 a bone-approach fastener (e.g., low-profile fixation assembly 560) to engage (or fixate) the bone-approach fixation feature. In one example embodiment, this may be done by driving a bone-approach fastener (e.g., lateral approach fastener 528) through one of a lateral side, an anterior side, and a posterior side of the femur 102. Said another way, a surgeon may drive a bone-approach fastener through a side of the bone (e.g., femur 102) other than the medial side 570, the side with the medial bone plate 500b. After the bone-approach fastener is driven through a side of the bone, the bone-approach fastener may engage a bone-approach fixation feature (e.g., lateral approach fastener opening 526) to complete deployment of the bone-approach fastener. It should be noted that a bone-approach fastener will generally engage, pass through, or interact with bone before engaging with other aspects of a fixation assembly.

Next, a surgeon may deploy 596 one or more plate-approach fasteners to engage the plate-approach fixation feature. This can be accomplished for example by driving the plate-approach fastener through the medial bone plate 500*b* and into the medial cortex of the femur 102. In certain embodiments, the plate-approach fastener may be driven through fastener openings 514 of a distal fixation feature 516. Alternatively, or in addition, the plate-approach fastener may be driven through the body 506 forming its own opening and into the epicondyle. After a surgeon deploys 596 one or more plate-approach fasteners, the method may end.

In certain embodiments, deployment of bone-approach fasteners to engage bone-approach fixation features may include opening skin of the patient on a side of the femur that aligns with the bone-approach fixation feature and deploying a K-wire through the skin opening to serve as a guide for the bone-approach fastener. In one embodiment, driving the bone-approach fastener includes driving the bone-approach fastener over a deployed K-wire.

Figure 6A:
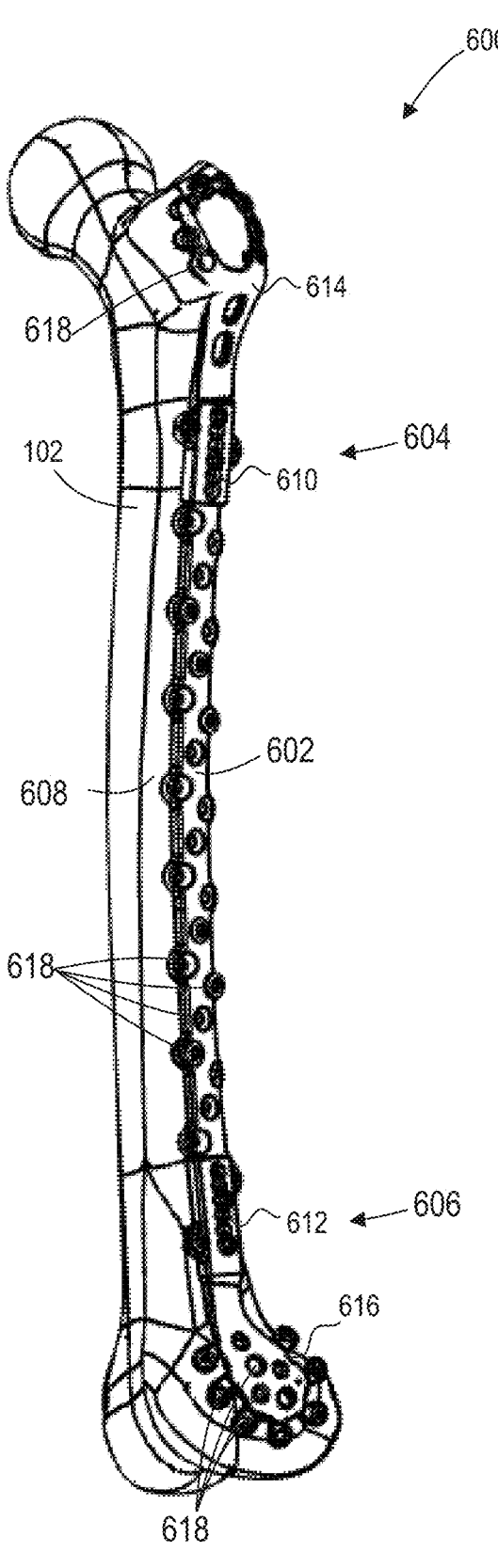
FIG. 6A is a perspective view of a lateral bone plate deployed on a long bone, according to one embodiment.
Figures 6B, 6C, 6D, 6E:
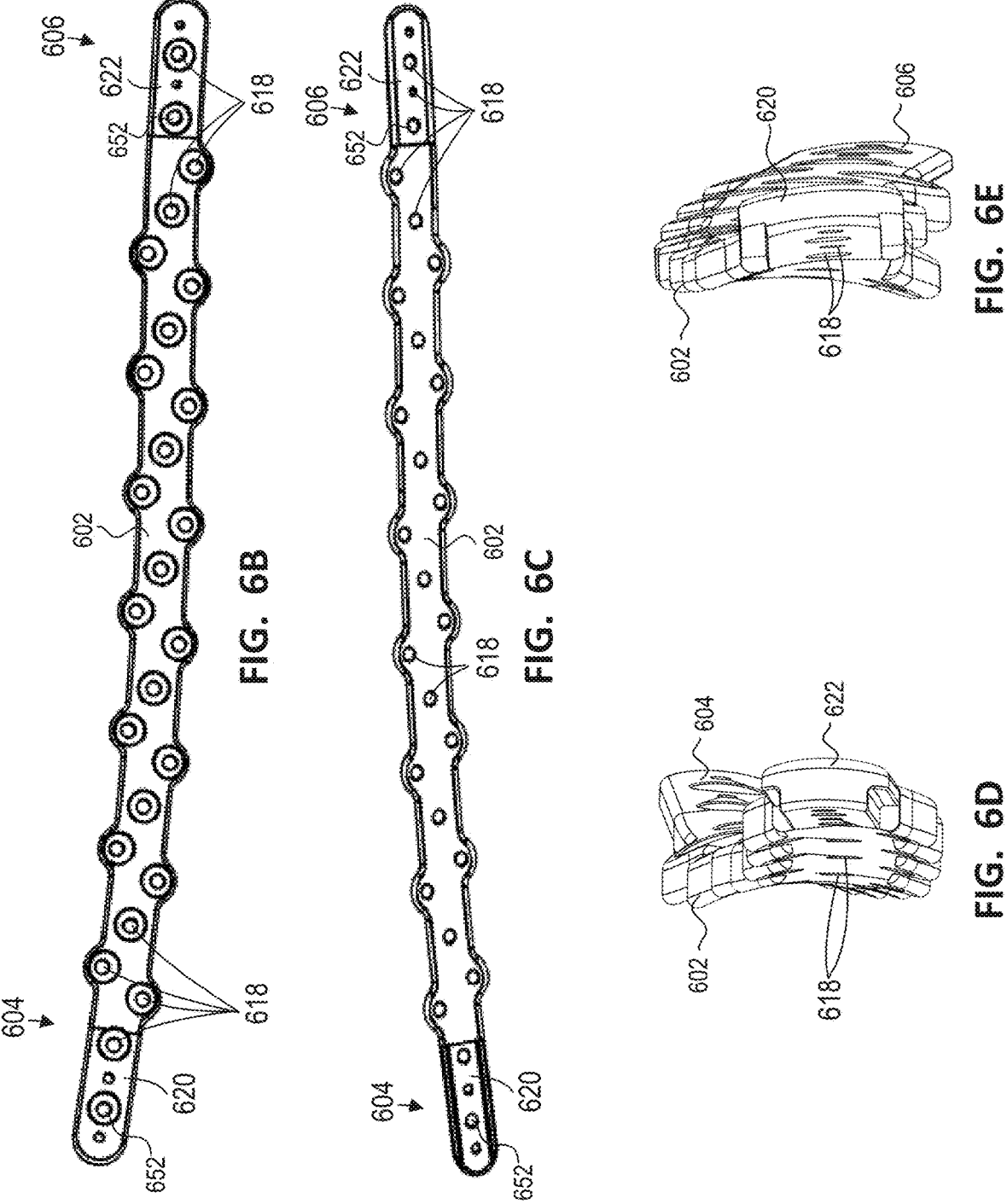
FIGS. 6B, 6C, 6D, 6E, 6F, and 6G are front view, rear view, distal end view, proximal end view, left side view, and right side view respectively of the lateral bone plate of FIG. 6A, according to one embodiment.
Figures 6F, 6G:
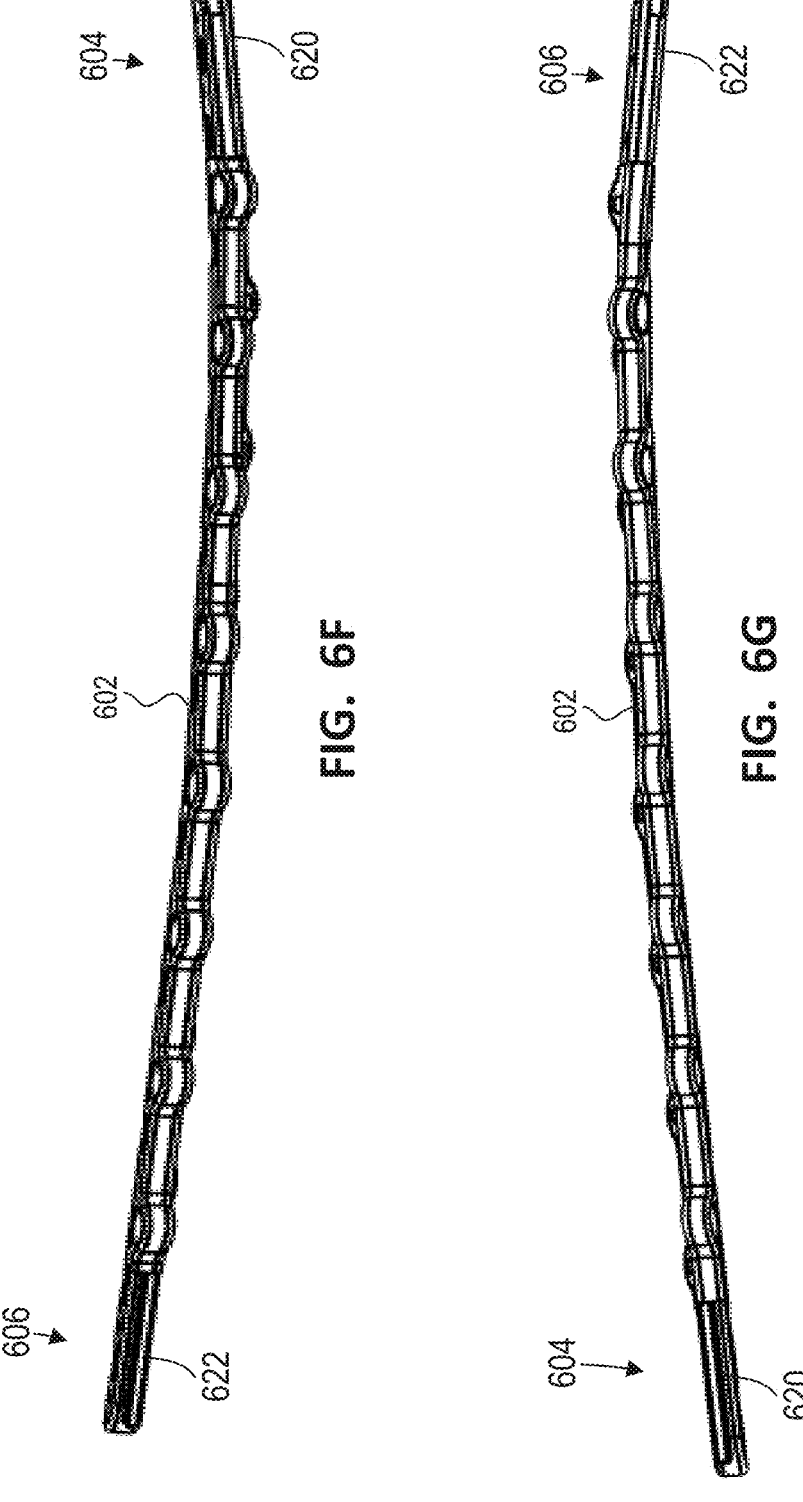

FIG. 6A is a perspective view of a lateral bone plate 600 deployed on a long bone, such as a femur 102, according to one embodiment. The lateral bone plate 600 includes a body 602, a proximal end 604, and a distal end 606. The body 602 is configured to contact a lateral surface of a shaft 608 of a long bone, such as a femur 102. The proximal end 604 of the lateral bone plate 600 includes a first connector 610 and the distal end 606 of the lateral bone plate 600 includes a second connector 612.

The body 602 and/or first connector 610 and/or second connector 612 may be manufactured to have a variety of lengths, widths, and/or thicknesses that may each individually and/or collectively be based on a variety of factors. Such factors may include but are not limited to patient age, gender, health condition, the facture type and position, the long bone type, and the like.

In certain embodiments, the lateral bone plate 600 may include a single connector: either a first connector 610 or a second connector 612. The first connector 610 and/or second connector 612 can engage, or be connected to, a corresponding extender. In the illustrated embodiment, the first connector 610 can be connected to a proximal extender 614 and the second connector 612 can be connected to a distal extender 616.

The connectors 610, 612 enable the lateral bone plate 600 to be adaptable to a variety of different fixation needs or configurations for a patient for which a surgeon has decided to use an intramedullary nail, such as embodiments of the lateral bone plate 600. The connectors 610, 612 enable the lateral bone plate 600 to be considered a modular lateral bone plate 600 that can accommodate a variety of needs and deployment scenarios.

FIGS. 6B, 6C, 6D, 6E, 6F, and 6G are front view, rear view, distal end view, proximal end view, left side view, and right side view respectively of the lateral bone plate of FIG. 6A, according to one embodiment. The lateral bone plate 600 can include a plurality of fastener openings 618. The plurality of fastener openings 618 may be positioned at a variety of locations along a length of the lateral bone plate 600, including on, or within, one or more extenders (e.g., proximal extender 614 and/or distal extender 616). Alternatively, or in addition, the plurality of fastener openings 618 may be included in one or more of the connectors (e.g., first connector 610 and/or second connector 612). The figures include multiple examples of one or more fastener openings 618, not all of which are identified with a reference numeral to aide in readability of the figures. In addition, a user may include one or more fasteners along a length of the lateral bone plate 600 with a head of the fastener impinging (i.e. pinching) the lateral bone plate 600 against a cortex of the bone.

Alternatively, or in addition, the body 602, first connector 610, second connector 612, proximal extender 614, and/or distal extender 616 may not include one or more openings such as fastener opening 618. Instead, the body 602, first connector 610, second connector 612, proximal extender 614, and/or distal extender 616 may be made from a material that permits a fastener to penetrate the body 602, first connector 610, second connector 612, proximal extender 614, and/or distal extender 616 and thereby tap its own opening.

In certain embodiments, the connectors (e.g., first connector 610 and/or second connector 612) can include two parts: one part connected to the lateral bone plate 600 and another part connected to an extender. For example, FIGS. 6B-6E illustrate a proximal plate part 620 connected to a proximal end 604 of the lateral bone plate 600 and a distal plate part 622 connected to a distal end 606 of the lateral bone plate 600.

Figure 7:
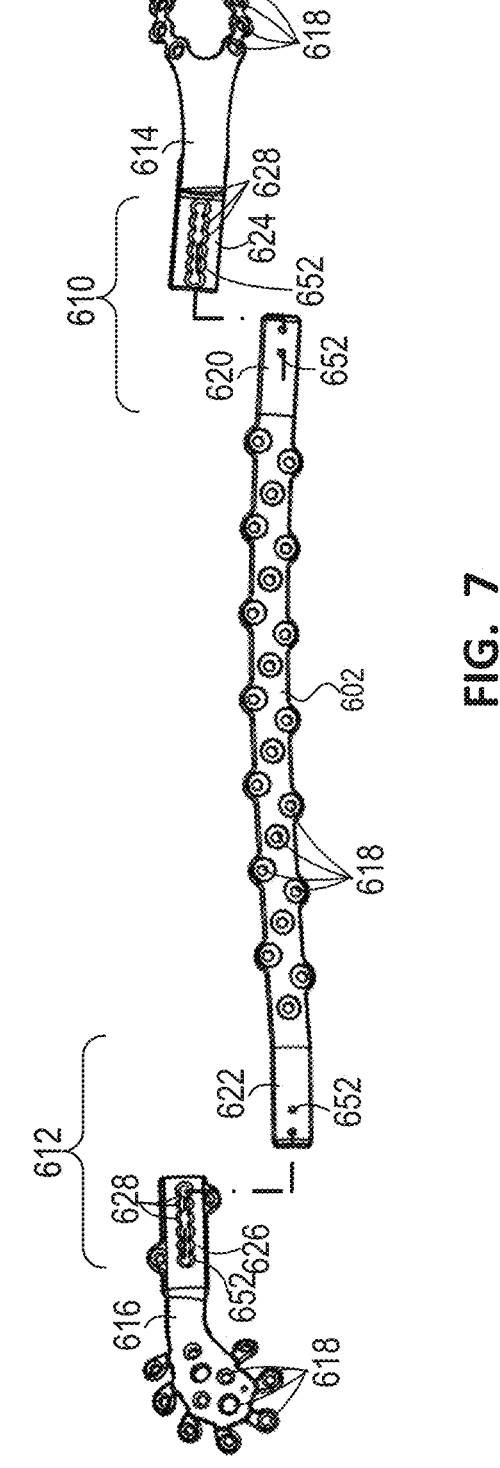
FIG. 7 is an exploded view of the lateral bone plate of FIG. 6A and two extenders, according to one embodiment.

FIG. 7 is an exploded view of the lateral bone plate 600 of FIG. 6A and proximal extender 614 and a distal extender 616, according to one embodiment. FIG. 7 illustrates how the proximal extender 614 and/or distal extender 616 can connect to the lateral bone plate 600 using connectors (e.g., first connector 610 and/or second connector 612) for a variety of fixation needs of a patient. In certain embodiments, the first connector 610 includes a proximal plate part 620 of the lateral bone plate 600 and a proximal extender part 624 of the proximal extender 614 and the second connector 612 includes a distal plate part 622 of the lateral bone plate 600 and a distal extender part 626 of the distal extender 616.

Those of skill in the art will recognize that a variety of different connector designs may be used for one or more of the connectors. Each of these designs is within the scope of the present disclosure. In the illustrated embodiment, the first connector 610 and second connector 612 are configured such that the parts of the lateral bone plate 600 slidably engage with the corresponding part of the extender (e.g., proximal extender 614/distal extender 616). In certain embodiments, the connectors are configured such that the extenders can be positioned at various positions longitudinally along the lateral surface of the long bone, (e.g., femur 102). FIG. 7 illustrates extenders that include a plurality of fastening positions 628 within a slot of each of the extenders.

The extenders (e.g., proximal extender 614 and/or distal extender 616) may be used as primary fixation devices each alone or in combination with a body 602. For example, a proximal extender 614 can be used without a body 602 or a distal extender 616. Similarly, distal extender 616 can be used without a body 602 or a proximal extender 614. The body 602 can be used with one of the distal extender 616 and the proximal extender 614. Or, a distal extender 616 and a proximal extender 614 can be used without a body 602. Alternatively, or in addition, the extenders may be used to provide secondary/supplemental fixation together with other fixation devices/techniques for fixation regardless of a position of a fracture (i.e., mid, distal, proximal sections of a long bone) or the type of bone (e.g., femur, tibia, humerus, etc.). In addition, one or more extenders may be used together with an intramedullary nail assembly 100 or intramedullary nail system 200 without the body 602.

FIGS. 8A, 8B, 8C, 8D, 8E, and 8F are front view, rear view, bottom view, top view, right side view, and left side view respectively of a distal extender, according to one embodiment. As explained above, the distal extender 616 may include a plurality of fastener openings 618 configured to receive a variety of different fasteners, such as bone fasteners. The diameters of the plurality of fastener openings 618 may each be the same or may be different among the plurality of fastener openings 618.

In one embodiment, the distal extender 616 may include a slot 630 that passes through the distal extender part 626. The slot 630 may serve to accept a fastener that secures the distal extender part 626 to a corresponding distal plate part 622 when the lateral bone plate 600 and distal extender 616 are deployed together. In one embodiment, the distal extender part 626 and distal plate part 622 can be secured to each other through the slot 630 and a set screw (see FIG. 14A) that may engage threads of a fastener opening in the distal plate part 622. Advantageously, the slot 630 enables an operator to position the distal extender 616 relative to the lateral bone plate 600 at an almost infinite number of positions along the slot 630. In this manner, a user can adapt a lateral bone plate 600 and distal extender 616 to particular needs of a patient and/or a fixation scenario.

Figures 8A, 8B, 8C, 8D:
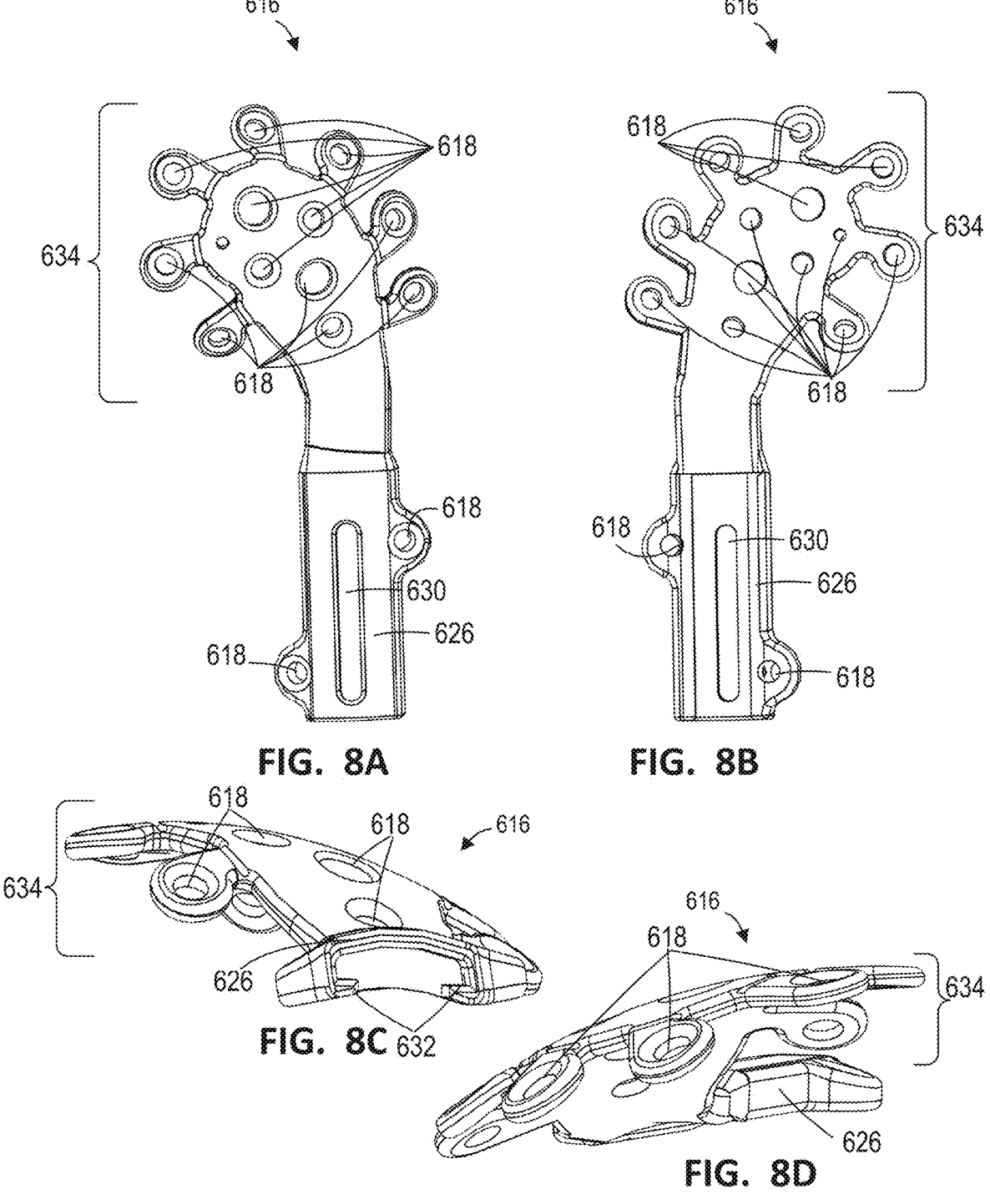

FIG. 8C illustrates one example of how the distal extender part 626 can slidably engage with the distal plate part 622. The distal extender part 626 can include a pair of lips 632 that slidably engage the distal plate part 622 when the two parts are joined.

The distal extender 616 may include one or more fixation features 634. The fixation feature 634 is a section of the distal extender 616 contoured and/or configured to conform to the contour of a portion of a surface of cortex bone adjacent to the distal extender 616 once the distal extender 616 is deployed on a lateral surface of a long bone (e.g., a distal end of the lateral surface of a femur 102). Consequently, the configuration, size, and shape of the fixation feature 634 may vary depending on where the distal extender 616 is installed. In one embodiment, the fixation feature 634 is contoured to engage with, and/or contact a surface of a lateral condyle of a long bone, such as a femur 102.

FIGS. 9A, 9B, 9C, 9D, 9E, and 9F are front view, rear view, bottom view, top view, right side view, and left side view respectively of a proximal extender, according to one embodiment. As explained above, the proximal extender 614 may include a plurality of fastener openings 618 configured to receive a variety of different fasteners, such as bone fasteners. The diameters of the plurality of fastener openings 618 may each be the same or may be different among the plurality of fastener openings 618.

In one embodiment, the proximal extender 614 may also include a slot 630 that passes through the proximal extender part 624. The slot 630 may serve to accept a fastener that secures the proximal extender part 624 to a corresponding proximal plate part 620 when the lateral bone plate 600 and proximal extender 614 are deployed together. In one embodiment, the proximal extender 614 and proximal plate part 620 can be secured to each other through the slot 630 and a set screw (see FIG. 14A) that may engage threads of a fastener opening in the proximal plate part 620. Advantageously, the slot 630 enables an operator to position the proximal extender 614 relative to the lateral bone plate 600 at an almost infinite number of positions along the slot 630. In this manner, a user can adapt a particular lateral bone plate 600 and proximal extender 614 to particular needs of a patient and/or a fixation scenario.

Figures 9C, 9D, 9E, 9F:
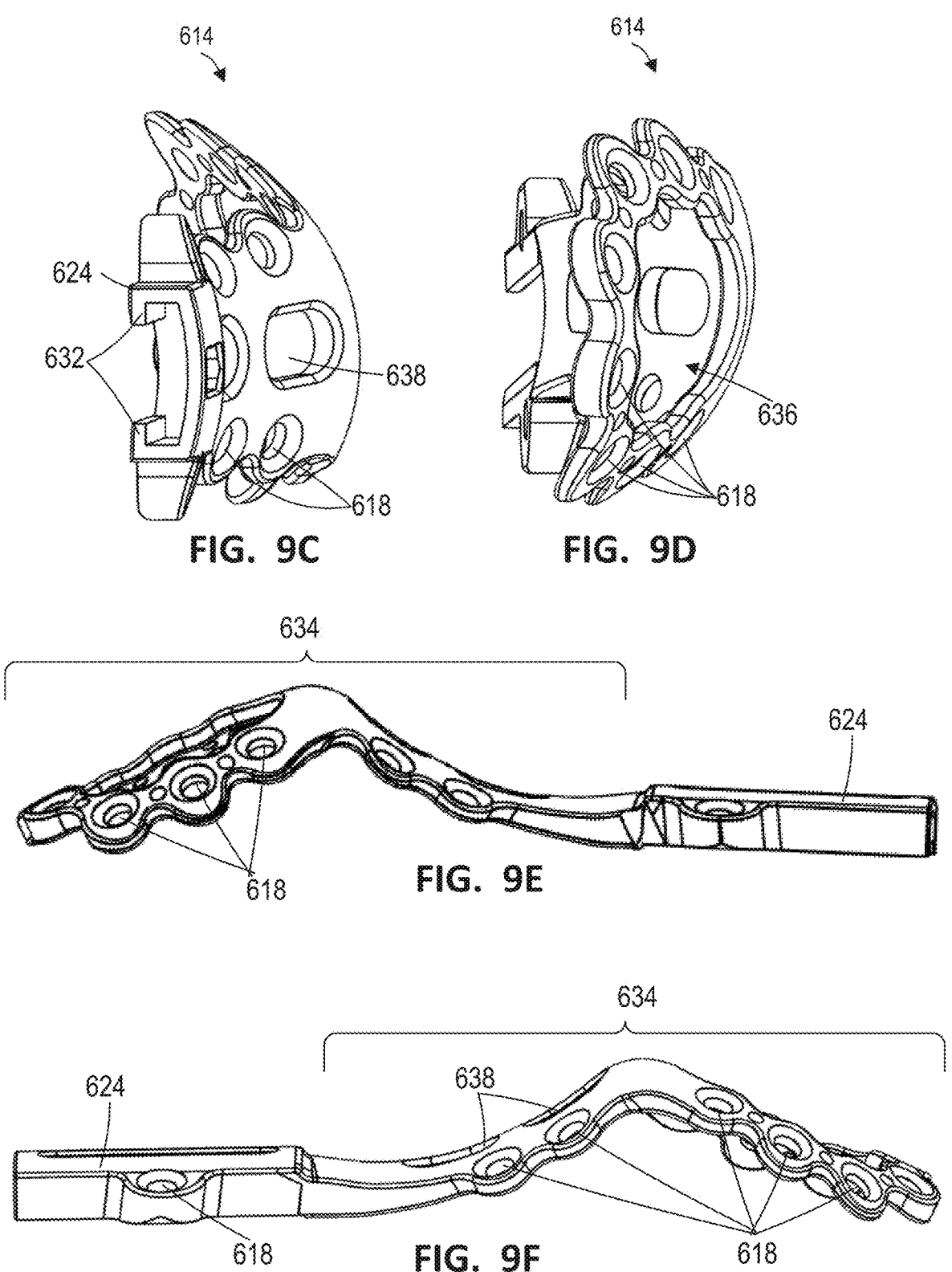

FIG. 9C illustrates one example of how the proximal extender part 624 can slidably engage with the proximal plate part 620. The proximal extender part 624 can include a pair of lips 632 that slidably engage the proximal plate part 620 when the two parts are joined.

The proximal extender 614 may include one or more fixation features 634. The fixation feature 634 is a section of the proximal extender 614 contoured and/or configured to conform to the contour of a portion of a surface of cortex bone adjacent to the proximal extender 614 once the proximal extender 614 is deployed on a lateral surface of a long bone (e.g., a proximal end of the lateral surface of a femur 102). Consequently, the configuration, size, and shape of the fixation feature 634 may vary depending on where the proximal extender 614 is installed. In one embodiment, the fixation feature 634 is contoured to engage with, and/or contact a surface of an upper extremity such a surface alongside the gluteal tuberosity and/or a greater trochanter of a long bone, such as a femur 102.

In one embodiment, the proximal extender 614 may also include a top opening 636 and one or more neck openings 638. The top opening 636 may serve to reduce the size, weight, and surface area of the fixation feature 634 that covers a part of the long bone. Furthermore, the top opening 636 can be configured to provide structural support and rigidity to the fixation feature 634. The size and shape of the top opening 636 can vary in different embodiments of the proximal extender 614.

The neck openings 638 may also serve to reduce the size, weight, and surface area of the proximal extender 614 that covers a part of the long bone. Furthermore, the neck openings 638 can be configured to provide structural support and rigidity to a neck section of the proximal extender 614. The size and shape of the neck openings 638 can vary in different embodiments of the proximal extender 614. In one embodiment, the neck openings 638 are oval shaped.

FIGS. 10A, 10B, 10C, and 10D are front view, rear view, bottom view, top view respectively of a proximal extender, according to one embodiment. As explained above, the proximal extender 640 may include a plurality of fastener openings 618 configured to receive a variety of different fasteners, such as bone fasteners. The diameters of the plurality of fastener openings 618 may each be the same or may be different among the plurality of fastener openings 618.

In one embodiment, the proximal extender 640 may also include a multi-position slot 642 that passes through a proximal extender part 644. The multi-position slot 642 may serve to accept a fastener that secures the proximal extender part 644 to a corresponding proximal extender part 644 when the lateral bone plate 600 and proximal extender 640 are deployed together. In one embodiment, the proximal extender 640 and proximal extender part 644 can be secured to each other through the multi-position slot 642 and a set screw (see FIG. 14A) that may engage threads of a fastener opening or another opening in the proximal plate part 620. Advantageously, the multi-position slot 642 enables an operator to position the proximal extender 640 relative to the lateral bone plate 600 using one or more predefined positions along the multi-position slot 642. In this manner, a user can adapt a particular lateral bone plate 600 and proximal extender 640 to particular needs of a patient and/or a fixation scenario.

Figures 10A, 10B, 10C, 10D:
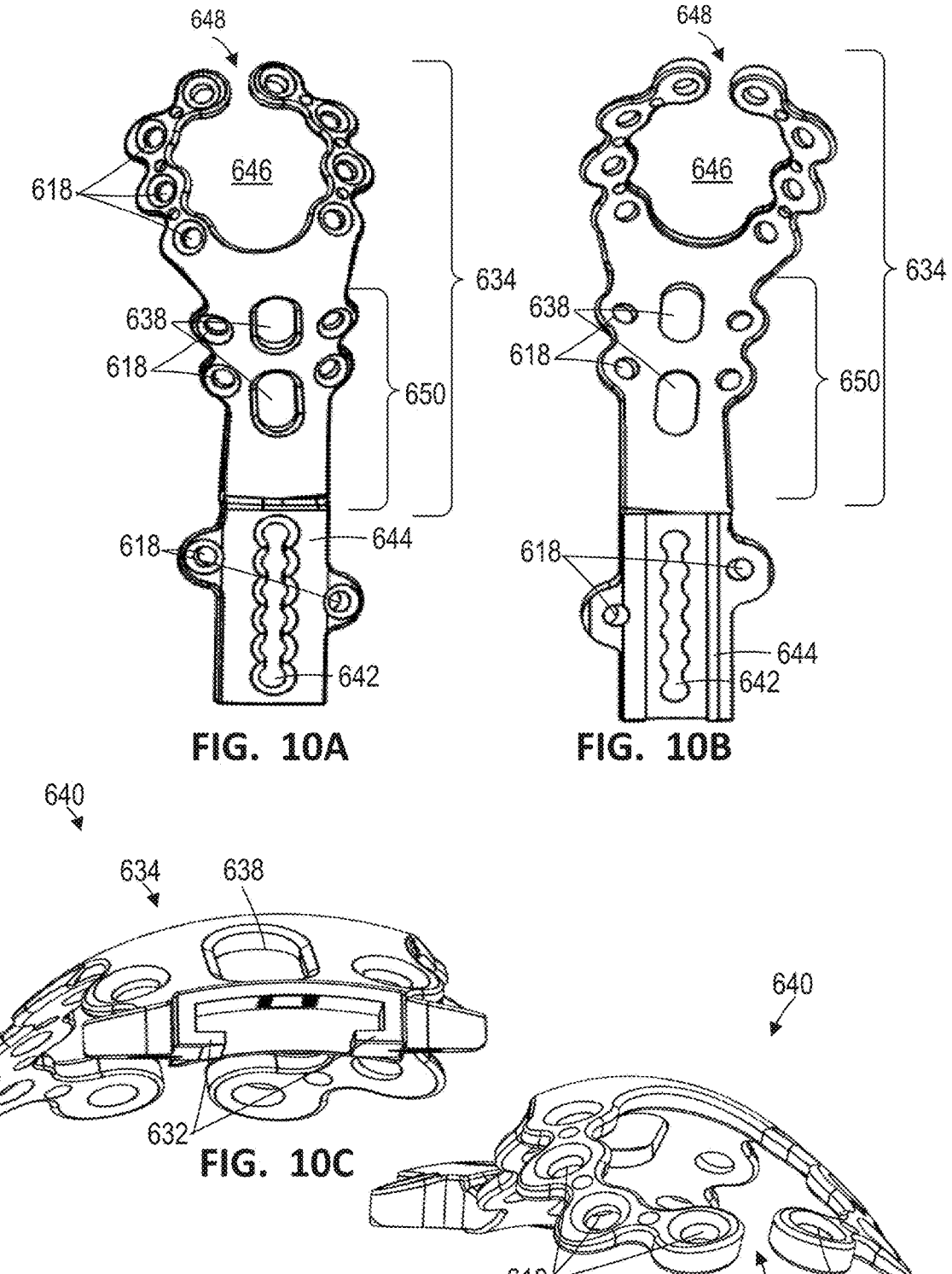
FIGS. 10A, 10B, 10C, and 10D are front view, rear view, bottom view, and top view, respectively of a proximal extender, according to one embodiment.
Figures 11A, 11B:
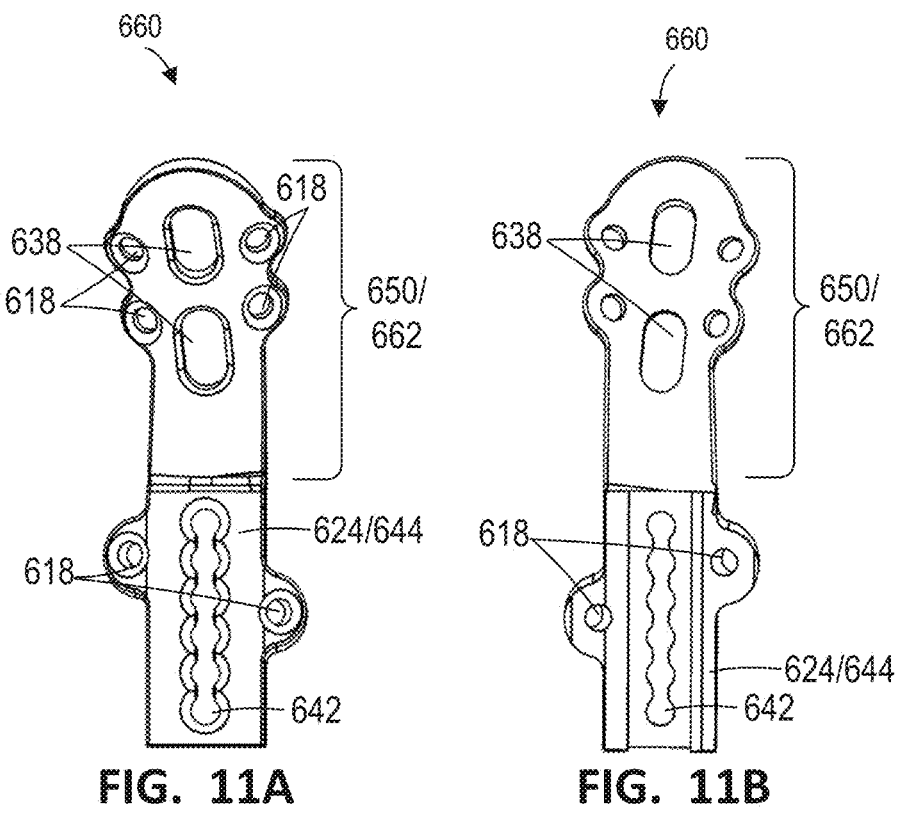
FIGS. 11A, 11B, 11C, 11D, 11E, and 11F are front view, rear view, bottom view, top view, right side view, and left side view respectively of a proximal extender, according to one embodiment.
Figures 11C, 11D:
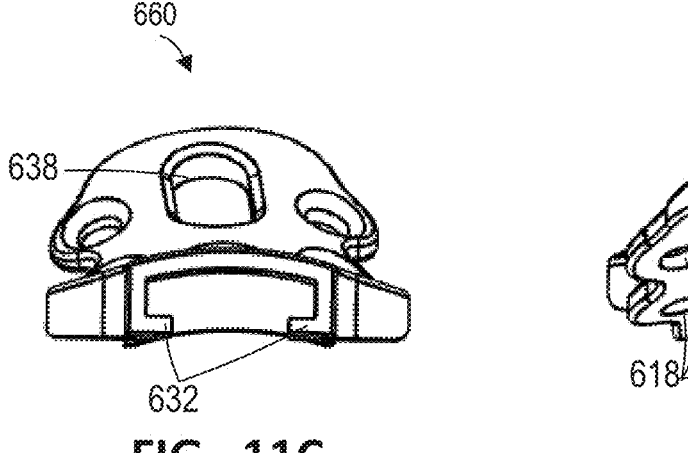
Figures 11E, 11F:
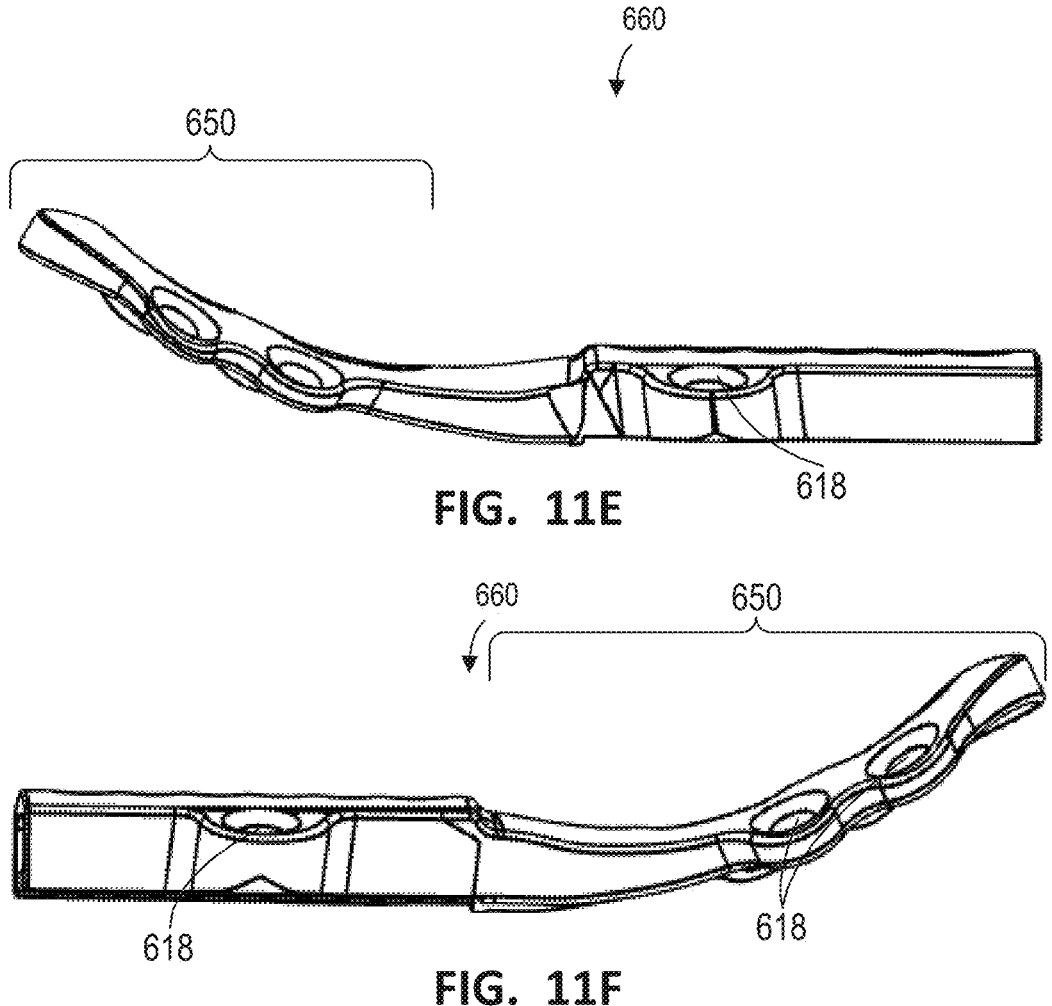

FIG. 10C illustrates one example of how the proximal extender part 644 can slidably engage with the proximal plate part 620. The proximal extender part 644 can include a pair of lips 632 that slidably engage the proximal plate part 620 when the two parts are joined.

The proximal extender 640 may include one or more fixation features 634. The fixation feature 634 is a section of the proximal extender 640 contoured and/or configured to conform to the contour of a portion of a surface of cortex bone adjacent to or in contact with the proximal extender 640 once the proximal extender 640 is deployed on a lateral surface of a long bone (e.g., a proximal end of the lateral surface of a femur 102). Consequently, the configuration, size, and shape of the fixation feature 634 may vary depending on where the proximal extender 640 is installed. In one embodiment, the fixation feature 634 is contoured to engage with, and/or contact a surface of an upper extremity such a surface alongside the gluteal tuberosity and/or a greater trochanter of a long bone, such as a femur 102.

In one embodiment, the proximal extender 640 may also include a top opening 646 and one or more neck openings 638. The top opening 646 may serve to reduce the size, weight, and surface area of the fixation feature 634 that covers a part of the long bone. Furthermore, the top opening 646 can be configured to provide structural support and rigidity to the fixation feature 634. The size and shape of the top opening 646 can vary in different embodiments of the proximal extender 640. In one embodiment, the top opening 646 can include an opening 648 between the fastener openings 618 of a fixation feature 634. The opening 648 may facilitate more flexibility in the positioning of parts of a fixation feature 634 during deployment.

The neck openings 638 may also serve to reduce the size, weight, and surface area of the proximal extender 614 that covers a part of the long bone. Furthermore, the neck openings 638 can be configured to provide structural support and rigidity to a neck section 650 of the proximal extender 640. The size and shape of the neck openings 638 can vary in different embodiments of the proximal extender 640. In one embodiment, the neck openings 638 are oval shaped.

FIGS. 11A, 11B, 11C, 11D, 11E, and 11F are front view, rear view, bottom view, top view, right side view, and left side view respectively of a proximal extender, according to one embodiment. The proximal extender 660 may have structures, features, and functions, operations, and configuration similar to that of the proximal extender 614 described in relation to FIG. 9A-9F and/or the proximal extender 640 described in relation to FIG. 10A-10D. Accordingly, the proximal extender 660 may include a proximal extender part 624/644, fastener openings 618, multi-position slot 642, a fixation feature 662, a neck section 650, neck openings 638, lips 632, and the like.

A main difference between the proximal extender 660 and the proximal extender 614 and/or proximal extender 640 may be a configuration of the fixation features. In FIGS. 11A-11F, the proximal extender 660 includes a fixation feature 662 that is smaller than the exemplary fixation features 634 of the proximal extender 614 and/or the proximal extender 640.

The present disclosure discloses surgical devices, systems, and/or methods for fixation in relation to fractures of a long bone of a patient. Existing fixators and/or fixation devices, methods, or steps for long bone fractures are limited.

It is desirable that bone plates be as thin, short, light weight, and flexible as possible. However, bone plates with such characteristics may provide sufficient limited torsional stiffness but insufficient bending stiffness of a long bone when used in isolation. Intramedullary nails may provide sufficient bending stiffness but limited torsional stiffness. A fixation system is needed that includes a thinner and/or more suitably flexible bone plate and an intramedullary nail that together provide the desired or sufficient bending stiffness and torsional stiffness of the long bone with a facture. It may also be desirable to minimizing thickness of the bone plate, that connects to a cortex of the long bone.

"Stiffness" refers to the extent to which an object, structure, device, component, member, system, or assembly resists deformation in response to an applied force. It should be noted that the elastic modulus of a material is not the same as the stiffness of a component made from that material. Elastic modulus is a property of the constituent material; stiffness is a property of a structure or component of a structure, and hence stiffness is dependent upon various physical dimensions that describe that component. That is, the modulus is an intensive property of the material; stiffness, on the other hand, is an extensive property of the solid body, object, structure, device, component, member, system, or assembly that is dependent on the material and its shape and boundary conditions. (Search "stiffness" on Wikipedia.com May 11, 2022. CC-BY-SA 3.0 Accessed Jul. 26, 2022. Modified.) Bending stiffness refers to a measure for stiffness of an object, structure, device, component, member, system, or assembly in relation to bending the object, structure, device, component, member, system, or assembly. Bending stiffness refers to a measure of how much or how far an object, structure, device, component, member, system, or assembly will bend before breaking, deforming, or failing. Torsional stiffness refers to a measure for stiffness of an object, structure, device, component, member, system, or assembly in relation to twisting or applying a torque to the object, structure, device, component, member, system, or assembly. Torsional stiffness refers to a measure of how much or how far an object, structure, device, component, member, system, or assembly will twist before breaking, deforming, or failing.

"Rigidity" refers to the quality or state of being rigid; want of pliability; the quality of resisting change of form; the amount of resistance with which a body opposes change of form. (Search "rigidity" on wordhippo.com. WordHippo, 2022. Web. Accessed 26 Jul. 2022.)

"Sufficient" refers to enough of any quantity, attribute, aspect, characteristic, feature, function, and/or functionality to meet a need, purpose, objective, metric, and/or goal (Search "sufficient" on wordhippo.com. WordHippo, 2022. Web. Modified Accessed 4 Aug. 2022.) In the context of a surgical procedure, instrument, system, assembly, construct, and/or implant, "Sufficient" can mean that the apparatus, system, and/or method provides a desired characteristic and/or for a requisite amount of time to promote and/or enable proper healing of anatomical structures of a patient.

"Insufficient" refers to an amount of any quantity, attribute, aspect, characteristic, feature, function, and/or functionality that fails to meet a need, purpose, objective, metric, and/or goal. Insufficient is generally the opposite of sufficient. (Search "sufficient" on wordhippo.com. WordHippo, 2022. Web. Modified Accessed 4 Aug. 2022.) In the context of a surgical procedure, instrument, system, assembly, construct, and/or implant, "Insufficient" can mean that the apparatus, system, and/or method fails to provide a desired characteristic and/or for a requisite amount of time to promote and/or enable proper healing of anatomical structures of a patient.

Figures 12A, 12B, 12C:
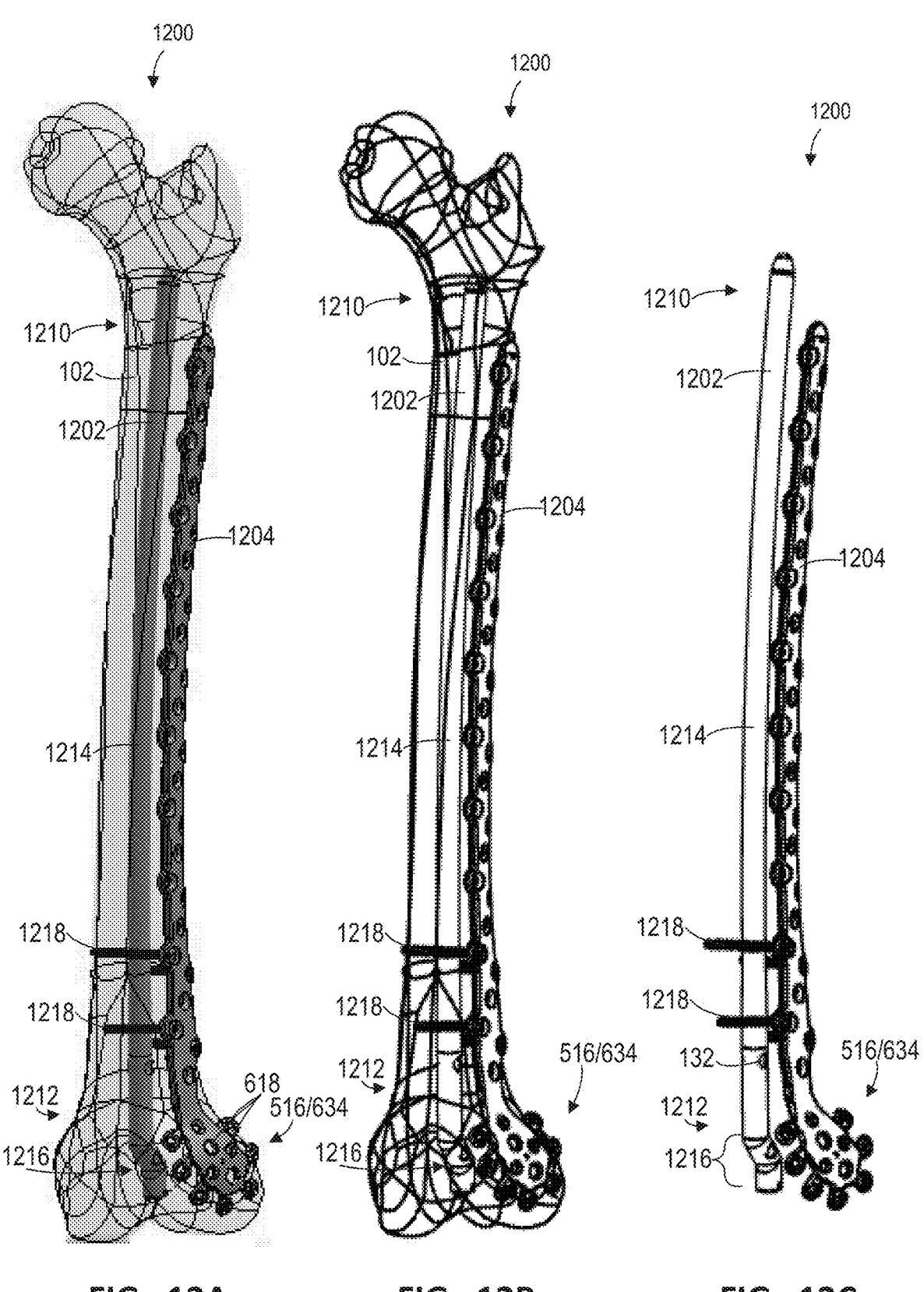
FIG. 12A is a perspective view of a lateral bone plate and intramedullary nail both deployed on and within a long bone, according to one embodiment.
FIG. 12B is a perspective view of the lateral bone plate and the intramedullary nail of FIG. 12A both deployed on and within a long bone, according to one embodiment.
FIG. 12C is a perspective view of the lateral bone plate and the intramedullary nail of FIG. 12A both positioned as when deployed on and within a long bone, with the long bone not shown for clarity, according to one embodiment.

FIG. 12A is a perspective view of a lateral bone plate and intramedullary nail both deployed on and within a long bone, such as a femur 102 according to one embodiment. FIG. 12B illustrates the fixation system 1200 of FIG. 12A deployed on and within a long bone using a line drawing and FIG. 12C illustrates the fixation system 1200 of FIG. 12A positioned as when deployed on and within a long bone without the long bone shown for clarity.

FIGS. 12A, 12B, and 12C illustrate a fixation system 1200 that includes an intramedullary nail 1202 and a bone plate 1204. The intramedullary nail 1202 and/or bone plate 1204 used in the fixation system 1200 may include one or more embodiments described herein or may be various other embodiments of an intramedullary nail 1202 and/or a bone plate 1204. For example, the intramedullary nail 1202 may be the intramedullary nail assembly 100 or intramedullary nail 202 or a different embodiment of an intramedullary nail. In one embodiment, the intramedullary nail 1202 is a straight intramedullary nail, one that does not have an offset section 116 on either end. Similarly, the bone plate 1204 may be the medial bone plate 500a, the lateral bone plate 600, a modular bone plate with one or more connectors for extenders, or a bone plate having a predefined length. In addition, the bone plate 1204 may include one or more fixation features 634 and/or one or more extenders.

Figure 12D:
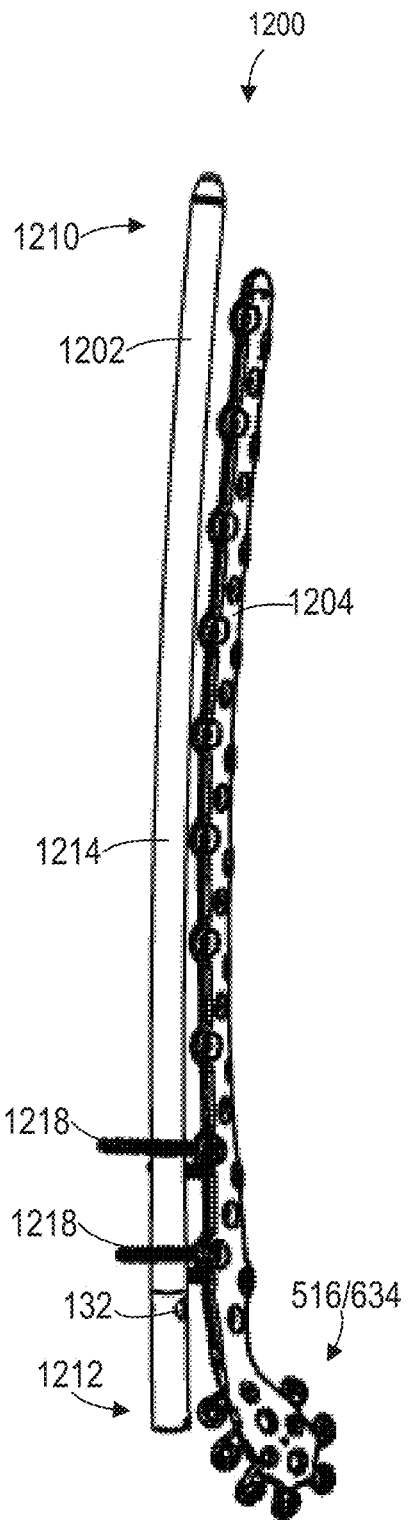
FIG. 12D is a perspective view of the lateral bone plate and an intramedullary nail both positioned as when deployed on and within a long bone, with the long bone not shown for clarity, according to one embodiment.

FIG. 12D is a perspective view of the lateral bone plate and an intramedullary nail both positioned as when deployed on and within a long bone, with the long bone not shown for clarity, according to one embodiment. FIG. 12D illustrates that the intramedullary nail 1202 can be one such as intramedullary nail 202 that is straight and does not include an offset section 116 or one that includes an offset section 116 (e.g., feature 1216) as illustrated in FIG. 12C.

Advantageously, the fixation system 1200 includes an intramedullary nail 1202 and bone plate 1204 that, each deployed alone, do not provide sufficient fixation of the long bone, but when deployed together do provide a desired level of fixation of the long bone. Because the intramedullary nail 1202 and bone plate 1204 are part of a fixation system 1200 that provides sufficient fixation when deployed, one or the other or both of the intramedullary nail 1202 and the bone plate 1204 can be made from more light weight, thinner, less expensive, lighter, and less rigid materials than if one or the other or both of the intramedullary nail 1202 and bone plate 1204 were used alone to provide fixation of the long bone.

In one embodiment, the intramedullary nail 1202 includes a proximal end 1210, a distal end 1212, and a shaft 1214. The proximal end 1210 corresponds to a proximal end of a long bone when the intramedullary nail 1202 is deployed. The distal end 1212 corresponds to a distal end of a long bone when the intramedullary nail 1202 is deployed. The shaft 1214 interconnects the proximal end 1210 and the distal end 1212.

In certain embodiments, the intramedullary nail 1202 also includes a feature 1216, or means for, deploying the intramedullary nail 1202 retrograde into the intramedullary canal from the distal end of the long bone. In one embodiment, the feature 1216 is configured to enable deployment of the intramedullary nail 1202 from the distal end of the long bone, where the long bone includes a knee prosthesis that covers or blocks, all or part of a medial condyle and/or a lateral condyle, and/or distal access to the intramedullary canal. The feature 1216 can be implemented in a variety of ways some examples of which have been included herein. For example, the section 116 may serve as the feature 1216. Alternatively, or in addition, the adapter 204 may serve as the feature 1216. Alternatively, or in addition, a driver of an inserter may be configured to serve as the feature 1216.

In one example embodiment, the bone plate 1204 is a lateral bone plate or a lateral modular bone plate configured to contact a lateral surface of the long bone. Alternatively, or in addition, the bone plate 1204 may be a bone plate 400, an anterior bone plate, a posterior bone plate, a superior bone plate, an inferior bone plate, or the like. In one embodiment, the bone plate 1204 can be configured to be thinner and less weight and more flexible than conventional bone plates because the bone plate 1204 is deployed as part of a fixation system 1200 that includes another fixation device (e.g., an intramedullary nail 1202). In certain embodiments, the bone plate 1204 is so thin and/or flexible that the bone plate 1204 provides insufficient fixation without another fixation system or device such as an intramedullary nail 1202. Advantageously, using a more flexible bone plate 1204 may promote, or at least not inhibit, desired bone healing in relation to one or more fractures. Alternatively, or in addition, the bone plate 1204 may be rigid or resilient.

Alternatively, or in addition, in one embodiment, the intramedullary nail 1202 can be configured to be thinner and less weight and more flexible than conventional intramedullary nails because the intramedullary nail 1202 is deployed as part of a fixation system 1200 that includes another fixation device (e.g., a bone plate 1204). In certain embodiments, the intramedullary nail 1202 is so thin, short, and/or flexible that the intramedullary nail 1202 provides insufficient fixation without another fixation system or device such as bone plate 1204. Advantageously, using a more flexible and/or light weight intramedullary nail 1202 may reduce costs, and/or promote, or at least not inhibit, desired bone healing in relation to one or more fractures.

The lateral bone plate may include one or more fastener openings 618. The lateral bone plate may also include one or more fixation features 516/634. The lateral bone plate may include one or more fasteners 1218 that may pass through the fastener openings 618 and engage the bone. Fasteners 1218 can also be used to lock the intramedullary nail 1202 to the bone by engaging openings 132 of the intramedullary nail 1202.

Figure 13:
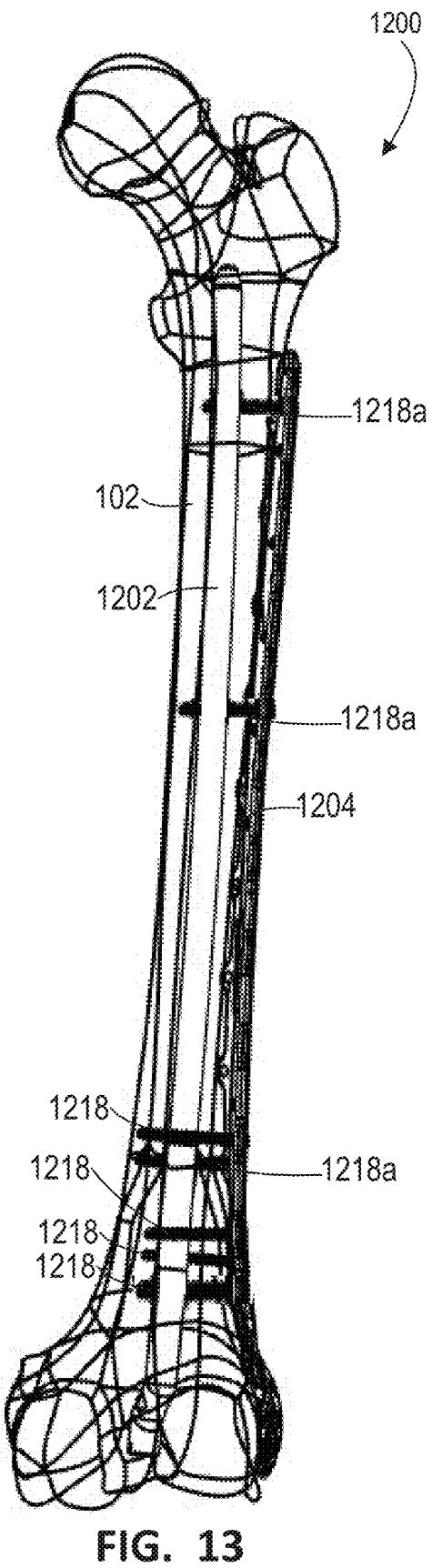
FIG. 13 is a perspective view of a lateral bone plate and intramedullary nail both deployed on and within a long bone, according to one embodiment.

FIG. 13 is a perspective view of a fixation system 1200 that includes a bone plate 1204, such as a lateral bone plate, and an intramedullary nail 1202 both deployed on and within a long bone, according to one embodiment. In certain embodiments, the flexible bone plate 1204 and intramedullary nail 1202 can be deployed on a long bone that includes a prosthesis such as a knee prosthesis, a hip prosthesis, and/or one or more fixation prosthesis. Alternatively, or in addition, the flexible bone plate 1204 and intramedullary nail 1202 can be deployed on a long bone that has no prosthesis (i.e., a native long bone, no joint or fixation prostheses). FIG. 13 illustrates that while one or more fasteners 1218 can be used to secure the intramedullary nail 1202 to the bone and/or the bone plate 1204 to the bone, one or more fasteners 1218 can also be used to secure the bone plate 1204 to the intramedullary nail 1202 (see fasteners 1218a). In one embodiment, a fastener can be driven through fastener openings 618 or tap its own opening in an intramedullary nail 1202 made of a material that accepts penetration by the fastener.

Referring now to FIGS. 12A-12C and 13, a method for deployment of the fixation system 1200 may include techniques for deployment of one of an intramedullary nail assembly 100 or intramedullary nail system 200 and deployment of a bone plate 400 and/or lateral bone plate 600, done in any order. In one embodiment, a surgeon may deploy an intramedullary nail assembly 100 or intramedullary nail system 200 followed by deployment of a lateral bone plate 600. As part of deploying the lateral bone plate 600, a surgeon may also deploy fasteners, or another fastening system, through the lateral bone plate 600 that engage or lock with the intramedullary nail assembly 100 or intramedullary nail system 200.

Figure 14C:
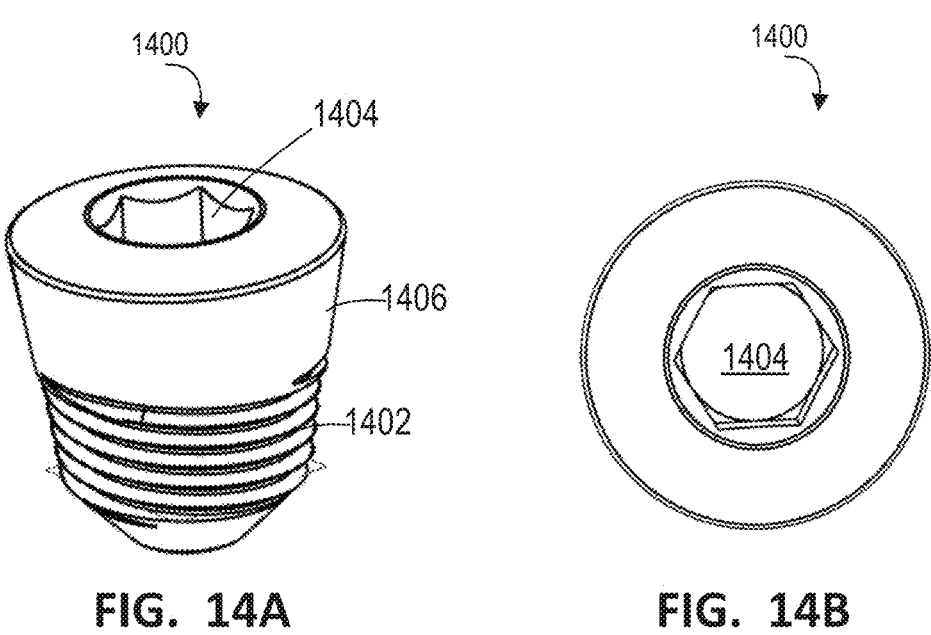

FIGS. 14A, 14B, and 14C are perspective view, top view, and bottom view respectively of a fastener 1400, according to one embodiment. In one embodiment, the fastener 1400 is a set screw that includes external threads 1402 and a drive feature 1404 or drive recess.

In one embodiment, the external threads 1402 serve to engage internal threads of a fastener opening 132, 414, 514, 618 and/or a connector opening 652 formed in one of a proximal plate part 620, distal plate part 622 or a proximal extender part 624 or distal extender part 626. In certain embodiments, a proximal extender part 624 may fit over a proximal plate part 620 and a distal extender part 626 may fit over a distal plate part 622 and the proximal plate part 620 and distal plate part 622 may each include one or more connector openings 652. In such a configuration, the external threads 1402 of the fastener 1400 may engage internal threads of the connector opening 652 and draw the fastener 1400 toward the proximal plate part 620 or distal plate part 622. A side wall 1406 of the fastener 1400 may taper from narrower to wider such that as the fastener 1400 enters the connector opening 652 the side wall engages a proximal extender part 624 or distal extender part 626.

The drive feature 1404, drive recess, or other torque-receiving is configured to receive a drive member of a fastening tool (not shown) used to install the fastener 1400. The drive feature 1404 can be configured to have any one of a variety of shapes including slotted, Torx, Torx plus, Philips, Quadrex, Pozidriv, square recess, tri-wing, spanner, or the like. The drive feature 1404 can be centered on a longitudinal axis of the fastener 1400 which aligns with a longitudinal axis of a fastener opening 618 when the fastener 1400 is inserted into the opening. Of course, those of skill in the art recognize that the shape and configuration of the drive member and the drive feature 1404 can be reversed and thus comprise an embodiment within the scope of the present disclosure.

Figure 14C:
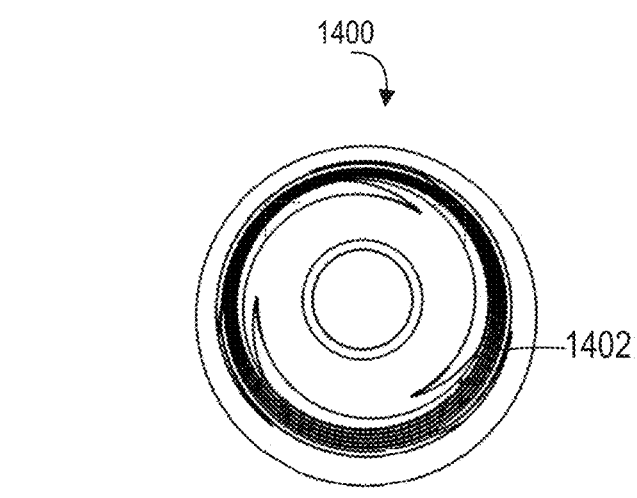
Figure 15:
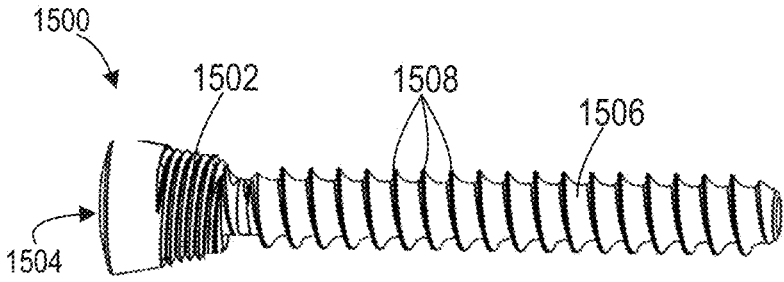
FIG. 15 is a perspective view of a fastener, according to one embodiment.

FIG. 15 is a perspective view of a fastener 1500, according to one embodiment. The fastener 1500 may include similar parts to the fastener 1400 illustrated in FIG. 14. Thus, the fastener 1500 may include external threads 1502 and a drive feature 1504 (not shown) which may be structured and may function similarly to the external threads 1402 and drive feature 1404. The fastener 1500 may also include a shaft 1506 with bone threads 1508. The fastener 1500 can be used in a fastener opening 132, 414, 514, 618 and/or a connector opening 652. The bone threads 1508 may be configures and spaced relative to each other and have a pitch that facilitates purchase into the bone as the fastener 1500 is inserted.

Figure 16A:
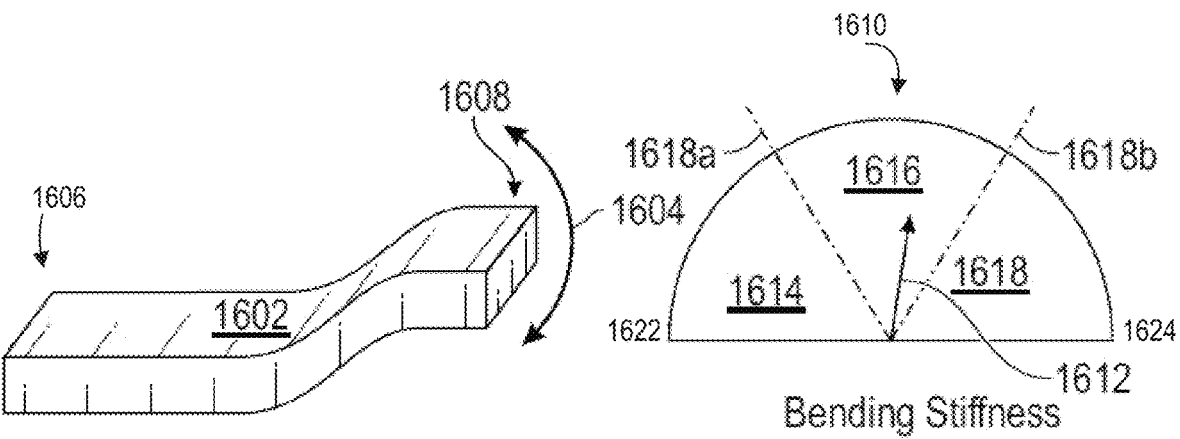
FIG. 16A illustrates a solid body in relation to bending stiffness, according to one embodiment.

FIG. 16A illustrates a solid body in relation to bending stiffness, according to one embodiment. FIG. 16A illustrates the concept of bending stiffness by way of a solid body 1602 that experiences a bending force 1604 (represented by double head arrow 1604). The solid body 1602 may include a proximal end 1606 and a distal end 1608. The solid body 1602 has some degree of elasticity.

The bending force 1604 may be applied to the solid body 1602 at any point. A solid body 1602 may be most susceptible to a bending force 1604 at its ends (e.g., proximal end 1606 or distal end 1608), particularly where one end is fixed while the other end experiences the bending force 1604. Generally, bending stiffness may be measured in newtons per meter or pounds per inch.

FIG. 16A illustrates the solid body 1602 having its proximal end 1606 fixed and its distal end 1608 free and exposed to the bending force 1604. FIG. 16A illustrates a dial 1610 that can be used to indicate a level, degree, or measure of bending stiffness. As used herein, a dial refers to a face upon which some measurement is registered usually by means of graduations and a pointer, such as a needle. ("dial." Merriam-Webster.com. Merriam-Webster, 2021. Web. 6 Jan. 2021. Modified.) The dial 1610 may include a pointer or needle 1612 that indicates a measure or amount of stiffness for an object. The dial 1610 may be divided into one or more sections, for example, three sections 1614, 1616, 1618 each divided by one or more thresholds 1620*a,b*. Section 1614 may represent levels of stiffness that are insufficient for a particular use case or purpose and may be bounded by a zero or initial starting point 1622 and first threshold 1618*a*. Section 1616 may represent levels of stiffness that are sufficient and/or satisfactory for a particular use case or purpose and may be bounded by first threshold 1618*a* and second threshold 1618*b*. Section 1618 may represent levels of stiffness that are more than sufficient and/or more than satisfactory for a particular use case or purpose and may be bounded by second threshold 1618*b* and maximum level 1624. Alternatively, or in addition, section 1618 may represent levels of stiffness that are also insufficient and/or not satisfactory for a particular use case or purpose. For example, where too much stiffness exists this may result in other problems that are to be avoided. In the example, of FIG. 16A, the solid body 1602 has a bending stiffness that falls into section 1616 which is sufficient for the intended use of the solid body 1602 and indicated by needle 1612.

The amount of bending force 1604 the solid body 1602 can experience depends on a number of factors and/or properties of the solid body 1602 and its environment. As used herein, "property" refers to any attribute, characteristic, trait, element, aspect, quality, data value, setting, or feature of an object or thing. As used herein, bending stiffness refers to an extensive property of an object, system, assembly, or apparatus, such as solid body 1602. Similarly, torsional stiffness is an extensive property and depends on a number of factors and/or properties of the solid body 1602 and its environment.

"Extensive property" refers to a physical property of a material, structure, object, and/or system. physical properties of materials and systems can be categorized as being either intensive or extensive, according to how the property changes when the size (or extent) of the system changes. According to International Union of Pure and Applied Chemistry (IUPAC), an intensive quantity is one whose magnitude is independent of the size of the system, whereas an extensive quantity is one whose magnitude is additive for subsystems.

An intensive property does not depend on the system size or the amount of material in the system. An intensive property is not necessarily homogeneously distributed in space; an intensive property can vary from place to place in a body of matter and radiation. Examples of intensive properties include temperature, T; refractive index, n; density, $\rho$; and hardness of an object, $\eta$.

By contrast, extensive properties such as the mass, volume and entropy of systems are additive for subsystems. An intensive property is a physical quantity whose value does not depend on the amount of substance which was measured. An extensive property is a physical quantity whose value is proportional to the size of the system it describes, to the quantity of matter in the system, and/or that is dependent on the material and its shape and boundary conditions. For example, the mass of a sample is an extensive quantity; it depends on the amount of substance. The related intensive quantity is the density which is independent of the amount.

(Search "intensive and extensive properties" and "stiffness" on Wikipedia.com Jul. 24, 2022. CC-BY-SA 3.0 Accessed Jul. 26, 2022. Modified.)

Figure 16B:
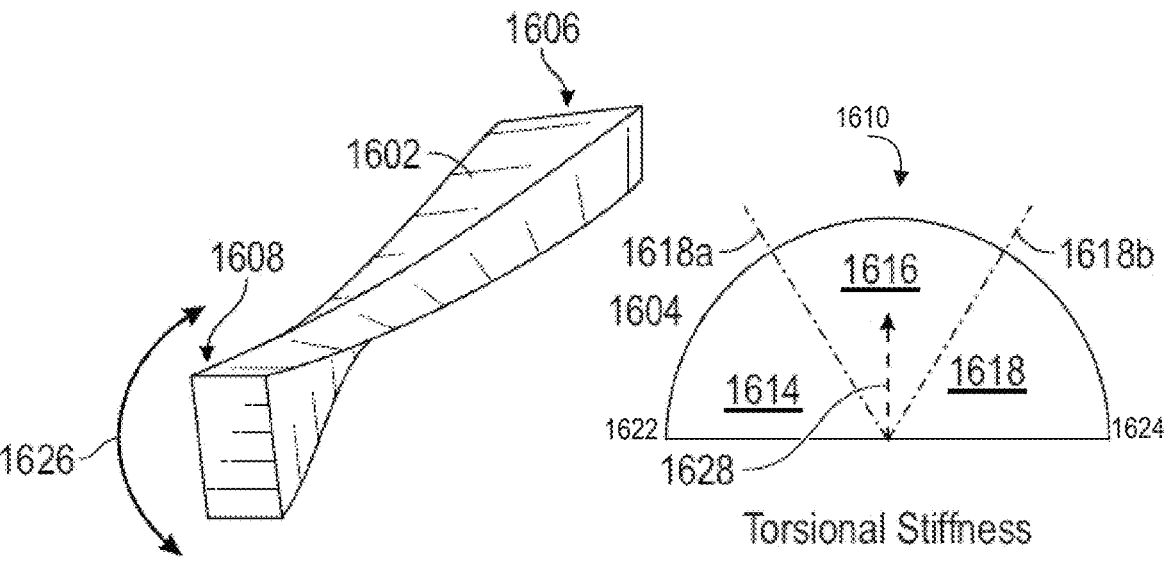
FIG. 16B illustrates a solid body in relation to torsional stiffness, according to one embodiment.

FIG. 16B illustrates a solid body 1602 in relation to torsional stiffness, according to one embodiment. FIG. 16B includes the solid body 1602 and dial 1610 in relation to torsional stiffness. The solid body 1602 may experience a torque or twisting force 1626 (represented by double head arrow 1626). The dial 1610 includes the section 1614, section 1616, section 1618, and first threshold 1618a and second threshold 1618b. The needle 1628 represents a measure of the twisting force 1626 that the solid body 1602 can experience before failing and that is sufficient for the intended use of the solid body 1602. In the example, of FIG. 16B, the solid body 1602 has a torsional stiffness that falls into section 1616 which is sufficient for the intended use of the solid body 1602 and indicated by needle 1628.

Conventional treatments combining an intramedullary nail and a bone plate for a procedure do not provide a satisfactory result in healing of the long bone. In particular, doing so may contribute to stress-shielding and/or to non-unions. Those of skill in the art will appreciate that the interface between an intramedullary nail and the intramedullary canal, an interface between bone fasteners that engage with the intramedullary nail and the intramedullary nail, and/or an interface between the a head of the bone fasteners and a cortex of the long bone can provide unstable torsional stiffness and stable bending stiffness. Similarly, a bone plate of 4 mm thickness or less can have an interface between the bone plate and fasteners that engage the bone plate and the bone that provide unstable bending stiffness and stable torsional stiffness. The present disclosure provides a fixation system, assembly, apparatus and/or construct that provides both a stable torsional stiffness and stable bending stiffness using an intramedullary nail and a bone plate together where the bone plate is less than 4 mm thick.

"Nonunion" refers to a condition of a bone fracture in which the has not healed or shown radiographical signs of healing progression since a minimum of nine months have elapsed since the injury, i.e., no change in the fracture callus, for the final three months (i.e., six months to be considered a nonunion plus three additional months to verify that the nonunion is established). (Food and Drug Administration. "Guidance Document for Industry and CDRH Staff for the Preparation of Investigational Device Exemptions and Pre-market Approval Applications for Bone Growth Stimulator Devices." United Stated: Office of the Federal Register, National Archives and Records Administration (1998). Modified.) "Stress shielding" refers to the reduction in bone density (osteopenia) as a result of removal of typical stress from the bone by an implant (for instance, the femoral component of a hip prosthesis). (Search "stress shielding" on Wikipedia.com Mar. 6, 2022. CC-BY-SA 3.0 Accessed Jul. 26, 2022.)

The present disclosure provides a system, method, and apparatus for using an intramedullary nail and bone plate to treat a long bone fracture. The present disclosure combines an intramedullary nail having sufficient bending stiffness and insufficient torsional stiffness with a bone plate having sufficient torsional stiffness and insufficient bending stiffness.

The solid body 1602 of FIGS. 16A and 16B are representative of any construct, system, apparatus, assembly, component, or the like. For example, the solid body 1602 can be representative of an intramedullary nail secured within an intramedullary canal of a long bone and/or the solid body 1602 can be representative of a bone plate secured to an exterior of a long bone. The intramedullary nail and the bone plate may or may not be fixated to each other.

Figures 17A, 17B, 17C:
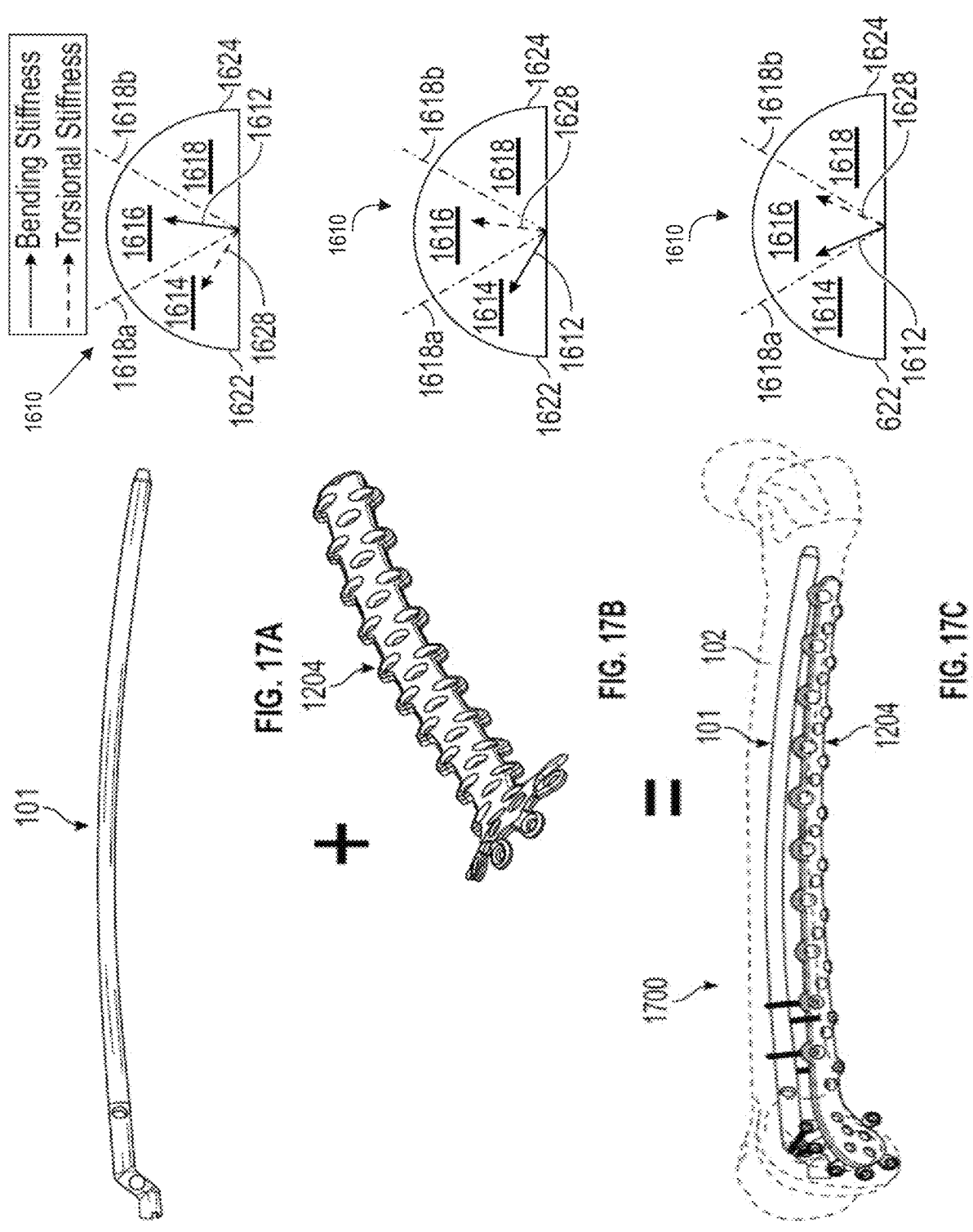
FIG. 17A illustrates an intramedullary nail, according to one embodiment.
FIG. 17B illustrates a bone plate, according to one embodiment.
FIG. 17C illustrates the intramedullary nail of FIG. 17A and the bone plate of FIG. 17B deployed together with fasteners, according to one embodiment.

FIG. 17A illustrates an intramedullary nail, according to one embodiment. In one embodiment, the intramedullary nail is a nail such as intramedullary nail 101 described above that includes an offset section 116. The intramedullary nail 101 is configured to engage with a femur 102 that includes a bone fracture. The intramedullary nail 101 includes a first bending stiffness indicated by needle 1612 on dial 1610. The dial 1610 also includes needle 1628 indicating a first torsional stiffness of intramedullary nail 101. Needle 1612 indicates that the first bending stiffness is sufficient (between threshold 1618a and threshold 1618b) for a planned long bone fixation procedure. Needle 1628 indicates that the first torsional stiffness is insufficient (between starting point 1622 and threshold 1618a) to stabilize the bone fracture independent of a bone plate. Consequently, if the intramedullary nail 101 is used alone for the planned long bone fixation procedure the femur 102 will experience sufficient bending stiffness to support the desired healing, but not sufficient torsional stiffness.

FIG. 17B illustrates a bone plate, according to one embodiment. In one embodiment, the bone plate is a bone plate such as bone plate 1204 (e.g., a lateral bone plate, of course a medial bone plate such as medial bone plate 500b can be used). The bone plate 1204 is configured to engage with a lateral side of a femur 102 that includes a bone fracture. The bone plate 1204 includes a second bending stiffness indicated by needle 1612 on dial 1610. The dial 1610 also includes needle 1628 indicating a second torsional stiffness of bone plate 1204. Needle 1612 indicates that the second bending stiffness is insufficient (between starting point 1622 and threshold 1618a) to stabilize the bone fracture independent of an intramedullary nail. Needle 1628 indicates that the second torsional stiffness is sufficient (between threshold 1618a and threshold 1618b) for a planned long bone fixation procedure. Consequently, if the bone plate 1204 is used alone for the planned long bone fixation procedure the femur 102 will experience insufficient bending stiffness to support the desired healing, but sufficient torsional stiffness.

The present disclosure describes a solution. Rather than use intramedullary nail 101 or bone plate 1204 alone, deploy both together (indicated by the plus sign between FIGS. 17A and 17B, which results in FIG. 17C). FIG. 17C illustrates the intramedullary nail of FIG. 17A and the bone plate of FIG. 17B deployed together with fasteners, according to one embodiment. FIGS. 17A and 17B and 17C include the aspects of torsional stiffness and bending stiffness as these exist in a fixation construct, apparatus, or system that includes deployment of these implants in a long bone such as a femur 102 as illustrated in FIG. 17C. A bone fracture is between a distal end 104 and a proximal end 106 of the intramedullary nail 101.

The dial 1610 in FIG. 17C illustrates the bending stiffness 1612 and torsional stiffness 1628 for a femur fixation system 1700, rather than for an intramedullary nail 101 or bone plate 1204 individually. The needle 1612 indicates that the bending stiffness for the femur fixation system 1700 is sufficient (between threshold 1618a and threshold 1618b) to stabilize the bone fracture. Needle 1628 indicates that the torsional stiffness for the femur fixation system 1700 is sufficient (between threshold 1618a and threshold 1618b) to stabilize the bone fracture. In this manner a stiffness extensive property of the intramedullary nail 101 and a stiffness extensive property of the bone plate 1204 combined to provide sufficient bending stiffness and sufficient torsional stiffness for the femur fixation system 1700.

By deploying the intramedullary nail 101 inside the femur 102 and the bone plate 1204 outside the femur 102 along a cortex, such as the lateral cortex, stiffness features of the intramedullary nail 101 and the bone plate 1204 can be used to complement and support each other for an optimal femur fixation system 1700. Advantageously, combining the intramedullary nail 101 and the bone plate 1204 enables the sufficient torsional stiffness of the bone plate 1204 to compensate for the insufficient torsional stiffness of the intramedullary nail 101 and the sufficient bending stiffness of the intramedullary nail 101 to compensate for the insufficient bending stiffness of the bone plate 1204.

In certain embodiments, the sufficient torsional stiffness of the bone plate 1204 may augment the torsional stiffness of the intramedullary nail 101 and the sufficient bending stiffness of the intramedullary nail 101 may augment the bending stiffness of the bone plate 1204.

With the intramedullary nail 101 and bone plate 1204 positioned as shown in FIG. 17B, fasteners may be deployed through the bone plate 1204. In certain embodiments, one or more fasteners may engage with both the bone plate 1204 and the intramedullary nail 101 and/or one or more of the fasteners may engage with the bone plate 1204 and the bone, but not engage with the intramedullary nail 101. In one embodiment, at least one fastener engages with the bone plate 1204 and extends into the femur and also engage with the intramedullary nail 101 such that the bone plate 1204 and intramedullary nail 101 together provide sufficient torsional stiffness and bending stiffness to stabilize the bone fracture.

In the illustrated embodiment of FIGS. 17B and 17C, the bone plate 1204 includes a stiffness extensive property. The stiffness extensive property can be identified using one or more of a torsional extensive property and a bending extensive property. In one embodiment, a torsional extensive property is an extensive property relating to torsion. In one embodiment, the torsional extensive property relates to torsional stiffness. In one embodiment, a bending extensive property is an extensive property relating to bending. In one embodiment, the bending extensive property relates to torsional stiffness.

In the illustrated embodiment, the torsional extensive property for the bone plate 1204 is different from the bending extensive property. Advantageously, the bone plate 1204 is configured to select a desired level for the torsional extensive property and the bending extensive property in relation to the intramedullary nail 101 such that a desired stiffness for the femur fixation system 1700 is accomplished. In one embodiment, the femur fixation system 1700 includes a stiffness extensive property that includes a torsional extensive property and a bending extensive property of a bone plate (e.g., bone plate 1204) and a torsional extensive property and a bending extensive property of an intramedullary nail (e.g., intramedullary nail 101).

One benefit of using the femur fixation system 1700 is that the bone plate can be thinner that conventional lateral or medial bone plates for a femur. For example, the bone plate can have a thickness of less than four millimeters. Bone plates having a thickness of less than four millimeters has insufficient bending stiffness, however this insufficiency is compensated for by the bending stiffness of the intramedullary nail. Similarly, the thinner bone plate has a torsional stiffness that compensates for insufficient torsional thickness of the intramedullary nail. Since the bone plate, particularly a lateral bone plate is close to the surface of the skin and there is little fat, padding, or other soft tissue between the skin surface and the bone plate, using a thinner bone plate can provide a more comfortable fixation solution for a patient.

Those of skill in the art will appreciate that a variety of physical characteristics, properties, and aspects of a bone plate can be adjusted, designed, or engineered to get a desired level of torsional stiffness and/or bending stiffness. For example, changes in the shape and/or configuration of the bone plate can be made to provide a bone plate having a different or desirable torsional stiffness and/or bending stiffness. Alternatively, or in addition, the composition of the bone plate can be changed and/or engineered to provide a bone plate having a different or desirable torsional stiffness and/or bending stiffness. Alternatively, or in addition, a cross-sectional configuration of the bone plate can be changed and/or engineered to provide a bone plate having a different or desirable torsional stiffness and/or bending stiffness. Of course, the shape, composition, and/or cross-sectional configuration can each be changes to produce a bone plate having a torsional stiffness that is different (greater than or less than) a bending stiffness.

"Composition" refers to a compound artificial substance or material. Generally, a composition is a man-made material that is a composite of more than one material and/or element. Typically, a composition is a single structure or object that includes the several parts and/or elements. (Search "composition" on wordhippo.com. WordHippo, 2022. Web. Modified Accessed 4 Aug. 2022.) "Composite" refers to an object or structure made up of several parts and/or elements. Typically, a composite is a single structure or object that includes the several parts and/or elements. (Search "composite" on wordhippo.com. WordHippo, 2022. Web. Modified Accessed 4 Aug. 2022.)

Figures 18, 19A, 19B, 19C, 20:
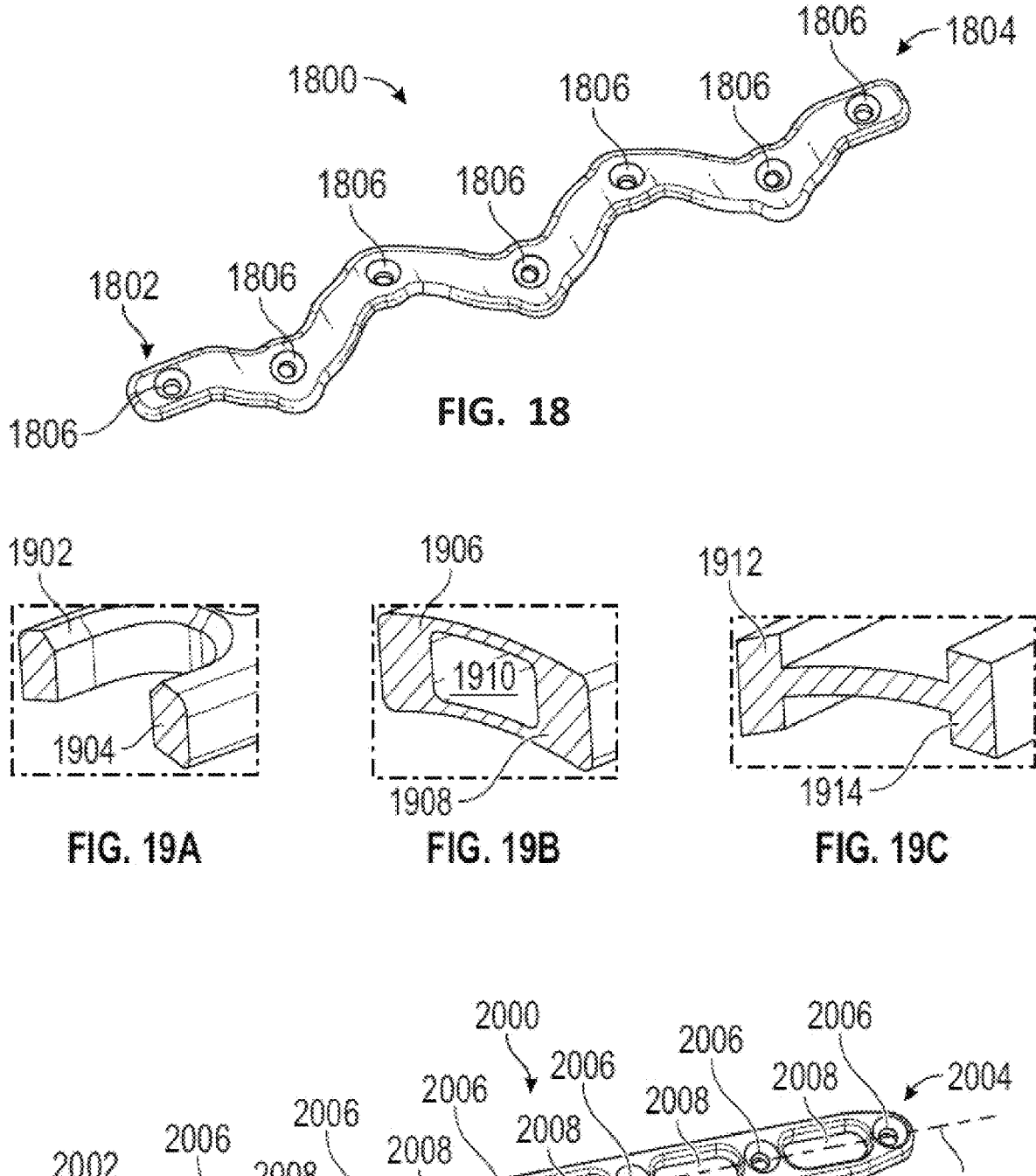
FIG. 18 illustrates a bone plate having greater torsional stiffness than bending stiffness, according to one embodiment.
FIGS. 19A-19C illustrate cross-sectional configurations for a bone plate, according to one embodiment.
FIG. 20 illustrates an example bone plate having greater torsional stiffness than bending stiffness, according to one embodiment.

FIG. 18 illustrates a bone plate 1800 that has greater torsional stiffness than bending stiffness, according to one embodiment. The bone plate 1800 includes a proximal end 1802, a distal end 1804, and a plurality of fastener openings 1806. The bone plate 1800 is an elongate structure that has a shape configured such that a torsional stiffness for the bone plate 1800 is greater than a bending stiffness of the bone plate 1800. In the illustrated embodiment, the bone plate 1800 has a W-shape or Wave shape as a body of the bone plate 1800 extends between the proximal end 1802 and the distal end 1804. Those of skill in the art will appreciate that the "W" shape of the bone plate 1800 provides greater torsional stiffness than if the bone plate 1800 were rectangular shaped.

"Wave shape" or "W" shape refers to any mechanical device, apparatus, body, base, protrusion, member, component, system, assembly, or structure having a shape that resembles or mimics or conforms to or matches one or more attributes of a letter "W" and/or of waves of a body of liquid such as, by example, waves of a sea, lake, ocean, or the like. The wave shape may include angles, bends, and or curves and may be partial or complete. In other words, one or more parts of a structure may resemble, be shaped like, or conform to one or more parts of a "W" letter and/or a wave. The "Wave shape" or "W" shape may be observed from any side or perspective of the object or structure, including, but not limited to any cross-section of the object or structure.

FIGS. 19A-19C illustrate cross-sectional configurations for a bone plate, according to one embodiment. Changing the cross-sectional configuration of an object can change the torsional stiffness of the object. "Cross-sectional configuration" refers to a configuration a cross-section of a device, apparatus, structure, or object. A cross-sectional configuration may include openings, passages, voids, struts, braces, ridges, rails, and/or edges organized to implement a particular cross-sectional configuration. As used herein, a "rail" refers to a structure that is longer than the structure is wide. In certain embodiments, a rail may have a cross-section that resembles, is similar to, and/or matches a capital letter "I" in a serif typeface. A rail may be made from a variety of materials including, but not limited to, metal, plastic, ceramic, wood, fiberglass, acrylic, carbon, biocompatible materials, biodegradable materials or the like. Often a rail is made from plastic due to its lower expense, strength and durability. A rail may also be formed of any biocompatible materials, including but not limited to biocompatible metals such as Titanium, Titanium alloys, stainless steel alloys, cobalt-chromium steel alloys, nickel-titanium alloys, shape memory alloys such as Nitinol, biocompatible ceramics, and biocompatible polymers such as Polyether ether ketone (PEEK) or a polylactide polymer (e.g. PLLA) and/or others. A rail may be coupled to another component or integrated with and/or form part of another component or structure. In certain embodiments, a rail may be configured or arranged to support another structure that may translate along, slide along, or otherwise move in relation to the rail. In certain embodiments, one rail may have a corresponding opposite rail such that the two rails for a pair of rails. The pair of rails may cooperate to support another component or structure as that structures moves in relation to the pair of rails. As used herein, "edge" refers to a structure, boundary, or line where an object, surface, or area begins or ends. An edge can also refer to a boundary or perimeter between two structures, objects, or surfaces. An edge can also refer to a narrow part adjacent to a border. (search "edge" on Merriam-Webster. com. Merriam-Webster, 2021. Web. 3 Aug. 2021. Modified.) In certain embodiments, an edge can be a one dimensional or a two dimensional structure that joins two adjacent structures or surfaces. Furthermore, an edge may be at a perimeter of an object or within a perimeter or boundary of an object.

FIG. 19A shows a transverse cross section for a body 406 of a bone plate 400 that includes opposing rails 1902, 1904 on each long edge of the bone plate 400. The cross sectional configuration illustrated in FIG. 19A may be referred to as a rail cross-section.

FIG. 19B shows a transverse cross section for a body 406 of a bone plate 400 that includes opposing solid sections 1906, 1908 on each long edge with a passage 1910 between the opposing solid sections 1906, 1908. The passage 1910 may extend from a proximal end of the bone plate 400 to a distal end or may partially extend between a proximal end and a distal end. The cross sectional configuration illustrated in FIG. 19B may be referred to as a shell cross-section.

FIG. 19C shows a transverse cross section for a body 406 of a bone plate 400 shaped like an I-beam. A top 1912 and bottom 1914 of the I may extend along each long edge of the bone plate 400. The cross sectional configuration illustrated in FIG. 19C may be referred to as an I-beam cross-section.

In certain embodiments, the cross sectional configurations illustrated in FIGS. 19A-19C may cause the bone plate 400 to have a torsional stiffness greater than a bending stiffness for the bone plate 400.

FIG. 20 illustrates an example bone plate having greater torsional stiffness than bending stiffness, according to one embodiment. The bone plate 2000 includes a proximal end 2002, a distal end 2004, and a plurality of fastener openings 2006. The bone plate 2000 is an elongate structure that has a shape configured such that a torsional stiffness for the bone plate 2000 is greater than a bending stiffness of the bone plate 2000. The bone plate 2000 may include one or more torsional stiffness features 2008 disposed along a longitudinal axis 2010. A torsional stiffness feature 2008 is a structure that increases torsional stiffness of a structure that includes the torsional stiffness feature 2008.

In the illustrated embodiment, the torsional stiffness feature 2008 is an opening that extends from a superior surface 2012 to an inferior surface 2014 of the bone plate 2000. In one embodiment, the torsional stiffness feature 2008 may have an oval, ellipse, or slot shape. It should be noted that the torsional stiffness feature 2008 can form a rail cross-sectional configuration for parts of the bone plate 2000.

Figure 21:
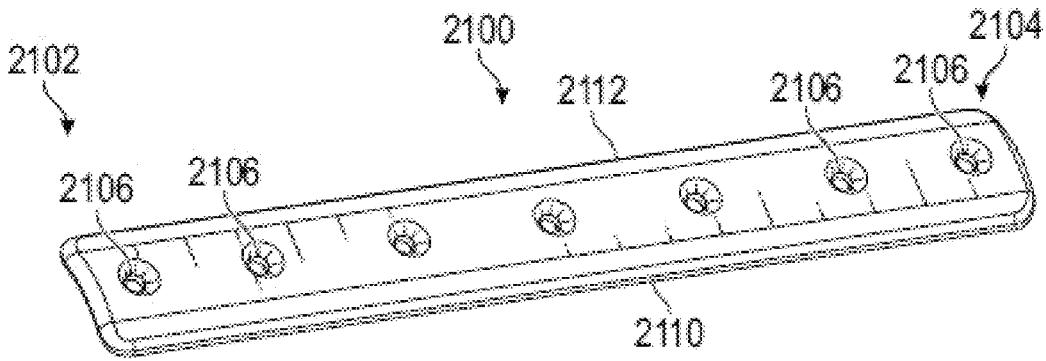
FIG. 21 illustrates an example bone plate, according to one embodiment.

FIG. 21 illustrates an example bone plate 2100, according to one embodiment. The bone plate 2100 includes a proximal end 2102, a distal end 2104, and a plurality of fastener openings 2106. The bone plate 2100 is an elongate structure. In the illustrated embodiment, the bone plate 2100 is a composite of two or more materials selected, design, engineered and positioned in the bone plate 2100 such that the bone plate 2100 has greater torsional stiffness than bending stiffness.

In one embodiment, the bone plate 2100 includes a lateral edge 2110 and a medial edge 2112. The lateral edge 2110 may extend between the proximal end 2102 and the distal end 2104. The medial edge 2112 may extend between the proximal end 2102 and the distal end 2104.

In the illustrated embodiment, the material of the bone plate 2100 at the lateral edge 2110 and the medial edge 2112 may be made from a first material and the bone plate 2100 between the lateral edge 2110 and the medial edge 2112 may be made from a second material. The first material of the lateral edge 2110 and the medial edge 2112 may have a greater torsional stiffness than the second material between the lateral edge 2110 and the medial edge 2112. In one embodiment, the first material is less elastic than the second material. The bone plate 2100 is a composite of two different materials. Of course, the bone plate 2100 can also be a composite of two or more materials that are biocompatible with a patient.

Alternatively, or in addition, the lateral edge 2110 may be made from a first material, a body of the bone plate 2100 between the lateral edge 2110 and the medial edge 2112 may be made from a second material and the medial edge 2112 may be made from a third material.

Figure 22:
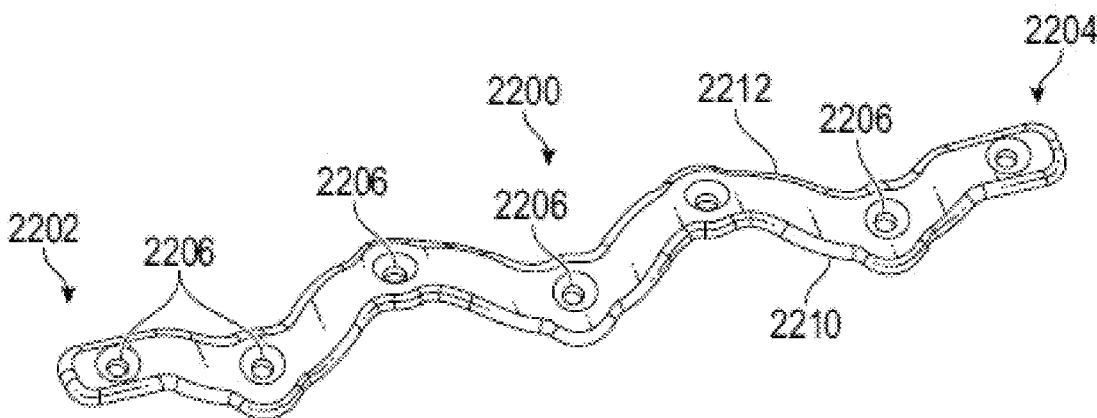
FIG. 22 illustrates an example bone plate, according to one embodiment.

FIG. 22 illustrates an example bone plate 2200, according to one embodiment. The bone plate 2200 includes a proximal end 2202, a distal end 2204, and a plurality of fastener openings 2206. The bone plate 2200 is an elongate structure. The bone plate 2200 includes a lateral edge 2210 and a medial edge 2212. The lateral edge 2210 may extend between the proximal end 2202 and the distal end 2204. The medial edge 2212 may extend between the proximal end 2202 and the distal end 2204.

Those of skill in the art will appreciate that the aspects used in embodiments of FIGS. 18-21 can be combined to form a bone plate 2200 that has a greater torsional stiffness than bending stiffness. The bone plate 2200 is one example. The bone plate 2200 may be a composite of two or more materials with a first material used in the lateral edge 2210 and medial edge 2212 and a second material used for a body of the bone plate 2200 between the lateral edge 2210 and medial edge 2212. In addition, the bone plate 2200 may be shaped in a shape (e.g., "W" shape) that increases torsional stiffness. Of course, the bone plate 2200 may be made with a cross-sectional configuration that increases torsional stiffness.

It should be noted that the same configurations, design, and/or engineering aspects applied to a bone plate in the examples of FIGS. 18-22 can also be applied to an intramedullary nail to provide an intramedullary nail having a greater bending stiffness than torsional stiffness.

Figure 23:
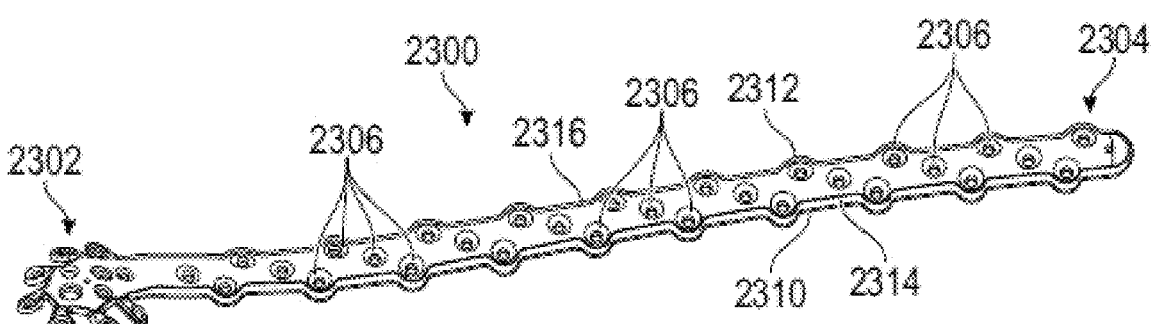
FIG. 23 illustrates an example bone plate, according to one embodiment.

FIG. 23 illustrates an example bone plate 2300, according to one embodiment. The bone plate 2300 includes a proximal end 2302, a distal end 2304, and a plurality of fastener openings 2306. The bone plate 2300 is an elongate structure. The bone plate 2300 includes a lateral edge 2310 and a medial edge 2312. The lateral edge 2310 may extend between the proximal end 2302 and the distal end 2304. The medial edge 2312 may extend between the proximal end 2302 and the distal end 2304.

In the illustrated embodiment, the torsional stiffness of the bone plate 2300 may be increased by including a first rail 2314 and a second rail 2316. The first rail 2314 may be positioned near or along the lateral edge 2310 and may extend from a superior surface 2318 of the bone plate 2300. The second rail 2316 may be positioned near or along the medial edge 2312 and may also extend from the superior surface 2318 of the bone plate 2300.

Figures 24A, 24B:
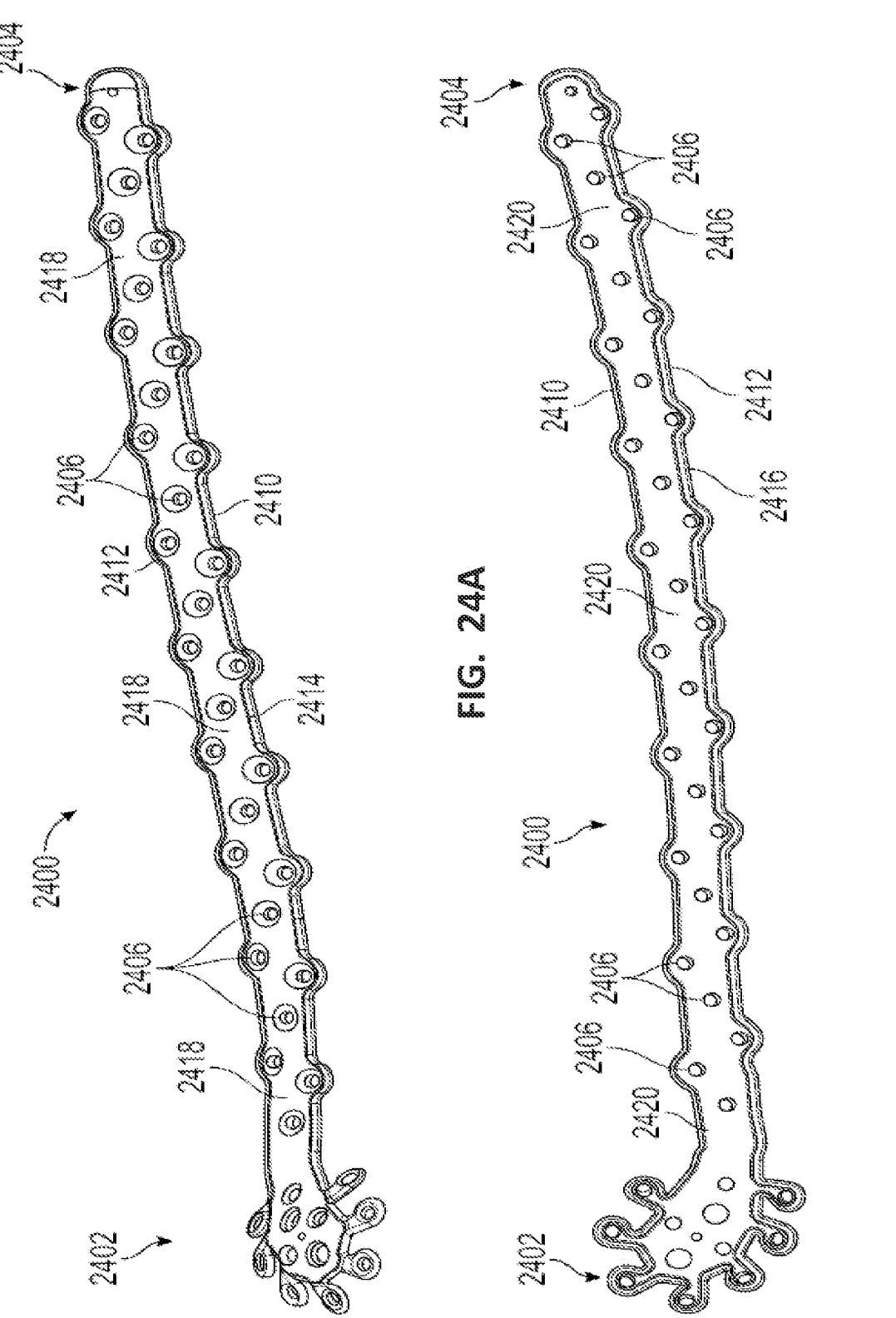
FIGS. 24A, 24B illustrate a top and a bottom perspective view of an example bone plate, according to one embodiment.

FIGS. 24A, 24B illustrate a top and a bottom perspective view of an example bone plate 2400, according to one embodiment. The bone plate 2400 includes a proximal end 2402, a distal end 2404, and a plurality of fastener openings 2406. The bone plate 2400 is an elongate structure. The bone plate 2400 includes a lateral edge 2410 and a medial edge 2412. The lateral edge 2410 may extend between the proximal end 2402 and the distal end 2404. The medial edge 2412 may extend between the proximal end 2402 and the distal end 2404.

In the illustrated embodiment, the torsional stiffness of the bone plate 2400 may be increased by including a first rail 2414 and a second rail 2416. The first rail 2414 may be positioned near or along the lateral edge 2410 and may extend from a superior surface 2418 of the bone plate 2400. The second rail 2416 may be positioned near or along the medial edge 2412 and may extend from the inferior surface 2420 of the bone plate 2400. In certain embodiments, the bone plate 2400 may include a first rail 2414 and/or a second rail 2416 that extend partially between the proximal end 2402 and the distal end 2404. In certain embodiments, the bone plate 2400 may include a single rail (e.g., first rail 2414 or second rail 2416) extending from one surface (e.g., superior surface 2418 or inferior surface 2420). Furthermore, those of skill in the art understand that one or more rails may extend at least part way between the proximal end 2402 and the distal end 2404 and may be positioned on a surface of the bone plate 2400 at a position other than at one or the other of the lateral edge 2410 and the medial edge 2412.

Figure 25:
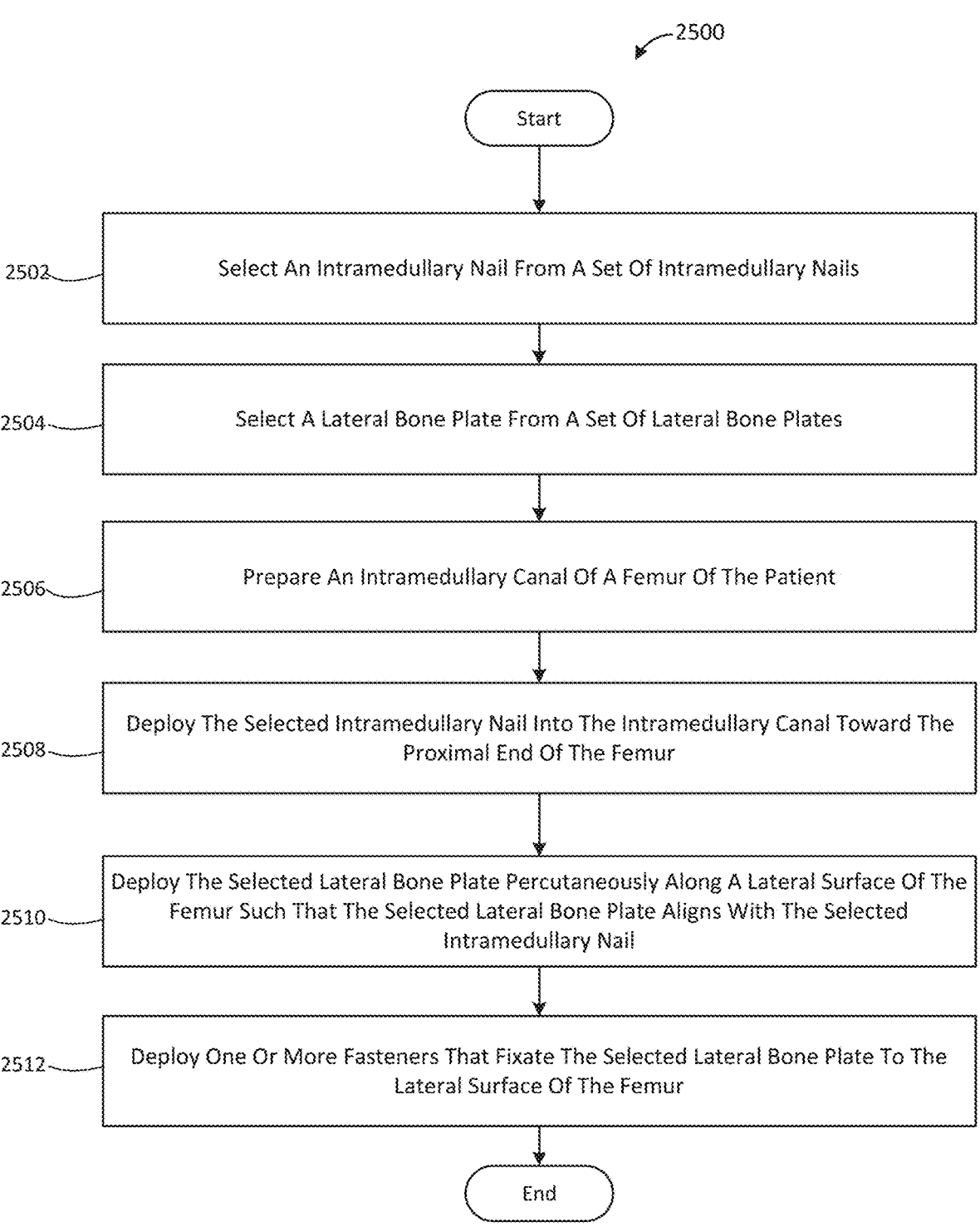
FIG. 25 illustrates one example of a method for stabilizing a bone fracture in a femur of a patient according to one embodiment.

FIG. 25 illustrates one example of a method 2500 for stabilizing a bone fracture in a femur of a patient according to one embodiment. In certain embodiments, the method 2500 begins and a user selects 2502 an intramedullary nail from a set of intramedullary nails. Each intramedullary nail in the set includes a different bending stiffness and an insufficient torsional stiffness to stabilize the bone fracture independent of a bone plate. Next, a user selects 2504 a lateral bone plate from a set of lateral bone plates. Each lateral bone plate in the set includes a different torsional stiffness and an insufficient bending stiffness to stabilize the bone fracture independent of the intramedullary nail. The different torsional stiffness of the selected lateral bone plate together with the bending stiffness of the selected intramedullary nail when secured to the femur provide sufficient torsional stiffness and bending stiffness to stabilize the bone fracture and promote healing of the bone fracture.

Next, a user, such as a surgeon, prepares 2506 an intramedullary canal of a femur of the patient. In one embodiment, the intramedullary canal may extend from a distal end of the femur to a proximal end of the femur.

Next, a user, such as a surgeon, may deploy 2508 the selected intramedullary nail into the intramedullary canal toward the proximal end of the femur. The user also deploys 2510 the selected lateral bone plate percutaneously along a lateral surface of the femur such that the selected lateral bone plate aligns with the selected intramedullary nail. The user then deploys 2512 one or more fasteners that fixate the selected lateral bone plate to the lateral surface of the femur and the method 2500 ends.

In certain embodiments, after step 2510 and/or step 2512, a user may deploy one or more fasteners that fixation the selected intramedullary nail to the femur 102.

The present disclosure discloses surgical devices, systems, and/or methods for fixation in relation to fractures of a long bone of a patient. Existing fixators and/or fixation devices, methods, or steps for long bone fractures are limited.

Conventional techniques for addressing a fracture of a long bone, particularly for a femur 102, is to deploy an intramedullary nail and a bone plate (medial bone plate, lateral bone plate, or both). However, if the procedure is done with a minimal number of incisions and these incisions are as small as possible, the procedure can include advancing the intramedullary nail within an intramedullary canal and percutaneously advancing a bone plate along a medial side or a lateral side of a long bone such as a femur 102. Unfortunately, once the intramedullary nail and bone plate have been inserted a surgeon can find it a challenge to deploy a fastener meant to engage with both the bone plate and the intramedullary nail. Also, a surgeon can find it a challenge to deploy a fastener meant to engage or contact with the bone plate and bone but not the intramedullary nail. The present disclosure provides a system, method, and apparatus to remediate these challenges.

Figure 26:
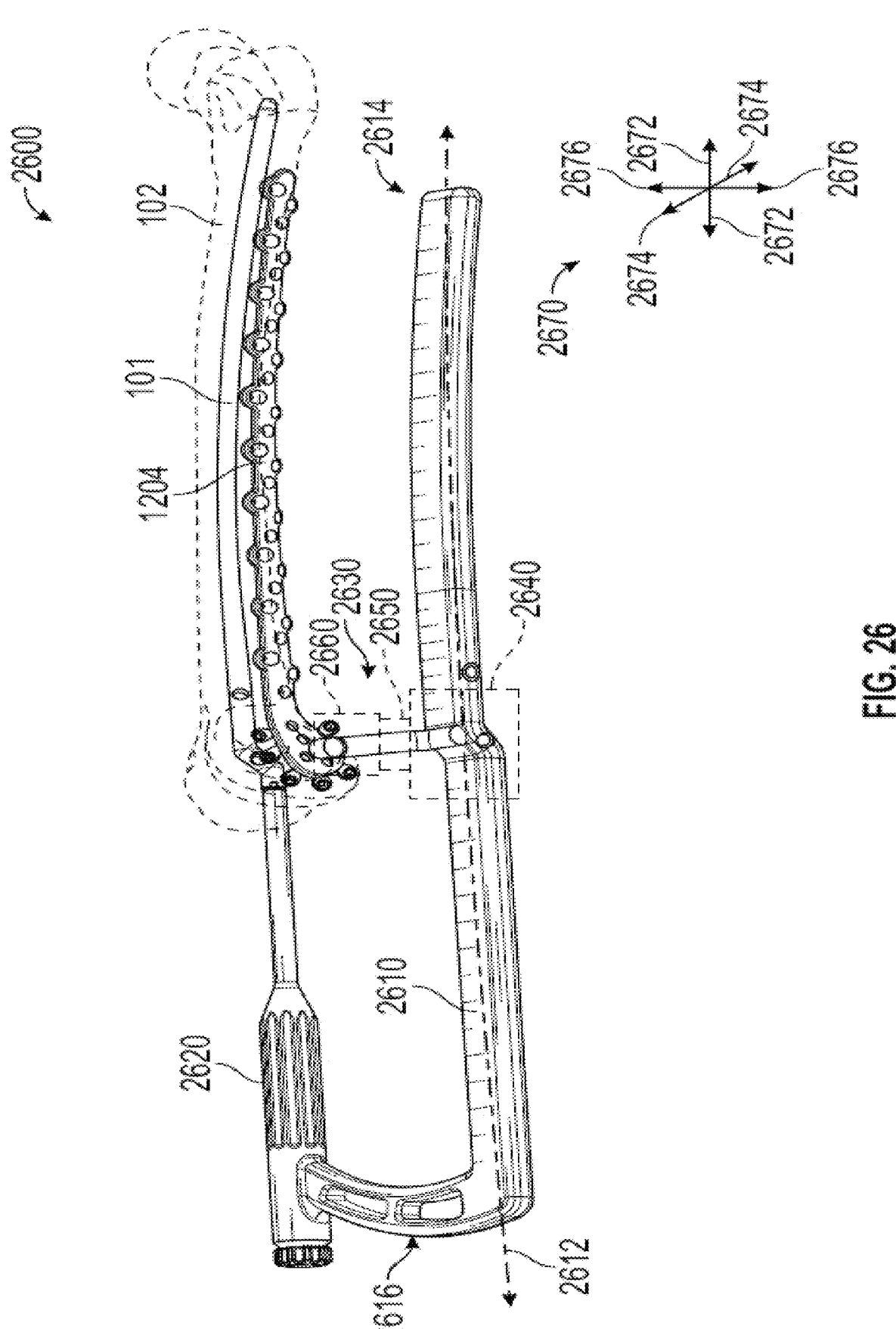
FIG. 26 is a perspective view of a combined inserter, according to one embodiment.

FIG. 26 is a perspective view of a combined inserter 2600, according to one embodiment. The combined inserter 2600 is an inserter that enables a surgeon to deploy both an intramedullary nail, such as intramedullary nail 101, and a bone plate, such as bone plate 1204, using a single instrument.

The combined inserter 2600 may include a body 2610, an intramedullary nail coupler 2620, and a bone plate coupler 2630. The body 2610 includes a longitudinal axis 2612, a distal end 2614, and a proximal end 2616. The body 2610 is coupled to the intramedullary nail coupler 2620 and the bone plate coupler 2630.

An intramedullary nail coupler 2620 is a coupler that can couple the combined inserter 2600 to an intramedullary nail, such as intramedullary nail 101. The intramedullary nail coupler 2620 serves to orient, guide, drive, and/or position an intramedullary nail 101 for deployment inside a patient. The combined inserter 2600 may have certain structures, features, and functions, operations, and configuration similar to that of the inserter 300a described in relation to FIG. 3A-3B. For example, the intramedullary nail coupler 2620 may correspond in design and configuration to the handle 310 and driver 320 discussed in relation to inserter 300a, with their constituent components. FIG. 26 illustrates the intramedullary nail coupler 2620 coupled to the intramedullary nail 101 with the intramedullary nail 101 inserted into an intramedullary canal of a long bone (e.g., a femur 102).

A bone plate coupler 2630 is a coupler that can couple the combined inserter 2600 to a bone plate, such as bone plate 1204. The bone plate coupler 2630 serves to orient, guide, drive, and/or position a bone plate, such as bone plate 1204, for deployment inside a patient. The bone plate coupler 2630 distinguishes the combined inserter 2600 from the inserter 300*a* and inserter 300*b*. Advantageously, the bone plate coupler 2630 includes one or more features that facilitate positioning and orienting the bone plate 1204 during deployment.

In one embodiment, the bone plate coupler 2630 includes a longitudinal translation feature 2640, a transverse feature 2650, and a rotational feature 2660. FIG. 26 illustrates a three-dimensional axis 2670. The three-dimensional axis 2670 includes a cephalad-caudal axis 2672, a medial-lateral axis 2674, and an anterior-posterior axis 2676.

Figure 27:
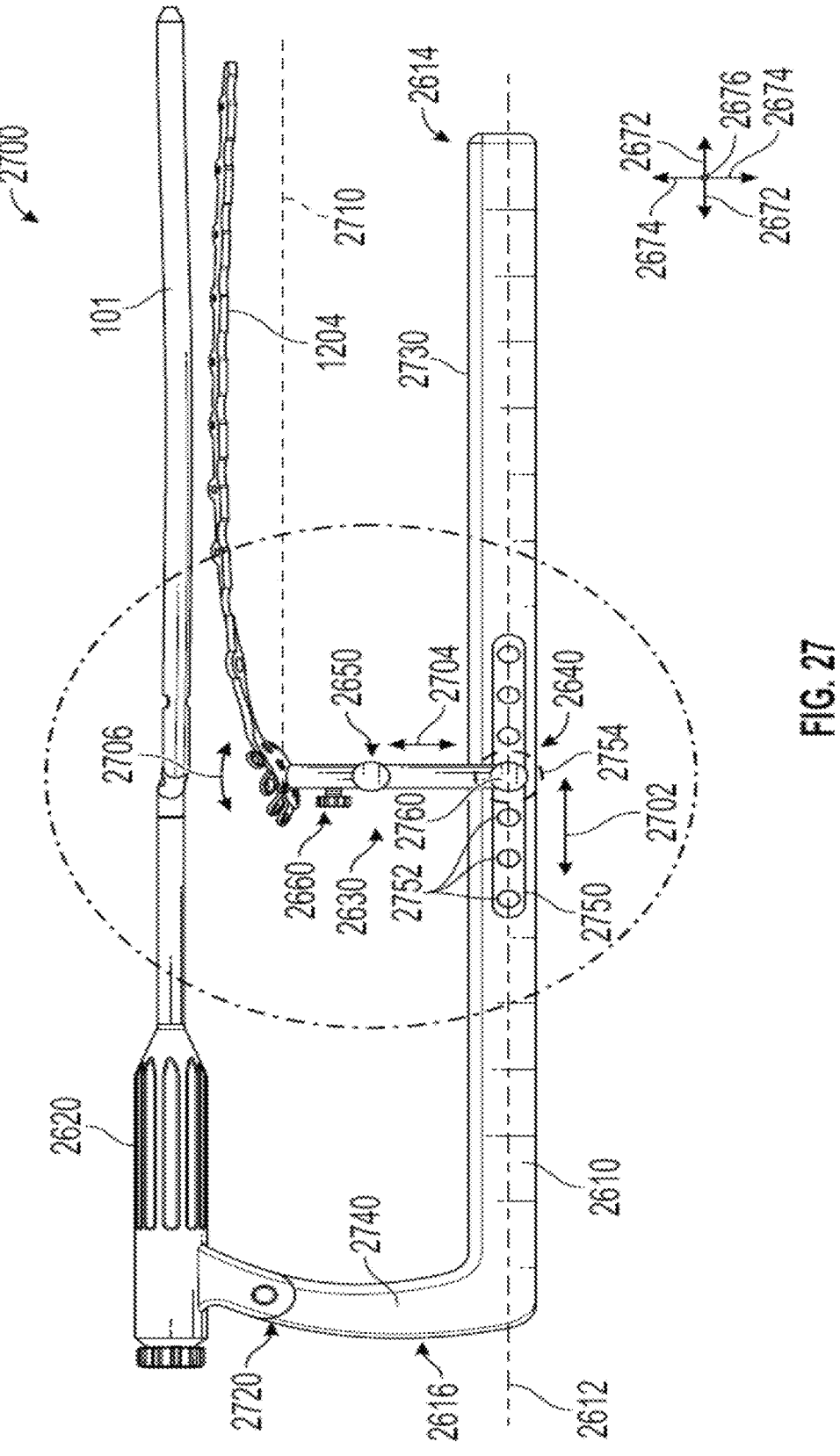
FIG. 27 is a perspective view of a combined inserter, according to one embodiment.

FIG. 27 is a perspective view of a combined inserter 2700, according to one embodiment. The combined inserter 2700 includes structures, features, and functions, operations, and configuration very similar to those of the combined inserter 2600 described in relation to FIG. 26, with like components having like numbers. Accordingly, the combined inserter 2700 may include a body 2610, longitudinal axis 2612, distal end 2614, proximal end 2616, intramedullary nail coupler 2620, bone plate coupler 2630, and the like. The combined inserter 2700 includes embodiments of a longitudinal translation feature 2640, transverse feature 2650, and rotational feature 2660. Those of skill in the art will appreciate that a variety of mechanical joints, mechanisms, and apparatuses may be used to implement the longitudinal translation feature 2640, transverse feature 2650, and rotational feature 2660. The present disclosure includes one or more examples.

A longitudinal translation feature 2640 is a feature that can position and re-position a bone plate coupler 2630 along an axis (e.g., longitudinal axis 2612). The longitudinal translation feature 2640 serves to enable and facilitate translation of the bone plate coupler 2630 along the longitudinal axis 2612 between the proximal end 2616 and the distal end 2614 (see arrows 2702). The longitudinal axis 2612 runs generally parallel to the cephalad-caudal axis 2672 during deployment. A transverse feature 2650 is a feature that can position and re-position a bone plate coupler 2630 along an axis. The transverse feature 2650 serves to enable and facilitate translation of the bone plate coupler 2630 along a transverse axis (see arrows 2704) that is transverse to the longitudinal axis 2612. In one embodiment, the transverse axis can be the medial-lateral axis 2674. A rotational feature 2660 is a feature that can position and re-position a bone plate coupler 2630 about an axis. The rotational feature 2660 serves to enable and facilitate rotation of a bone plate about a longitudinal bone plate axis 2710 (see arrows 2706).

In one embodiment, the combined inserter 2700 includes an intramedullary nail coupler 2620 that includes a coupling 2720. The coupling 2720 is a mechanism that enables a user to releasably connect the intramedullary nail coupler 2620 to the body 2610. In one embodiment, the coupling 2720 is a bolt that threads into threads of an opening of an arm that connects the intramedullary nail coupler 2620 and the body 2610.

In certain embodiments, the combined inserter 2700 may include a single apparatus that includes both an intramedullary nail coupler 2620 and a bone plate coupler 2630. In another embodiment, a user may use a an independent intramedullary nail coupler 2620 and an independent bone plate coupler 2630. These independent intramedullary nail coupler 2620 and an independent bone plate coupler 2630 may be connectable using a mechanism such as coupling 2720 for example.

In one embodiment, the combined inserter 2700 may include a separate intramedullary nail coupler 2620 and a separate bone plate coupler 2630 that can be coupled pre-operatively or intraoperatively using one or more couplers such as coupling 2720 for example. Alternatively, or in addition, the combined inserter 2700 may include a separate intramedullary nail coupler 2620 and a separate bone plate coupler 2630 or a combined intramedullary nail coupler 2620 and bone plate coupler 2630 that are coupled to a intramedullary nail 101 and/or a bone plate 1204 each preoperatively or intraoperatively using for example a coupler of the intramedullary nail coupler 2620 and/or a coupler of the bone plate coupler 2630.

In the illustrated embodiment, the body 2610 of the combined inserter 2700 includes a distal handle 2730 near the distal end 2614 and a proximal handle 2740 near the proximal end 2616. As used herein, a "handle" refers to a structure used to hold, control, or manipulate a device, apparatus, component, tool, or the like. A "handle" may be designed to be grasped and/or held using one or two hands of a user.

The present disclosure includes a variety of designs for a separate inserter for a intramedullary nail 101, a separate inserter for a bone plate 1204, and/or a combined inserter. For example, the inserter may be implemented as a combined inserter (both intramedullary nail 101 and bone plate 1204), as two separate inserters; a separate one for the intramedullary nail 101 and a separate one for the bone plate 1204. Alternatively, or in addition, the inserter may be implemented as two separate inserters (e.g., separate one for the intramedullary nail 101 and a separate one for the bone plate 1204) that connect to each other once one or more implants are deployed inside the body of the patient to become a combined inserter and/or connects to one or more of the implants once one or more implants are deployed inside the body of the patient.

Also a variety of surgical techniques can be used with the various embodiments of the inserter (both a combined inserter and two combinable inserters). In one example, the intramedullary nail 101 may be inserted with a first inserter and the bone plate 1204 may then be inserted with a separate inserter. The bone plate 1204 may then be affixed to the bone and screws are put through either distally to go through the intramedullary nail 101 or miss the nail or proximally to either miss the intramedullary nail 101 or to miss a part of another implant such as a hip prosthesis. Alternatively, the screws may be deployed to go through the bone plate 1204 and go through a bone that does not include a intramedullary nail 101 or other prosthesis.

In another embodiment, the surgical technique may include inserting the intramedullary nail 101 with an intramedullary nail inserter and then connecting a bone plate inserter to the intramedullary nail inserter or the intramedullary nail in a modular way. The connected intramedullary nail inserter and bone plate inserter may then register off of each other to enable a user to connect the bone plate to the intramedullary nail 101 via the now combined inserter. Advantageously, the combined inserter can include nail engagement openings 3312 and/or nail avoidance openings 3314 that give the surgeon the option of securing the bone plate 1204 to the intramedullary nail 101 or only to the bone missing both a intramedullary nail 101 and/or another part of an implant that is deployed or will be deployed into the patient.

Figure 28:
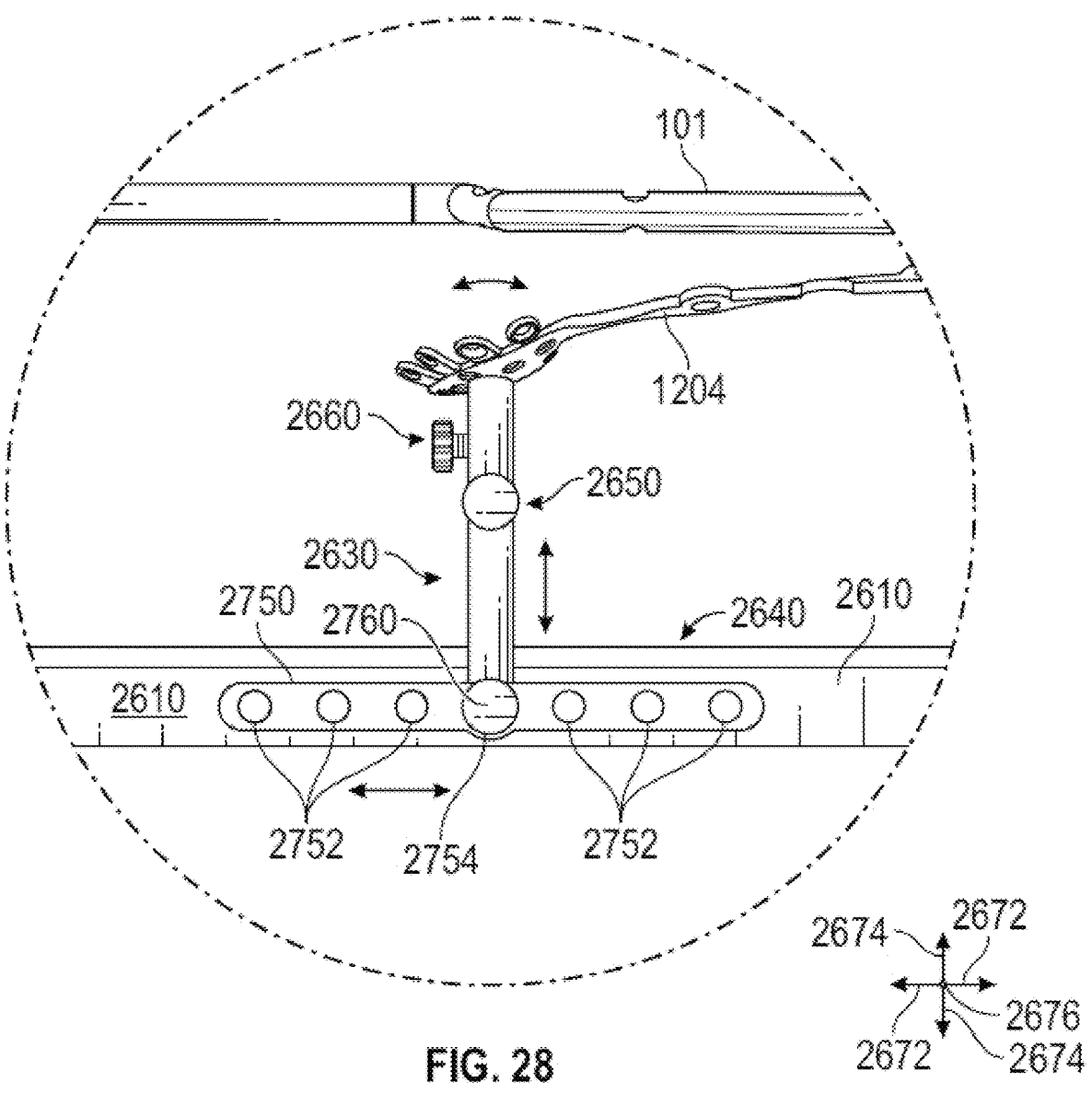
FIG. 28 is a close up perspective view of combined inserter, according to one embodiment.

FIG. 28 is a close up perspective view of combined inserter 2700, according to one embodiment. FIG. 28 illustrates one example of a longitudinal translation feature 2640. In the illustrated embodiment, the longitudinal translation feature 2640 may include a track 2750 positioned in the body 2610 between the distal end 2614 and the proximal end 2616. The longitudinal translation feature 2640 may also include a latch 2760. "Track" refers to a physical course or way. (Search "track" on wordhippo.com. WordHippo, 2022. Web. Modified. Accessed 9 Aug. 2022.) In certain embodiments, a track is a structure configured to accept another object that can be moved to different positions, on, in, along, or within the track. "Latch" refers to a type of mechanical fastener that joins two (or more) objects or surfaces while allowing for their regular separation. A latch may engage another piece of hardware on a mounting surface. Depending upon the type and design of the latch, this engaged hardware may be referred to as a keeper or strike. (Search "latch" on Wikipedia.com Aug. 1, 2022. CC-BY-SA 3.0 Modified. Accessed Aug. 9, 2022.) "Position" refers to a place or location. (Search "position" on wordhippo.com. WordHippo, 2022. Web. Modified. Accessed 9 Aug. 2022.)

The track 2750 may include one or more offset positions 2752 and a nail alignment position 2754. An offset position 2752 is a position within the track 2750 that is different from or offset from the nail alignment position 2754. An offset position 2752 positions the bone plate coupler 2630 such that a bone plate coupled to the bone plate coupler 2630 is offset in relation to an intramedullary nail coupled to the intramedullary nail coupler 2620. An intramedullary nail and a bone plate are offset when the position and orientation of the intramedullary nail and bone plate relative to each other is not the desired orientation and alignment that the intramedullary nail and bone plate will have when both are deployed within a patient.

A nail alignment position 2754 is a position within the track 2750, or another component of the longitudinal translation feature 2640, where an intramedullary nail coupled to the intramedullary nail coupler 2620 is aligned with a bone plate coupled to the bone plate coupler 2630. An intramedullary nail and a bone plate are aligned when the position and orientation of the intramedullary nail and bone plate relative to each other is the desired orientation and alignment that the intramedullary nail and bone plate will have when both are deployed within a patient.

Advantageously, a user can rely on the intramedullary nail and bone plate being aligned relative to each other when at least the longitudinal translation feature 2640 of the bone plate coupler 2630 is in the nail alignment position 2754. Said another way, the nail alignment position 2754 is a position that aligns the intramedullary nail and bone plate coupled to the combined inserter 2700 for deployment within a patient.

A nail alignment position 2754 of a longitudinal translation feature 2640 can be used to realign the intramedullary nail and bone plate after the bone plate coupler 2630 has been repositioned using the longitudinal translation feature 2640. Those of skill in the art will appreciate that the transverse feature 2650 and/or rotational feature 2660 may also have a nail alignment position. These nail alignment positions may serve the same or a similar purpose as the nail alignment position 2754 with respect to the associated feature (e.g., transverse feature 2650, rotational feature 2660). In certain embodiments, the nail alignment positions of the longitudinal translation feature 2640, transverse feature 2650, and/or rotational feature 2660 may be part of a deployment configuration.

The latch 2760 serves to retain or secure the bone plate coupler 2630 in one of the offset positions 2752 or the nail alignment position 2754 and to permit the bone plate coupler 2630 to be moved to a different offset position 2752 and/or the nail alignment position 2754. In one embodiment, the latch 2760 is a spring pin and the offset position 2752 and/or nail alignment position 2754 are openings that receive the spring pin.

Figure 29:
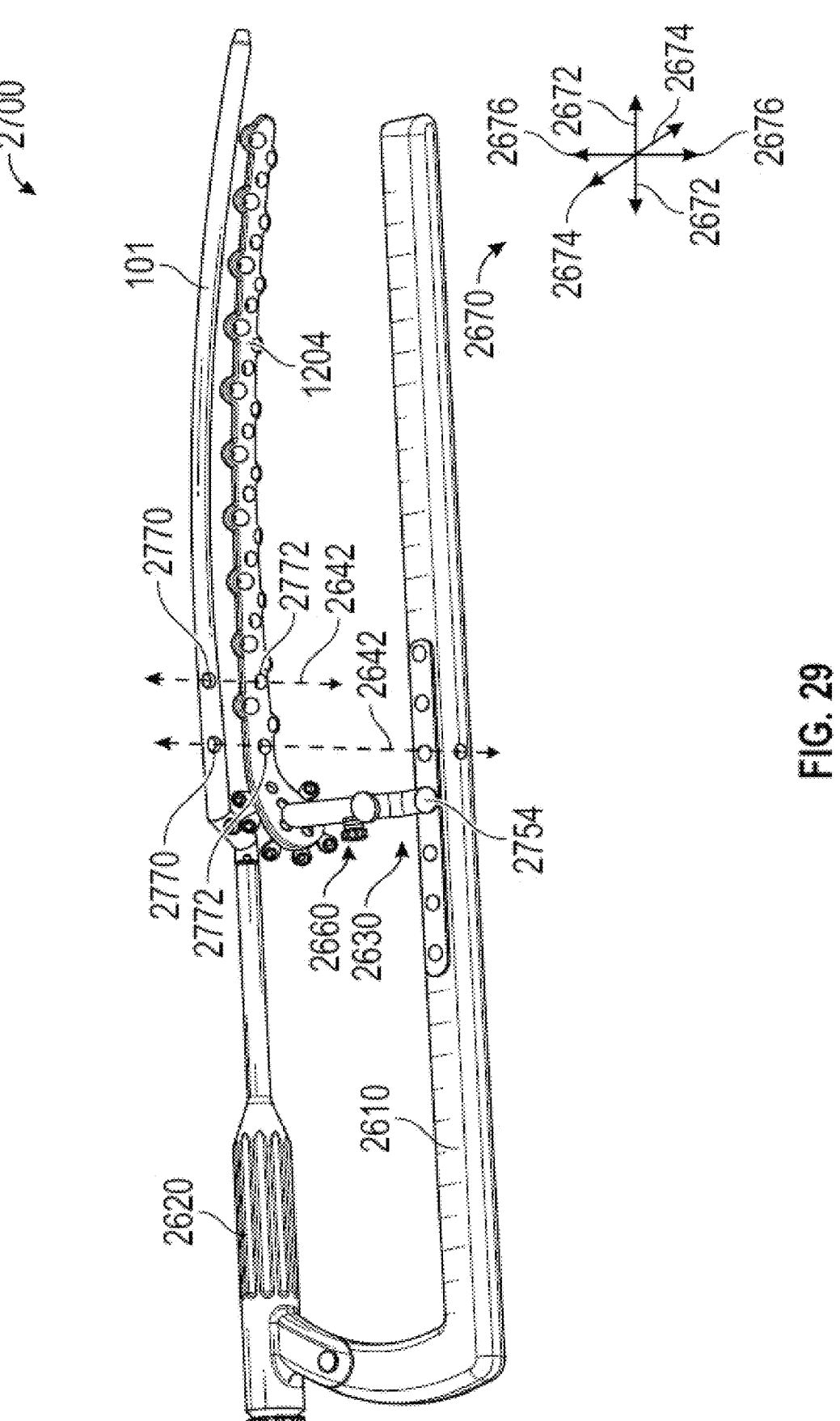
FIG. 29 is a perspective view of a combined inserter, according to one embodiment.

FIG. 29 is a perspective view of a combined inserter 2700, according to one embodiment. The combined inserter 2700 is coupled to an intramedullary nail 101 and a bone plate 1204. FIG. 29 illustrates the position and/or orientation of the intramedullary nail 101 and the bone plate 1204 with the longitudinal translation feature 2640 in the nail alignment position 2754. In the illustrated embodiment, the intramedullary nail 101 includes one or more fastener openings 2770 and the bone plate 1204 includes one or more fastener openings 2772.

Those of skill in the art will appreciate that deployment of the intramedullary nail 101 and the bone plate 1204 can be challenging where the bone plate 1204 is deployed percutaneously and the intramedullary nail 101 is deployed within the intramedullary canal. The two implants can be difficult to align and position based on visual cues. Certain imaging technologies can be used such as fluoroscopy, however their use may be cost prohibitive and/or expose the patient to more radiation than desired.

Advantageously, moving the longitudinal translation feature 2640 to the nail alignment position 2754 aligns at least one fastener opening 2772 of the bone plate 1204 and at least one fastener opening 2770 of the intramedullary nail 101 such that deployment of a fastener through the fastener opening 2772 engages the at least one fastener opening 2770 of the intramedullary nail 101. The alignment is indicated by arrows 2642. In this manner, a user can readily fixate the bone plate 1204 to the intramedullary nail 101. In certain embodiments, certain openings in the bone plate 1204 may be used to deploy fasteners that engage the bone plate 1204 and bone 102 but miss or do not contact the intramedullary nail 101 or another implant. In certain embodiments, the body 2610 may include an opening that aligns with a fastener opening 2770 of the intramedullary nail 101 and a fastener opening 2772 of the bone plate 1204.

Those of skill in the art will appreciate that deployment of fasteners through the bone plate 1204 and into the long bone (e.g., 102) without contacting an existing implant in the bone (e.g., intramedullary nail, knee implant stem, hip implant stem, etc.) is more challenging towards a proximal end of the long bone than the distal end. This may be due in part to a higher area within the bone being occupied by implant structures than bone material towards the proximal end than towards the distal end of the long bone. Advantageously, the openings in the bone plate 1204 that guide a fastener to miss striking a deployed implant in the long bone assist in surgeon in deploying a fastener that can provide optimal fixation to promote proper healing.

Figure 30:
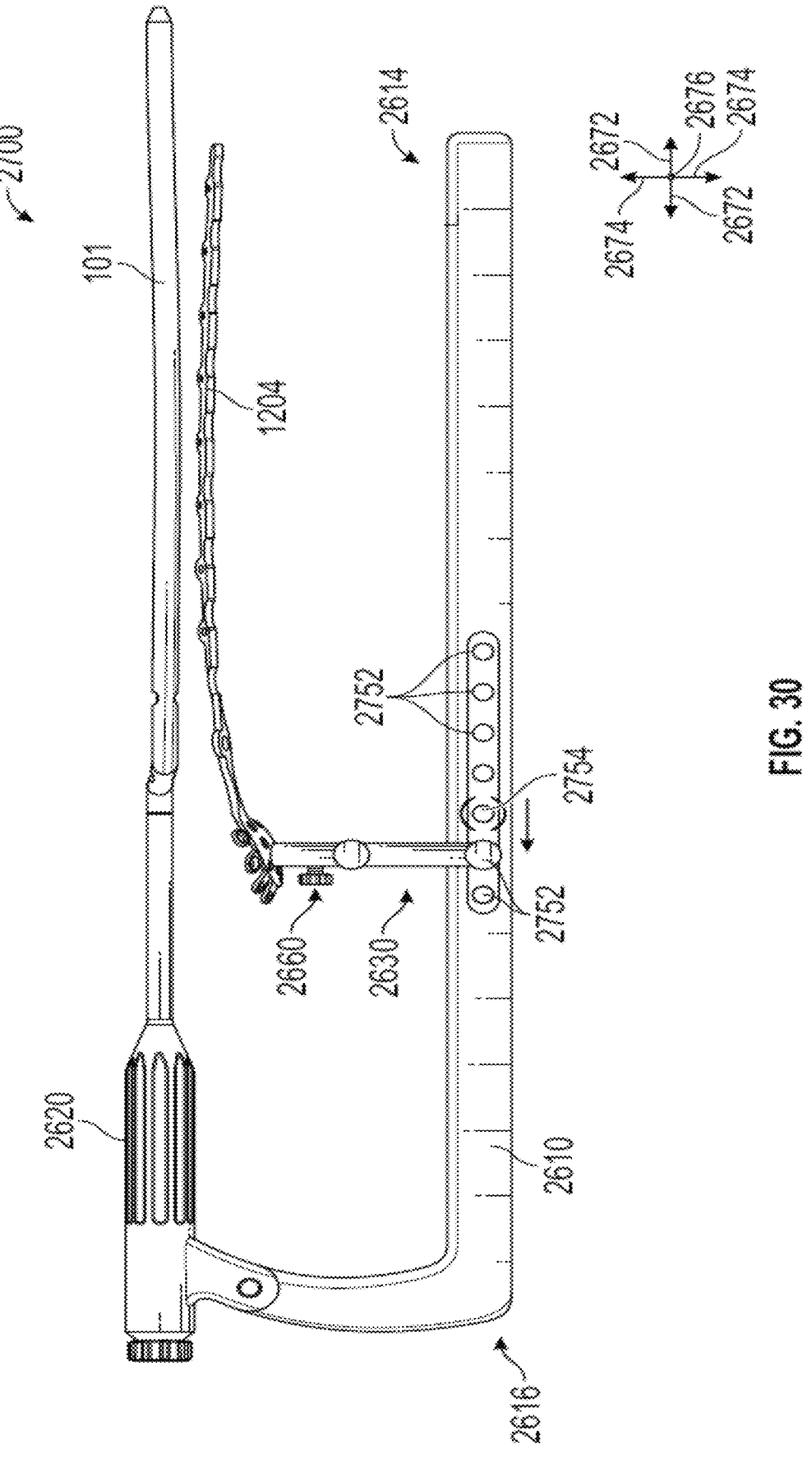
FIG. 30 is a perspective view of a combined inserter, according to one embodiment.

FIG. 30 is a perspective view of a combined inserter 2700, according to one embodiment. The combined inserter 2700 is coupled to an intramedullary nail 101 and a bone plate 1204. FIG. 30 illustrates the position and/or orientation of the intramedullary nail 101 and the bone plate 1204 with the longitudinal translation feature 2640 in the one of the offset positions 2752 closer to the proximal end 2616.

In certain embodiments, moving the bone plate coupler 2630 closer to the proximal end 2616 by way of the longitudinal translation feature 2640 may cause the intramedullary nail 101 to extend more distally than the bone plate 1204. Consequently, advancement of the combined inserter 2700 toward a bone 102 of a patient causes the intramedullary nail 101 to enter an intramedullary canal of the bone 102 before the bone plate 1204 percutaneously advances along a side of the bone 102.

Figure 31:
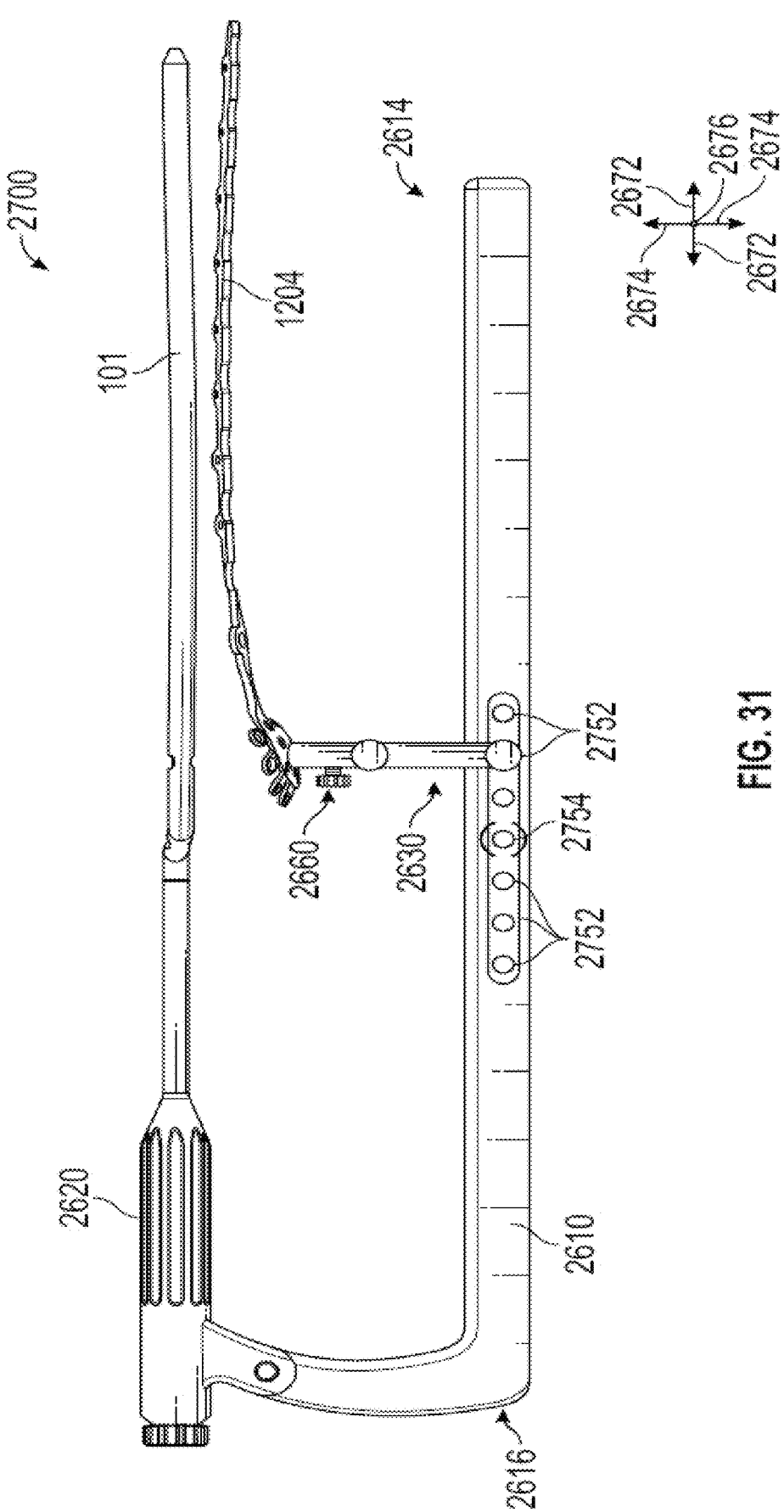
FIG. 31 is a perspective view of a combined inserter, according to one embodiment.

FIG. 31 is a perspective view of a combined inserter 2700, according to one embodiment. The combined inserter 2700 is coupled to an intramedullary nail 101 and a bone plate 1204. FIG. 31 illustrates the position and/or orientation of the intramedullary nail 101 and the bone plate 1204 with the longitudinal translation feature 2640 in the one of the offset positions 2752 closer to the distal end 2614.

In certain embodiments, moving the bone plate coupler 2630 closer to the distal end 2614 by way of the longitudinal translation feature 2640 may cause the bone plate 1204 to extend more distally than the intramedullary nail 101. Consequently, advancement of the combined inserter 2700 toward a bone 102 of a patient causes the bone plate 1204 percutaneously advance along a side of the bone 102 before the intramedullary nail 101 enters an intramedullary canal of the patient.

Figure 32:
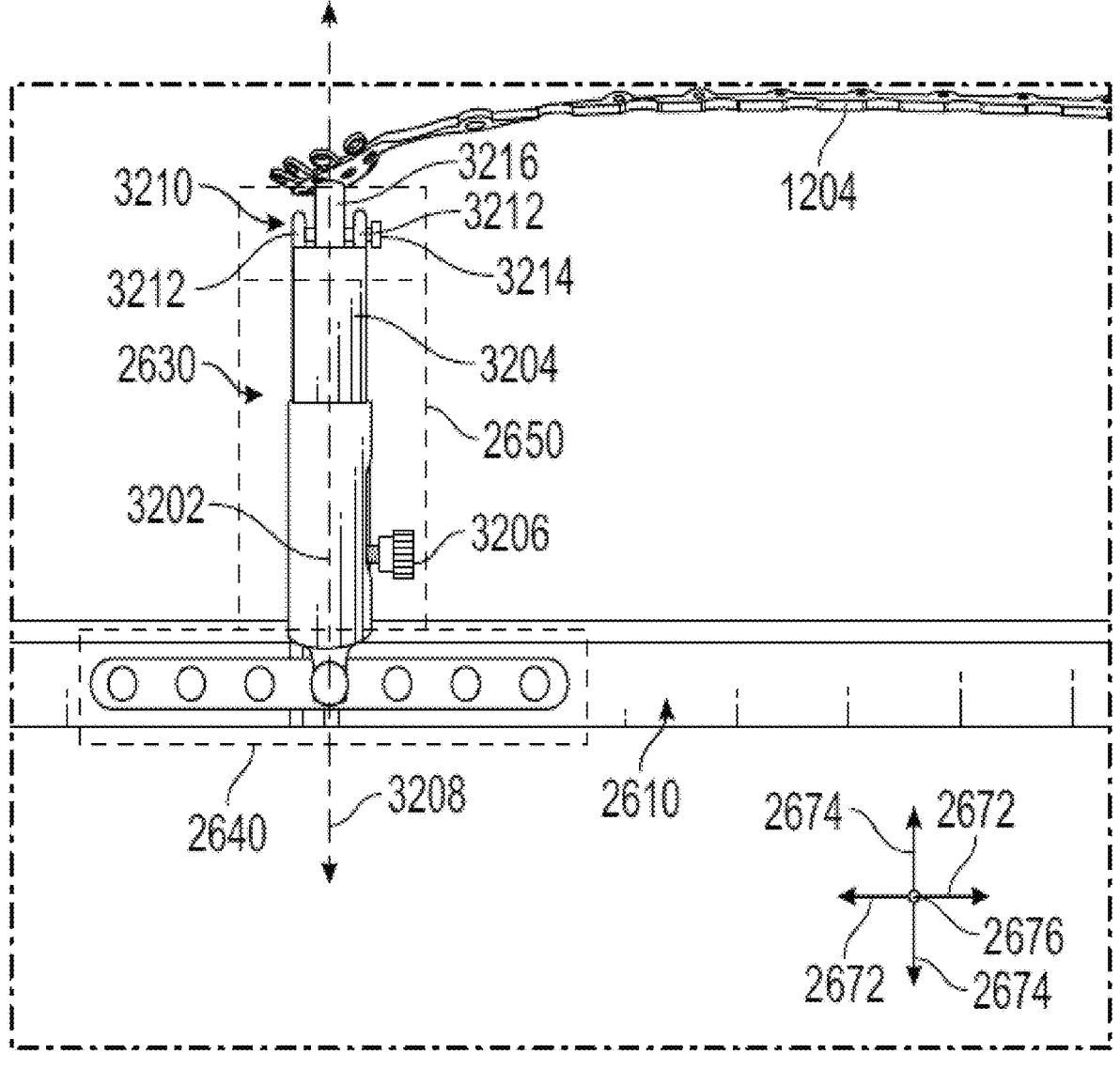
FIG. 32 is a close up perspective view of a combined inserter, according to one embodiment.

FIG. 32 is a close up perspective view of a combined inserter 2700, according to one embodiment. FIG. 32 illustrates one example of a transverse feature 2650. In the illustrated embodiment, the transverse feature 2650 may include a base 3202, a telescoping member 3204, and a fastener 3206. The base 3202 may extend from the body 2610 towards the intramedullary nail coupler 2620. The telescoping member 3204 is configured to fit within the base 3202. The fastener 3206 is configured to releasably secure the telescoping member 3204 within the base 3202. In one embodiment, the fastener 3206 is a set screw or a thumb screw.

As used herein, a "base" refers to a main or central structure, component, or part of a structure. A base is often a structure, component, or part upon which, or from which other structures extend into, out of, away from, are coupled to, or connect to. A base may have a variety of geometric shapes and configurations. A base may be rigid or pliable. A base may be solid or hollow. A base can have any number of sides. In one embodiment, a base may include a housing, frame, or framework for a larger system, component, structure, or device. In certain embodiments, a base can be a part at the bottom or underneath a structure designed to extend vertically when the structure is in a desired configuration or position.

As used herein, a "set screw" refers to a type of screw generally used to secure a first object within, or against, second object, usually without using a nut. Set screws can be headless, meaning that the screw is fully threaded and has no head projecting past the thread's major diameter. If a set screw does have a head, the thread may extend to the head. A set screw can be driven by an internal-wrenching drive, such as a hex socket (Allen), star (Torx), square socket (Robertson), or a slot. A set screw can be driven by a knob on or part of a head of the set screw. The knob may be sized to facilitate rotation by a user using their fingers and may be referred to as a thumb screw. In one embodiment, the set screw passes through a threaded hole in the second object (an outer object) and is tightened against the first object (an inner object) to prevent the inner object from moving relative to the outer object. The set screw can exert a compressional and/or clamping force through an end of the set screw that projects through the threaded hole. (Search "set screw" on Wikipedia.com Aug. 17, 2020. Modified. Accessed Jan. 6, 2020.)

In one embodiment, the transverse feature 2650 is configured to bias the bone plate 1204 towards the long bone (e.g., femur 102) and move the bone plate 1204 away from the bone in response to a force directed away from the long bone (e.g., femur 102). For example, the transverse feature 2650 may include a bias member such as a spring that biases the bone plate 1204 towards the long bone. The bias member can help a user operate the transverse feature 2650 such that the transverse feature 2650 is in a deployment configuration.

In certain embodiments, the base 3202 and telescoping member 3204 are aligned with a transverse axis 3208. Extending or retracting the telescoping member 3204 can advance or retract a bone plate 1204 along the transverse axis 3208. In one embodiment, the transverse axis 3208 is parallel to the medial-lateral axis 2674.

FIG. 32 illustrates one example of a rotational feature 2660. The rotational feature 2660 connects a bone plate 1204 to the transverse feature 2650. The rotational feature 2660 enables the bone plate 1204 to rotate about the longitudinal bone plate axis 2710. In one embodiment, the rotational feature 2660 includes a pivot joint 3210 that enables the bone plate 1204 to move in at least two directions relative to the bone plate coupler 2630. In one embodiment, the pivot joint 3210 enables the bone plate 1204 to pivot and move posteriorly and/or anteriorly (generally along the anterior-posterior axis 2676). "Pivot" refers to a shaft or pin on which a mechanism turns or oscillates. (Search "pivot" on wordhippo.com. WordHippo, 2022. Web. Accessed 9 Aug. 2022.)

In the illustrated embodiment, the rotational feature 2660 is embodied as a clevis joint having a pair of arms 3212 and an axle 3214 that extends through holes in the arms and engages a mount 3216 that is connected to the bone plate 1204. In another embodiment, the rotational feature 2660 may be embodied using a ball and socket configuration. "Ball" refers to a solid or hollow sphere, or part thereof (Search "ball" on wordhippo.com. WordHippo, 2022. Web. Modified. Accessed 9 Aug. 2022.) "Socket" refers to an opening, hollow, or space into which a plug or other connecting part is designed to fit. (Search "socket" on wordhippo.com. WordHippo, 2022. Web. Modified. Accessed 9 Aug. 2022.) "Axle" refers to a pin or spindle on which a wheel revolves, or which revolves with a wheel. An axle may also refer to a transverse bar or shaft connecting the opposite wheels or parts of a vehicle or other apparatus. (Search "axle" on wordhippo.com. WordHippo, 2022. Web. Modified. Accessed 9 Aug. 2022.)

As explained above, each of the longitudinal translation feature 2640, transverse feature 2650, and rotational feature 2660 may include a deployment configuration. A deployment configuration is a configuration, setting, position, arrangement, orientation, and/or feature of an apparatus, structure, component, or feature that provides for a desirable deployment position for an intramedullary nail 101 and/or bone plate 1204 coupled to the combined inserter 2700. In certain embodiments, one or more aspects of the longitudinal translation feature 2640, transverse feature 2650, and/or rotational feature 2660 may include an indicator that identifies when the longitudinal translation feature 2640, transverse feature 2650, and rotational feature 2660 is in the deployment configuration. Said another way, a deployment configuration is an arrangement that position two implants (e.g., intramedullary nail 101 and bone plate 1204) relative to each other such that a user can deploy bone screws or other fasteners in order to and engage the intramedullary nail 101 and/or to specifically miss, not engage, the intramedullary nail 101. Components of a deployment indicator can be identified using one or more indicators (visual and/or tactile).

As used herein, an "indicator" refers to an apparatus, device, component, system, assembly, mechanism, hardware, software, firmware, circuit, module, set of data, text, number, code, symbol, a mark, or logic structured, organized, configured, programmed, designed, arranged, or engineered to convey information or indicate a state, condition, mode, context, location, or position to another apparatus, device, component, system, assembly, mechanism, hardware, software, firmware, circuit, module, and/or a user of an apparatus, device, component, system, assembly, mechanism, hardware, software, firmware, circuit, module that includes, or is associated with the indicator. The indicator can include one or more of an audible signal, a token, a presence of a signal, an absence of a signal, a tactile signal, a visual signal or indication, a visual marker, a visual icon, a visual symbol, a visual code, a visual mark, and/or the like. In certain embodiments, "indicator" can be with a an adjective describing the indicator. For example, a "mode indicator" is an indicator that identifies or indicates a mode. "Set" refers to a collection of objects. A set can have zero or more objects in the collection. Generally, a set includes one or more objects in the collection.

Of course embodiments of the combined inserter 2700 may include one or more of the longitudinal translation feature 2640, transverse feature 2650, and rotational feature 2660. In this manner, the combined inserter 2700 can facilitate repositioning of a coupled bone plate 1204 relative to a coupled intramedullary nail 101 as needed for a user.

Figures 33, 34:
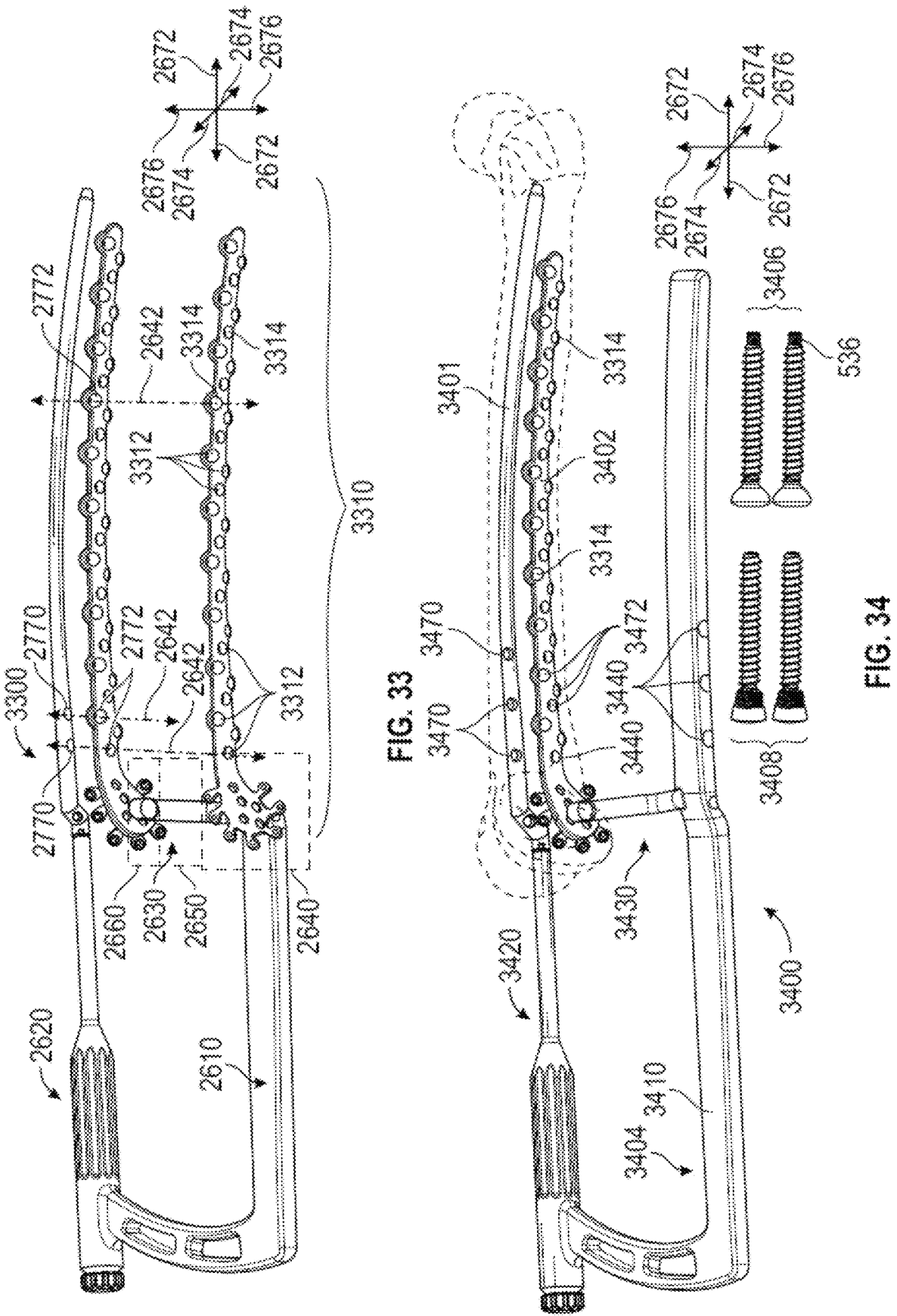
FIG. 33 is a perspective view of a combined inserter, according to one embodiment.
FIG. 34 is a perspective view of a femur fixation system, according to one embodiment.

FIG. 33 is a perspective view of a combined inserter 3300, according to one embodiment. The combined inserter 3300 is coupled to an intramedullary nail 101 and a bone plate 1204. FIG. 33 illustrates the position and/or orientation of the intramedullary nail 101 and the bone plate 1204 with the longitudinal translation feature 2640 in the nail alignment position 2754 (e.g., a deployment configuration). Alternatively, or in addition, one or more of the transverse feature 2650 and/or rotational feature 2660 may also be in a deployment configuration. In the illustrated embodiment, the intramedullary nail 101 includes one or more fastener openings 2770 and the bone plate 1204 includes one or more fastener openings 2772.

The combined inserter 3300 may serve to specifically address a challenge deploying a bone plate 1204 percutaneously and an intramedullary nail 101 within the intramedullary canal. In one embodiment, the combined inserter 3300 includes a guide section 3310. The guide section 3310 provides a guide for a surgeon when the surgeon deploys fasteners.

Advantageously, in certain embodiments, the guide section 3310 is external to the body of the patient and aligns with both the intramedullary nail 101 and the bone plate 1204 when those implants are in the deployment configuration. In the illustrated embodiment, the guide section 3310 includes a set of nail engagement openings 3312 and a set of nail avoidance openings 3314. In one embodiment, the nail engagement openings 3312 and nail avoidance openings 3314 align with at least one fastener opening of the bone plate 1204.

A nail engagement openings 3312 is an opening positioned, oriented, and/or configured such that a fastener deployed through the nail engagement openings 3312 can engage a fastener opening in a positioned intramedullary nail 101. A nail avoidance openings 3314 is an opening positioned, oriented, and/or configured such that a fastener deployed through the nail avoidance openings 3314 will not and/or cannot engage a fastener opening of an intramedullary nail 101. Alternatively, or in addition, a nail avoidance openings 3314 may be configured such that a fastener deployed through the nail avoidance openings 3314 will not contact an intramedullary nail 101. Said another way, the nail avoidance openings 3314 may be configured such that a fastener passing through the nail avoidance openings 3314 will miss an intramedullary nail 101 inside the bone. Those of skill in the art will appreciate that the nail engagement openings 3312 and/or nail avoidance openings 3314 may also align with a corresponding nail engagement opening and/or nail avoidance opening of the bone plate 1204.

In the illustrated embodiment, the guide section 3310 includes a similar contour, shape, size and configuration as the bone plate 1204. Furthermore, certain openings in the guide section 3310 may be marked to indicate which ones are nail engagement openings 3312 and which ones are nail avoidance openings 3314. Alternatively, or in addition, in one embodiment the guide section 3310 may not be shaped like the bone plate 1204 but may still include guide section 3310 and/or nail avoidance openings 3314 that assist a surgeon in targeting fasteners that engage with one of the intramedullary nail 101 and the bone plate 1204 or both.

Advantageously, placing one or more of the longitudinal translation feature 2640, transverse feature 2650, and/or rotational feature 2660 in the deployment configuration can align at least one fastener opening 2772 of the bone plate 1204 and at least one fastener opening 2770 of the intramedullary nail 101. With the bone plate 1204 and intramedullary nail 101 aligned, a surgeon can determine which of the nail engagement openings 3312 and/or the nail avoidance openings 3314 to use to provide the desired fixation between the implants and the bone and/or the implants and each other.

FIG. 34 is a perspective view of a femur fixation system 3400, according to one embodiment. The femur fixation system 3400 may include components, apparatus, devices, features, and/or functions, operations, and configurations similar to or the same as embodiments described herein. Accordingly, the femur fixation system 3400 may include an intramedullary nail 3401, a bone plate 3402, a combined inserter 3404, a set of nail engagement fasteners 3406, and a set of nail avoidance fasteners 3408. The intramedullary nail 3401 includes a set of nail fastener openings 3470, which may be similar to fastener openings 2770. A nail fastener openings 3470 is an opening in an intramedullary nail configured to accept a fastener. In one embodiment, the nail fastener openings 3470 are configured to accept a fastener that engages the intramedullary nail 3401. The bone plate 3402 includes a set of plate fastener openings 3472, which may be similar to fastener openings 2772.

A plate fastener openings 3472 is an opening in a bone plate configured to accept a fastener. In one embodiment, the plate fastener openings 3472 may include at least one nail avoidance openings 3314. As noted, the nail avoidance openings 3314 may be identified by a marking. Alternatively, or in addition, the nail avoidance openings 3314 may be identifiable based on how openings are distributed along a bone plate 3402. For example, openings closer to the edges of a bone plate 3402 may be nail avoidance openings 3314 and openings between the edges may be nail engagement openings 3440.

As with other embodiments described herein, the combined inserter 3404 of the femur fixation system 3400 may include a body 3410 having a longitudinal axis 3412, a distal end 3414, and a proximal end 3416. The combined inserter 3404 may also include an intramedullary nail coupler 3420, a bone plate coupler 3430, and a set of nail engagement openings 3440. The intramedullary nail coupler 3420 is coupled to the body 3410 and configured to couple to the intramedullary nail 3401. The bone plate coupler 3430 is coupled to the body 3410 and configured to couple to the bone plate 3402.

In one embodiment, the body 3410 includes a set of nail engagement openings 3440 that align with at least one of the nail fastener openings 3470. The nail engagement openings 3440 may be outside the skin of a patient when the combined inserter 3404 is used to deploy an intramedullary nail 3401 and bone plate 3402 together. A user may use the nail engagement openings 3440 and plate fastener openings 3472 to target a fastener for deployment through the bone plate 3402 and into the nail fastener openings 3470 of the intramedullary nail 3401 to engage the intramedullary nail 3401. In one example, a user may deploy a nail engagement fasteners 3406 through the bone plate 3402 and into the nail fastener openings 3470 of the intramedullary nail 3401. Alternatively, or in addition, a user may deploy a nail avoidance fasteners 3408 through the bone plate 3402 and into the bone while avoiding the intramedullary nail 3401.

A nail engagement fastener 3406 is a fastener configured to engage with an intramedullary nail 3401. In one embodiment, the nail engagement fasteners 3406 engage with a bone plate 3402, bone, and the intramedullary nail 3401. In another embodiment, the nail engagement fasteners 3406 engages with bone and the intramedullary nail 3401. In certain embodiments, the nail engagement fasteners 3406 includes features to facilitate engaging the intramedullary nail 3401. For example, the nail engagement fasteners 3406 may include fine threads 536 configured to engage internal threads of a nail fastener openings 3470.

A nail avoidance fasteners 3408 is a fastener configured to with bone and/or a bone plate 3402 and not contact and/or engage with an intramedullary nail 3401. In another embodiment, the nail avoidance fasteners 3408 engages with bone and does not engage with the bone plate 3402 or contact or engage with the intramedullary nail 3401. In certain embodiments, the nail avoidance fasteners 3408 may include features to facilitate engaging bone. For example, a distal end of the nail avoidance fasteners 3408 may come to a point to facilitate piercing and engaging with bone.

After a desired number of nail engagement fasteners 3406 and/or nail avoidance fasteners 3408 are deployed, a user may remove the combined inserter 3404 and deploy additional fasteners into one, or both of, the bone plate 3402 and the intramedullary nail 3401.

Figure 35:
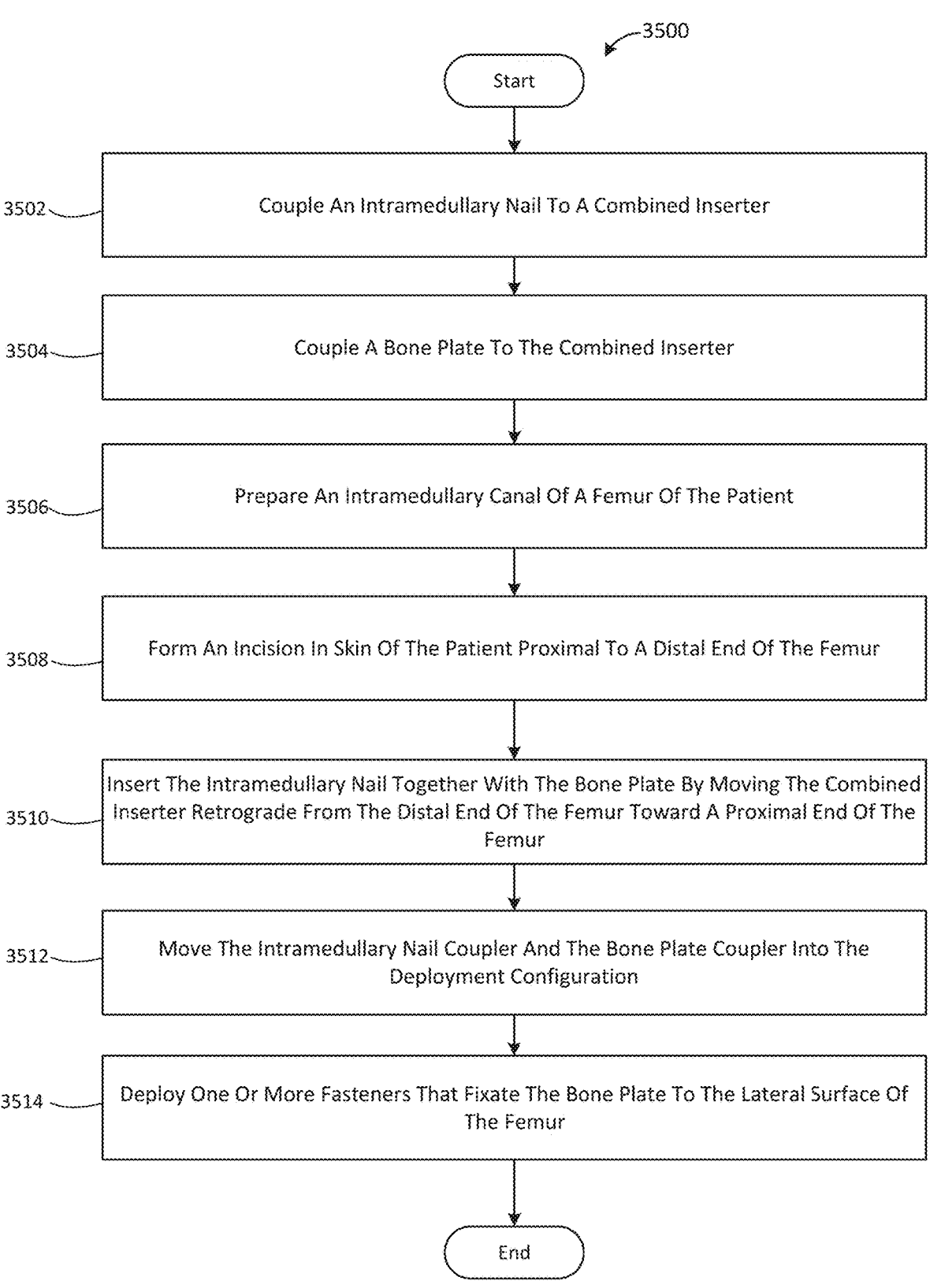
FIG. 35 illustrates one example of a method for stabilizing a bone fracture in a femur of a patient according to one embodiment.

FIG. 35 illustrates one example of a method 3500 for stabilizing a bone fracture in a femur of a patient according to one embodiment. In certain embodiments, the method 3500 begins and a user couples 3502 an intramedullary nail to a combined inserter. Next, a user couples 3504 a bone plate to the combined inserter. The combined inserter may an intramedullary nail coupler and a bone plate coupler each of which may include a deployment configuration.

Next, a user, such as a surgeon, prepares 3506 an intramedullary canal of a femur of the patient. In one embodiment, the intramedullary canal may extend from a distal end of the femur to a proximal end of the femur.

Next, a user, such as a surgeon, may form 3508 an incision in skin of the patient proximal to a distal end of the femur, the incision sized to accept the bone plate coupled to the combined inserter.

Next, a user, such as a surgeon, may insert 3510 the intramedullary nail together with the bone plate by moving the combined inserter retrograde from the distal end of the femur toward the proximal end of the femur. As the user inserts 3510 the intramedullary nail together with the bone plate, the intramedullary nail moves within the intramedullary canal and the bone plate moves percutaneously along a lateral surface of the femur. In one embodiment, inserting the intramedullary nail together with the bone plate may also include adjusting the bone plate coupler such that the bone plate can move in at least two directions relative to the bone plate coupler. This movement may facilitate deployment of the intramedullary nail together with the bone plate.

Next, a user, such as a surgeon, may move 3512 each of the intramedullary nail coupler and the bone plate coupler into their respective deployment configurations. Moving the intramedullary nail coupler and the bone plate coupler into their respective deployment configurations aligns the intramedullary nail and the bone plate.

The user then deploys 3514 one or more fasteners that fixate the bone plate to the lateral surface of the femur and the method 3500 ends.

As used herein, a "fixation" refers to an apparatus, instrument, structure, device, component, member, system, assembly, step, process, or module structured, organized, configured, designed, arranged, or engineered to connect two structures. The structures may one or the other or both manmade and/or biological tissues, hard tissues such as bones, teeth or the like, soft tissues such as ligament, cartilage, tendon, or the like. Typically, fixation is used as an adjective to describe a device or component or step in securing two structures such that the structures remain connected to each other in a desired position and/or orientation. Fixation devices can also serve to maintain a desired level of tension, compression, or redistribute load and stresses experienced by the two structures and can serve to reduce relative motion of one part relative to others. Examples of fixation devices are many and include both those for external fixation as well as those for internal fixation and include, but are not limited to pins, wires, Kirschner wires, screws, anchors, bone anchors, plates, bone plates, intramedullary nails or rods or pins, implants, interbody cages, fusion cages, and the like.

As used herein, an "assembly" refers to a collection, set, or kit of two or more structures, components, parts, systems, and/or sub-systems that together may be used, connected, coupled, applied, integrated, or adapted to be used to perform one or more functions and/or features. An assembly may include a modifier that identifies one or more particular functions or operations that can be accomplished using the assembly. Examples of such modifiers applied to an assembly, include, but are not limited to, "measurement assembly," "correction assembly," "fixation assembly," "separation assembly," "cutting assembly," and the like.

As used herein, a "fixator" refers to an apparatus, instrument, structure, device, component, member, system, assembly, or module structured, organized, configured, designed, arranged, or engineered to connect two bones or bone fragments or a single bone or bone fragment and another fixator to position and retain the bone or bone fragments in a desired position and/or orientation. Fixators can also serve to redistribute load and stresses experienced by bone(s) and/or body parts and can serve to reduce relative motion of one part relative to others. Examples of fixators include both those for external fixation as well as those for internal fixation and include, but are not limited to pins, wires, Kirschner wires, screws, anchors, bone anchors, plates, bone plates, intramedullary nails or rods or pins, implants, interbody cages, fusion cages, and the like.

As used herein, a "bone plate" refers to a structure having a generally planar structure. Often, a bone plate is flat or mostly flat. Certain embodiments, of bone plates can include one or more bends connected to, or integrated with, the bone plate. In certain embodiments, a bone plate can include bends that correspond to contours of a body part of a patient. In certain embodiments, a bone plate can be configured to support a load (including a tension, compression, shear, torsion, and/or bending load). A bone plate can be a separate structure connected to, or integrated with, another structure. Alternatively, a bone plate can be connected to part of another structure. A bone plate can be two-dimensional or three-dimensional and can have a variety of geometric shapes and/or cross-sectional shapes, including, but not limited to a rectangle, a square, or other polygon, as well as a circle, an ellipse, an ovoid, or other circular or semi-circular shape. A bone plate may be made from a variety of materials including, but not limited to, metal, plastic, ceramic, wood, fiberglass, acrylic, carbon, biocompatible materials, biodegradable materials or the like. A bone plate may be formed of any biocompatible materials, including but not limited to biocompatible metals such as Titanium, Titanium alloys, stainless steel, carbon fiber, combinations of carbon fiber and a metallic alloy, stainless steel alloys, cobalt-chromium steel alloys, nickel-titanium alloys, shape memory alloys such as Nitinol, biocompatible ceramics, and biocompatible polymers such as Polyether ether ketone (PEEK) or a polylactide polymer (e.g. PLLA) and/or others, or any combination of these materials. One bone plate may be distinguished from another based on where the plate is positioned within a structure, component, or apparatus.

As used herein, a "fastener", "fixation device", or "fastener system" refers to any structure configured, designed, or engineered to join two structures. Fasteners may be made of a variety of materials including metal, plastic, composite materials, metal alloys, plastic composites, and the like. Examples of fasteners include, but are not limited to screws, rivets, bolts, nails, snaps, hook and loop, set screws, bone screws, nuts, posts, pins, thumb screws, and the like. Other examples of fasteners include, but are not limited to wires, Kirschner wires (K-wire), anchors, bone anchors, plates, bone plates, intramedullary nails or rods or pins, implants, sutures, soft sutures, soft anchors, tethers, interbody cages, fusion cages, and the like.

In certain embodiments, the term fastener may refer to a fastener system that includes two or more structures configured to combine to serve as a fastener. An example of a fastener system is a rod or shaft having external threads and an opening or bore within another structure having corresponding internal threads configured to engage the external threads of the rod or shaft. In certain embodiments, the term fastener may be used with an adjective that identifies an object or structure that the fastener may be particularly configured, designed, or engineered to engage, connect to, join, contact, or couple together with one or more other structures of the same or different types. For example, a "bone fastener" may refer to an apparatus for joining or connecting one or more bones, one or more bone portions, soft tissue and a bone or bone portion, hard tissue and a bone or bone portion, an apparatus and a bone or portion of bone, or the like.

In certain embodiments, a fastener may be a temporary fastener. A temporary fastener is configured to engage and serve a fastening function for a relatively short period of time. Typically, a temporary fastener is configured to be used until another procedure or operation is completed and/or until a particular event. In certain embodiments, a user may remove or disengage a temporary fastener. Alternatively, or in addition, another structure, event, or machine may cause the temporary fastener to become disengaged.

As used herein, a "guide" refers to a part, component, or structure designed, adapted, configured, or engineered to guide or direct one or more other parts, components, or structures. A guide may be part of, integrated with, connected to, attachable to, or coupled to, another structure, device, or instrument. In one embodiment, a guide may include a modifier that identifies a particular function, location, orientation, operation, type, and/or a particular structure of the guide. Examples of such modifiers applied to a guide, include, but are not limited to, "pin guide" that guides or directs one or more pins, a "cutting guide" that guides or directs the making or one or more cuts, and the like.

As used herein, an "opening" refers to a gap, a hole, an aperture, a space or recess in a structure, a void in a structure, or the like. In certain embodiments, an opening can refer to a structure configured specifically for receiving something and/or for allowing access. In certain embodiments, an opening can pass through a structure. In other embodiments, an opening can exist within a structure but not pass through the structure. An opening can be two-dimensional or three-dimensional and can have a variety of geometric shapes and/or cross-sectional shapes, including, but not limited to a rectangle, a square, or other polygon, as well as a circle, an ellipse, an ovoid, or other circular or semi-circular shape. As used herein, the term "opening" can include one or more modifiers that define specific types of "openings" based on the purpose, function, operation, position, or location of the "opening." As one example, a "fastener opening" refers to an "opening" adapted, configured, designed, or engineered to accept or accommodate a "fastener."

As used herein, "bend" refers to an angled or curved structure, or a part or a portion of a structure, that changes an orientation of the structure. The structure that includes the bend can be a pipe, a tube, a cable, a hose, a sheet, a path, an opening, a portal, a building, a road, or the like. Typically, a bend changes an orientation of the structure at an angle between 0 and 180 degrees or between 180 degrees and 360 degrees along a longitudinal axis of the structure. The structure can include a single bend or a plurality of bends.

As used herein, "implant" refers to a medical device manufactured to replace a missing biological structure, support a damaged biological structure, or enhance an existing biological structure. Medical implants are man-made devices. The surface of implants that contact the body may be made of, or include a biomedical material such as titanium, stainless steel, carbon fiber, another metallic alloy, silicone, or apatite, or any combination of these depending on what is the most functional. In some cases implants contain electronics, e.g. artificial pacemaker and cochlear implants. Some implants are bioactive, such as subcutaneous drug delivery devices in the form of implantable pills or drug-eluting stents. Orthopedic implants may be used to alleviate issues with bones and/or joints of a patient's body. Orthopedic implants are used to treat bone fractures, osteoarthritis, scoliosis, spinal stenosis, and chronic pain. Examples of orthopedic implants include, but are not limited to, a wide variety of pins, rods, screws, anchors, and plates used to anchor fractured bones while the bones heal or fuse together. (Search "implant (medicine)" on Wikipedia.com May 26, 2021. CC-BY-SA 3.0 Modified. Accessed Jun. 30, 2021.)

As used herein, a "body" refers to a main or central part of a structure. The body may serve as a structural component to connect, interconnect, surround, enclose, and/or protect one or more other structural components. A body may be made from a variety of materials including, but not limited to, metal, plastic, ceramic, wood, fiberglass, acrylic, carbon, biocompatible materials, biodegradable materials or the like. A body may be formed of any biocompatible materials, including but not limited to biocompatible metals such as Titanium, Titanium alloys, stainless steel alloys, cobalt-chromium steel alloys, nickel-titanium alloys, shape memory alloys such as Nitinol, biocompatible ceramics, and biocompatible polymers such as Polyether ether ketone (PEEK) or a polylactide polymer (e.g. PLLA) and/or others.

In one embodiment, a body may include a housing or frame or framework for a larger system, component, structure, or device. A body may include a modifier that identifies a particular function, location, orientation, operation, and/or a particular structure relating to the body. Examples of such modifiers applied to a body, include, but are not limited to, "inferior body," "superior body," "lateral body," "medial body," and the like.

As used herein, an "extender" or "extension" refers to an apparatus, instrument, structure, device, component, member, system, assembly, or module structured, organized, configured, designed, arranged, or engineered to extend or continue providing one or more features, functions, attributes, characteristics, and/or advantages of a first structure associated with the extender. An extender can include a coupling, connector, or connection feature that enables the extender to connect to, communicate with, or interact with the first structure. An extender or extension may be made from a variety of materials including, but not limited to, metal, plastic, ceramic, wood, fiberglass, acrylic, carbon, biocompatible materials, biodegradable materials or the like. An "extender" or "extension" may be formed of any biocompatible materials, including but not limited to biocompatible metals such as Titanium, Titanium alloys, stainless steel alloys, cobalt-chromium steel alloys, nickel-titanium alloys, shape memory alloys such as Nitinol, biocompatible ceramics, and biocompatible polymers such as Polyether ether ketone (PEEK) or a polylactide polymer (e.g. PLLA) and/or others, or any combination of these materials.

As used herein, a "shaft" refers to a long narrow structure, device, component, member, system, or assembly structured, organized, configured, designed, arranged, or engineered to support and/or connect a structure, device, component, member, system, connected to each end of the shaft. Typically, a shaft is configured to provide rigid support and integrity in view of a variety of forces including tensile force, compression force, torsion force, shear force, and the like. In addition, a shaft can be configured to provide rigid structural support and integrity in view of a loads including axial loads, torsional loads, transverse loads, and the like. A shaft may be oriented and function in a variety of orientations including vertical, horizontal, or any orientation between these and in two or three dimensions. A shaft may be made from a variety of materials including, but not limited to, metal, plastic, ceramic, wood, fiberglass, acrylic, carbon, biocompatible materials, biodegradable materials or the like. A shaft may be formed of any biocompatible materials, including but not limited to biocompatible metals such as Titanium, Titanium alloys, stainless steel alloys, cobalt-chromium steel alloys, nickel-titanium alloys, shape memory alloys such as Nitinol, biocompatible ceramics, and biocompatible polymers such as Polyether ether ketone (PEEK) or a polylactide polymer (e.g. PLLA) and/or others, or any combination of these materials.

As used herein, "coupling", "coupling member", or "coupler" refers to a mechanical device, apparatus, member, component, system, assembly, or structure, that is organized, configured, designed, arranged, or engineered to connect, or facilitate the connection of, two or more parts, objects, or structures. In certain embodiments, a coupling can connect adjacent parts or objects at their ends. In certain embodiments, a coupling can be used to connect two shafts together at their ends for the purpose of transmitting power. In other embodiments, a coupling can be used to join two pieces of rotating equipment while permitting some degree of misalignment or end movement or both. In certain embodiments, couplings may not allow disconnection of the two parts, such as shafts during operation. (Search "coupling" on Wikipedia.com Jul. 26, 2021. CC-BY-SA 3.0 Modified. Accessed Jul. 27, 2021.) A coupler may be flexible, semi-flexible, pliable, elastic, or rigid. A coupler may join two structures either directly by connecting directly to one structure and/or directly to the other or indirectly by connecting indirectly (by way of one or more intermediary structures) to one structure, to the other structure, or to both structures.

As used herein, a "long bone" refers to a bone of a patient having a length greater than a width of the bone. Long bone is one of five types of bones: long, short, flat, irregular and sesamoid. Long bones, especially the femur and tibia, can be subjected to most of the load during daily activities. Long bones grow primarily by elongation of the diaphysis, with an epiphysis at each end of the growing bone. The ends of epiphyses are covered with hyaline cartilage ("articular cartilage"). The longitudinal growth of long bones is a result of endochondral ossification at the epiphyseal plate. The long bone category type includes the femur, tibia, and fibula of the legs; the humerus, radius, and ulna of the arms; metacarpals and metatarsals of the hands and feet, the phalanges of the fingers and toes, and the clavicles or collar bones in humans or other patients. The outside of the long bone consists of a layer of connective tissue called the periosteum. Additionally, the outer shell of the long bone is compact bone, then a deeper layer of cancellous bone (spongy bone) which includes a medullary cavity that includes bone marrow. (Search "long bone" on Wikipedia. com May 14, 2021. CC-BY-SA 3.0 Modified. Accessed Jul. 26, 2021.)

As used herein, "periprosthetic" refers to a structure positioned in close relation to an implant. Periprosthetic can also be used as an adjective to describe a type of bone fracture. For example, a periprosthetic fracture is a fracture near or around an implant of prosthetic. (Search "peripros-thetic" on Wikipedia.com Sep. 20, 2020. CC-BY-SA 3.0 Modified. Accessed Jul. 26, 2021.)

As used herein, an "arm" refers to an elongated structure that extends from another structure such as a base or a body. In certain embodiments, an arm can be configured to support a load (including a tension, compression, shear, torsion, and/or bending load). In certain embodiments, an arm may comprise a generally planar structure. An arm can be a separate structure connected to, or integrated with, another structure. Based on how the arm connects to or extends from another structure, such as a base or body, the arm can resemble an arm of a human or animal in that the arm can be an appendage to another structure. An arm can be two-dimensional or three-dimensional and can have a variety of geometric shapes and/or cross-sectional shapes, including, but not limited to a rectangle, a square, or other polygon, as well as a circle, an ellipse, an ovoid, or other circular or semi-circular shape. An arm can be made from a variety of materials including, metal, plastic, ceramic, wood, fiberglass, or the like. One arm may be distinguished from another based on where the arm is positioned within a structure, component, or apparatus.

As used herein, "adapter" refers to a device, component, system, assembly, or structure, that is organized, configured, designed, arranged, or engineered to convert or convey attributes, features, or functions of one device, component, or structure, for use with an otherwise incompatible device, component, system, assembly, or structure. (Search "adapter" on Wikipedia.com May 13, 2021. CC-BY-SA 3.0 Modified. Accessed Jul. 27, 2021.) An adapter may include one or more modifiers that identify one or more particular functions, attributes, advantages, uses, purposes, or operations and/or particular structures relating to the adapter. Examples of such modifiers applied to a feature, include, but are not limited to, "offset adapter," "accessibility adapter," "accommodation adapter," "detour adapter," "routing adapter," "rerouting adapter," and the like.

As used herein, a "deploy" or "deployment" refers to an act, action, process, system, method, means, or apparatus for inserting an implant or prosthesis into a part, body part, and/or patient. "Deploy" or "deployment" can also refer to an act, action, process, system, method, means, or apparatus for placing something into therapeutic use. A device, system, component, medication, drug, compound, or nutrient may be deployed by a human operator, a mechanical device, an automated system, a computer system or program, a robotic system, or the like.

As used herein, "feature" refers to a distinctive attribute or aspect of something. (Search "feature" on google.com. Oxford Languages, 2021. Web. 20 Apr. 2021.) A feature may include one or more modifiers that identify one or more particular functions, attributes, advantages, or operations and/or particular structures relating to the feature. Examples of such modifiers applied to a feature, include, but are not limited to, "attachment feature," "securing feature," "alignment feature," "adjustment feature," "guide feature," "protruding feature," "engagement feature," "fixation feature", "disengagement feature," and the like.

Any methods disclosed herein comprise one or more steps or actions for performing the described method. The method steps and/or actions may be interchanged with one another. In other words, unless a specific order of steps or actions is required for proper operation of the embodiment, the order and/or use of specific steps and/or actions may be modified.

The phrases "connected to," "coupled to" and "in communication with" refer to any form of interaction between two or more entities, including mechanical, electrical, magnetic, electromagnetic, fluid, and thermal interaction. Two components may be functionally coupled to each other even though they are not in direct contact with each other. The term "abutting" refers to items that are in direct physical contact with each other, although the items may not necessarily be attached together. The phrase "fluid communication" refers to two features that are connected such that a fluid within one feature can pass into the other feature.

The word "exemplary" is used herein to mean "serving as an example, instance, or illustration." Any embodiment described herein as "exemplary" is not necessarily to be construed as preferred or advantageous over other embodiments. While the various aspects of the embodiments are presented in drawings, the drawings are not necessarily drawn to scale unless specifically indicated.

Reference throughout this specification to "an embodiment" or "the embodiment" means that a particular feature, structure or characteristic described in connection with that embodiment is included in at least one embodiment. Thus, the quoted phrases, or variations thereof, as recited throughout this specification are not necessarily all referring to the same embodiment.

Similarly, it should be appreciated that in the above description of embodiments, various features are sometimes grouped together in a single embodiment, FIG., or description thereof for the purpose of streamlining the disclosure. This method of disclosure, however, is not to be interpreted as reflecting an intention that any claim require more features than those expressly recited in that claim. Rather, as the following claims reflect, inventive aspects lie in a combination of fewer than all features of any single foregoing disclosed embodiment. Thus, the claims following this Detailed Description are hereby expressly incorporated into this Detailed Description, with each claim standing on its own as a separate embodiment. This disclosure includes all permutations of the independent claims with their dependent claims.

Recitation in the claims of the term "first" with respect to a feature or element does not necessarily imply the existence of a second or additional such feature or element. Elements recited in means-plus-function format are intended to be construed in accordance with 35 U.S.C. § 112 Para. 6. It will be apparent to those having skill in the art that changes may be made to the details of the above-described embodiments without departing from the underlying principles set forth herein.

While specific embodiments and applications of the present disclosure have been illustrated and described, it is to be understood that the scope of this disclosure is not limited to the precise configuration and components disclosed herein. Various modifications, changes, and variations which will be apparent to those skilled in the art may be made in the arrangement, operation, and details of the methods and systems of the present disclosure set forth herein without departing from it spirit and scope.

What is claimed is:

1. A system that enables insertion of an intramedullary nail and a bone plate, the system comprising:
    an intramedullary nail configured to span a fracture in a bone;
    a bone plate configured to span the fracture; and
    a combined inserter comprising:
        a body comprising a longitudinal axis, a distal end, and a proximal end;
        an intramedullary nail coupler coupled to the body and configured to couple to an intramedullary nail; and
        a bone plate coupler coupled to the body and configured to couple to the bone plate;
    wherein:
        the bone plate coupler is configured to be adjustable along a transverse axis that is transverse to the longitudinal axis;
        the bone plate is configured to contact an epiphysis and a diaphysis of the bone;
        the combined inserter is configured to insert the intramedullary nail into a distal femur; and
        the combined inserter is configured to enable simultaneous attachment to the intramedullary nail and the bone plate.

2. The system of claim 1, wherein the bone plate coupler comprises:
    a longitudinal translation feature configured to translate the bone plate coupler along the longitudinal axis between the proximal end and the distal end;

a transverse feature configured to translate the bone plate coupler along the transverse axis; and a rotational feature configured to rotate the bone plate about a longitudinal bone plate axis.

3. The system of claim 2, wherein the longitudinal translation feature comprises:

a track between the proximal end and the distal end, the track comprising one or more offset positions and a nail alignment position configured to align the intramedullary nail and the bone plate with each other for deployment within a patient; and a latch configured to secure the longitudinal translation feature in one of the one or more offset positions and the nail alignment position.

4. The system of claim 3, wherein the nail alignment position comprises an alignment of at least one fastener opening of the bone plate with at least one corresponding fastener opening of the intramedullary nail such that a fastener deployed within the at least one fastener opening of the bone plate engages the at least one corresponding fastener opening of the intramedullary nail.

5. The system of claim 3, wherein one of the one or more offset positions position the bone plate such that advancement of the combined inserter toward a bone of a patient causes the intramedullary nail to enter an intramedullary canal of the bone before the bone plate percutaneously advances along a side of the bone, the combined inserter comprising the intramedullary nail and the bone plate.

6. The system of claim 3, wherein one of the one or more offset positions position the bone plate such that advancement of the combined inserter toward a bone of a patient causes the bone plate to percutaneously advance along a side of the bone before the intramedullary nail enters an intramedullary canal of the patient, the combined inserter comprising the intramedullary nail and the bone plate.

7. The system of claim 2, wherein the transverse feature comprises:

a base;

a telescoping member configured to fit within the base; and a fastener configured to secure the telescoping member within the base;

wherein extending or retracting the telescoping member advances or retracts the bone plate along the transverse axis.

8. The system of claim 2, wherein the rotational feature connects the bone plate to the transverse feature.

9. The system of claim 8, wherein the rotational feature comprises a clevis joint.

10. The system of claim 2, wherein one or more of the longitudinal translation feature, the transverse feature, and the rotational feature comprise a deployment configuration configured to position an intramedullary nail coupled to the intramedullary nail coupler relative to a bone plate coupled to the bone plate coupler for deployment of fasteners.

11. The system of claim 10, wherein the body comprises a guide section, the guide section comprising a set of nail engagement openings and a set of nail avoidance openings, each of the nail engagement openings and the nail avoidance openings aligned with a fastener opening of the bone plate.

12. The system of claim 11, wherein the guide section includes at least one indicator of one of the set of nail engagement openings and the set of nail avoidance openings.

13. The system of claim 1, wherein the intramedullary nail coupler comprises a coupling configured to releasably connect the intramedullary nail coupler to the body.

14. The system of claim 1, wherein the body comprises a distal handle proximal to the distal end and a proximal handle near the proximal end.

15. The combined inserter of claim 1, wherein the intramedullary nail comprises a generally constant cross-sectional diameter along its length.

16. The system of claim 1, wherein the combined inserter is configured to enable simultaneous insertion of the intramedullary nail and the bone plate.

17. A femur fixation system, comprising:

an intramedullary nail comprising a set of nail fastener openings configured to accept a fastener, the intramedullary nail configured to slide into an intramedullary canal of a distal end of a femur of a patient;

a bone plate comprising a set of plate fastener openings;

a combined inserter configured to enable simultaneous attachment to the intramedullary nail and the bone plate, the combined inserter comprising:

a body comprising a longitudinal axis, a distal end, and a proximal end;

an intramedullary nail coupler coupled to the body and configured to couple to the intramedullary nail;

a bone plate coupler coupled to the body and configured to couple to the bone plate; and a set of nail engagement openings that align with at least one of the set of nail fastener openings, the set of nail engagement openings disposed in the body;

a set of nail engagement fasteners configured to engage both the bone plate and the intramedullary nail when deployed; and a set of nail avoidance fasteners configured to engage the bone plate and the femur of the patient when deployed;

wherein:

the bone plate is configured to contact an epiphysis and a diaphysis of the femur;

a first plate fastener opening of the set of plate fastener openings is configured to be positioned on a first side of a fracture of the femur; and a second plate fastener opening of the set of plate fastener openings is configured to be positioned on a second side of the fracture.

18. The femur fixation system of claim 17, wherein at least one of the plate fastener openings comprises a nail avoidance opening.

19. The femur fixation system of claim 18, wherein the bone plate coupler comprises:

a transverse feature configured to bias the bone plate towards the femur and move the bone plate away from the femur in response to a force away from the femur; and a rotational feature comprising a pivot joint that enables the bone plate to move in at least two directions relative to the bone plate coupler.

20. The femur fixation system of claim 19, wherein the transverse feature and the rotational feature each comprise a deployment configuration configured to position the intramedullary nail coupled to the intramedullary nail coupler relative to the bone plate coupled to the bone plate coupler for deployment of the nail engagement fasteners and the nail avoidance fasteners.

21. The femur fixation system of claim 17, wherein the intramedullary nail comprises a generally constant cross-sectional diameter along its length.

22. The system of claim 17, wherein the combined inserter is configured to enable simultaneous insertion of the intramedullary nail and the bone plate.

23. A femur fixation system, comprising:

an intramedullary nail comprising a set of nail fastener openings configured to accept a fastener, the intramedullary nail configured to slide into an intramedullary canal of a femur of a patient;

a bone plate comprising a set of plate fastener openings;

a combined inserter comprising:

a body comprising a longitudinal axis, a distal end, and a proximal end;

an intramedullary nail coupler coupled to the body and configured to couple to the intramedullary nail;

a bone plate coupler coupled to the body; and a set of nail engagement openings that align with at least one of the set of nail fastener openings, the set of nail engagement openings disposed in the body;

a set of nail engagement fasteners configured to engage both the bone plate and the intramedullary nail when deployed; and a set of nail avoidance fasteners configured to engage the bone plate and the femur of the patient when deployed; wherein:

at least one of the bone plate coupler and the intramedullary nail coupler is movably coupled to the body such that a position and/or orientation of the bone plate relative to the intramedullary nail is adjustable;

the intramedullary nail is configured to span a fracture in the femur;

the bone plate is configured to span the fracture; and the bone plate is configured to contact an epiphysis and a diaphysis of the femur.

24. The femur fixation system of claim 23, wherein at least one of the plate fastener openings comprises a nail avoidance opening.

25. The femur fixation system of claim 23, wherein the bone plate coupler comprises a longitudinal translation feature configured to translate the bone plate coupler along the longitudinal axis between the proximal end and the distal end.

26. The system of claim 23, wherein the combined inserter is configured to enable simultaneous insertion of the intramedullary nail and the bone plate.

\* \* \* \* \*